US011780896B2

(12) United States Patent
Horowitz et al.

(10) Patent No.: US 11,780,896 B2
(45) Date of Patent: Oct. 10, 2023

(54) SYSTEMS, METHODS, AND COMPOUNDS FOR PROVIDING CHAPERONE ACTIVITY TO PROTEINS

(71) Applicant: Colorado Seminary Which Owns and Operates the University of Denver, Denver, CO (US)

(72) Inventors: Scott Horowitz, Englewood, CO (US); Adam Begeman, Denver, CO (US); Ahhyun Son, Denver, CO (US); Alexa Gomez, Thornton, CO (US); Theodore Litberg, Denver, CO (US)

(73) Assignee: University of Denver, Denver, CO (US)

( * ) Notice: Subject to any disclaimer, the term of this patent is extended or adjusted under 35 U.S.C. 154(b) by 176 days.

(21) Appl. No.: 17/098,571

(22) Filed: Nov. 16, 2020

(65) Prior Publication Data

US 2021/0147843 A1 May 20, 2021

Related U.S. Application Data

(60) Provisional application No. 62/935,481, filed on Nov. 14, 2019.

(51) Int. Cl.
*C07K 14/47* (2006.01)
*C12N 15/11* (2006.01)
*C12Q 1/6839* (2018.01)

(52) U.S. Cl.
CPC .......... *C07K 14/4702* (2013.01); *C12N 15/11* (2013.01); *C12N 2310/151* (2013.01); *C12Q 1/6839* (2013.01)

(58) Field of Classification Search
CPC ............... C07K 14/4702; C12N 15/11; C12N 2310/151; C12N 2310/18; C12Q 1/6839
See application file for complete search history.

(56) References Cited

U.S. PATENT DOCUMENTS 7,807,648 B2 * 10/2010 Kmiec .................... A61P 43/00
536/23.5

OTHER PUBLICATIONS

Butovskaya 2018 (Major G-Quadruplex Form of HIV-1 LTR Reveals a (3+1) Folding Topology Containing a Stem-Loop. J. Am. Chem. Soc. 140:13654-13662) (Year: 2018).*
Afroz et al., "Functional and Dynamic Polymerization of the ALS-Linked Protein TDP-43 Antagonizes Its Pathologic Aggregation", "Nature Communications", 2017, pp. 1-15, Publisher: www.nature.com/naturecommunications.
Balendra et al., "C9ORF72-Mediated ALS and FTD: Multiple Pathways to Disease", "Nat Rev Neurol.", Sep. 2018, pp. 544-558, vol. 14, No. 9.
Bassell et al., "Fragile X Syndrome: Loss of Local MRNA Regulation Alters Synaptic Development and Function", "Neuron", Oct. 23, 2008, pp. 201-214, vol. 60, Publisher: Elsevier Inc.
Benner et al., "Homer Software for Motif Discovery and Next Generation Sequencing Analysis", Feb. 20, 2017, p. 2, Publisher: Downloaded from https://web.archive.org/web/20171214034506/http://homer.ucsd.edu/homer on Feb. 11, 2021.
Bounedjah et al., "Free MRNA in Excess Upon Polysome Dissociation is a Scaffold for Protein Multimerization to Form Stress Granules", "Nucleic Acids Research", 2014, pp. 8678-8691, vol. 42, No. 13.
Cattaneo et al., "Nuclear Localization of Lactic Dehydrogenase With Single-Stranded DNA-Binding Properties", "Experimental Cell Research", 1985, pp. 130-140, vol. 161, Publisher: Academic Press Inc.
Conlon et al., "The C9ORF72 GGGGCC Expansion Forms RNA G-Quadruplex Inclusions and Sequesters HNRNP H to Disrupt Splicing in ALS Brains", "eLife", 2016, pp. 1-28, vol. 5.
Dejesus-Hernandez et al., "Expanded GGGGCC Hexanucleotide Repeat in Noncoding Region of C9ORF72 Causes Chromosome 9P-Linked FTD and ALD", "Neuron", 2011, pp. 245-256, vol. 72, Publisher: Elsevier Inc.
Derbis et al., "Quantitative Evaluation of Toxic Polyglycine Biosyntesis and Aggregation in Cell Models Expressing Expanded CGG Repeats", "Frontiers in Genetics", Jun. 2018, pp. 1-13, vol. 9.
Doctor et al., "Do Nucleic Acids Moonlight as Molecular Chaperones?", "Nucleic Acids Research", 2016, pp. 4835-4845, vol. 44, No. 10, Publisher: Oxford University Pres.
Donnelly et al., "RNA Toxicity From the ALS/FTD C9ORF72 Expansion is Mitigated by Antisense Intervention", "Neuron", Oct. 16, 2013, pp. 415-428, vol. 80, Publisher: Elsevier, Inc.
Fang et al., "Using Molecular Beacons to Probe Molecular Interactions Between Lactate Dehydrogenase and Single-Stranded DNA", "Anal. Chem.", 2000, pp. 3280-3285, vol. 72.
Foat et al., "Statistical Mechanical Modeling of Genome-Wide Transcription Factor Occupancy Data by Matrixreduce", "Bioinformatics", 2006, pp. e141-e149, vol. 22, No. 14, Publisher: Oxford University Press.
Frottin et al., "The Nucleolus Functions as a Phase-Separated Protein Quality Control Compartment", "Science", 2019, p. 17, Publisher: Downloaded from https://www.sciencemagazinedigital.org/sciencemagazine/26_july_2019/MobilePagedArticle.action?articleId=1507352#articleId1507352.
Gray et al., "Polyphosphate is a Primordial Chaperone", "Molecular Cell", Mar. 6, 2014, pp. 689-699, vol. 53, Publisher: Elsevier Inc.
Grosse et al., "Lactate Dehydrogenase and Glyceraldehyde-Phosphate Dehydrogenase Are Single-Stranded DNA-Binding Proteins That Affect the DNA-Polymerase-A-Primase Complex", "Eur. J. Biochem.", 1986, pp. 459-467, vol. 160, Publisher: FEBS.

(Continued)

*Primary Examiner* — Ram R Shukla
*Assistant Examiner* — Ruth Sophia Arieti
(74) *Attorney, Agent, or Firm* — Neugeboren O'Dowd PC

(57) ABSTRACT

Systems and method for providing chaperone activity to a protein-containing compound is disclosed. The method includes selecting a nucleic acid based on one or more of the nucleic acid's particular properties and a specific sequence of the nucleic acid and applying the nucleic acid to a compound comprising one or more proteins to provide chaperone activity to the compound.

3 Claims, 41 Drawing Sheets

Specification includes a Sequence Listing.

(56) References Cited

OTHER PUBLICATIONS

Hartl et al., "Molecular Chaperones in Protein Folding and Proteostasis", "Nature", 2011, pp. 324-332, vol. 475, Publisher: Macmillian Publishers.

Haslbeck et al., "A First Line of Stress Defense: Small Heat Shock Proteins and Their Function in Protein Homeostasis", "J Mol Biol.", 2015, pp. 1537-1548, vol. 427, No. 7.

Hausler et al., "C9ORF72 Nucleotide Repeat Structures Initiate Molecular Cascades of Disease", "Nature", 2014, pp. 1-21, Publisher: Macmillan Publishers Limited.

Hernandez et al., "Autism Spectrum Disorder in Fragile X Syndrome: A Longitudinal Evaluation", "Am J Med Genet A.", 2009, pp. 1125-1137, vol. 149A, No. 6.

Jain et al., "RNA Phase Transitions in Repeat Expansion Disorders", "Nature", 2017, pp. 243-247, vol. 546.

Jakob et al., "Chaperone Activity With a Redox Switch", "Cell", Feb. 5, 1999, pp. 341-352, vol. 96, Publisher: Cell Press.

Jakob et al., "Small Heat Shock Proteins Are Molecular Chaperones", "The Journal of Biological Chemistry", 1993, pp. 1517-1520, vol. 268, No. 3, Publisher: The American Society for Biochemistry and Molecular Biology, Inc., Published in: US.

Litberg et al., "DNA Facilitates Oligomerization and Prevents Aggregation Via DNA Networks", "Biophysical Journal", Jan. 7, 2020, pp. 162-171, vol. 118.

Manna et al., "Fluorescence-Based Tools to Probe G-Quadruplexes in Cell-Free and Cellular Environments", "RSC Adv.", 2018, pp. 25673-25694, vol. 8.

Paeschke et al., "Telomere End-Binding Proteins Control the Formation of G-Quadruplex DNA Structures in Vivo", "Nature Structural & Molecular Biology", Oct. 2005, pp. 847-854, vol. 12, No. 10.

Paramasivan et al., "Circular Dichroism of Quadruplex DNAs: Applications to Structure, Cation Effects and Ligand Binding", "Methods", 2007, pp. 324-331, vol. 43, Publisher: Elsevier Inc.

Patel et al., "ATP as a biological hydrotrope", "Science", 2017, pp. 753-756, Published in: US.

Renton et al., "A Hexanucleotide Repeat Expansion in C9ORF72 is the Cause of Chromosome 9P21-Linked ALS-FTD", "Neuron", Oct. 20, 2011, pp. 257-268, vol. 72, Publisher: Elsevier Inc.

Rhodes et al., "Survey and Summary G-Quadrupleses and Their Regulatory Roles in Biology", "Nucleic Acids Research", 2015, pp. 8627-8637, vol. 43, No. 18.

Sabharwal et al., "N-Methylmesoporphyrin IX Fluorescence as a Reporter of Strand Orientation in Guanine Quadruplexes", "FEBS Journal", 2014, pp. 1726-1737, vol. 281, Publisher: John Wiley & Sons Ltd.

Simone et al., "G-Quadruplex-Binding Small Molecules Ameliorate C9ORF72 FTD/ALS Pathology in Vitro and in Vivo", "EMBO Molecular Medicine", 2018, pp. 22-31, vol. 10, No. 1, Publisher: The Authors.

Sjekloca, "On the Aggregation Properties of FMRP—A Link With the FXTAS Syndrome?", "FEBS Journal", 2011, pp. 1912-1921, vol. 28, Publisher: The Authors Journal compilation.

Stefanovic et al., "Fragile X Mental Retardation Protein Interactions With a G Quadruplex Structure in the 3'-Untranslated Region of N2B MRNA", "Mol Biosyst.", 2015, pp. 3222-3230, vol. 11, No. 12.

Vasilyev et al., "Crystal Structure Reveals Specfic Recognition of a G-Quadruplex RNA By a B-Turn in the RGG Motif of FMRP", "Proceedings of the National Academy of Sciences", 2015, pp. E5391-E5400.

Zhang et al., "FMRP Interacts With G-Quadruplex Structures in the 3'-UTR of Its Dendritic Target SHANK1 MRNA", "RNA Biology", Nov. 2014, pp. 1364-1374, vol. 11, No. 11, Publisher: Taylor & Francis Group, LLC.

Ambrus, et al., "Solution Structure of the Biologically Relevant G-Quadruplex Element in the Human c-MYC Promoter. Implications for G-Quadruplex Stabilization," Biochemistry 2005, 44, 2048-2058.

Casadaban, "Transposition and Fusion of the fat Genes to Selected Promoters in *Escherichia coli* using Bacteriophage Lambda and Mu," J. Mol. Biol. (1976) 104, 541-555.

Haider, et al., "Crystal Structure of the Potassium Form of an Oxytricha nova G-quadruplex," J. Mol. Biol. (2002) 320, 189-200.

Macaya, et al., "Thrombin-binding DNA aptamer forms a unimolecular quadruplex structure in solution," Proc. Natl. Acad. Sci. USA, vol. 90, pp. 3745-3749, Apr. 1993.

Phan, et al., "Propeller-Type Parallel-Stranded G-Quadruplexes in the Human c-myc Promoter," J. Am. Chem. Soc., 2004, 126, 8710-8716.

Piatkevich, et al., "Extended Stokes Shift in Fluorescent Proteins: Chromophore—Protein Interactions in a Near-Infrared TagRFP675 Variant," Scientific Reports, 3:1847, DOI: 10.1038/srep01847, 2013.

Renciuk, et al., "Arrangements of human telomere DNA quadruplex in physiologically relevant K+ solutions," Nucleic Acids Research, 2009, vol. 37, No. 19, 6625-6634.

Sengar, et al., "Structure of a (3+1) hybrid G-quadruplex in the PARP1 promoter," Nucleic Acids Research, 2019, vol. 47, No. 3, 1564-1572.

Simonsson, et al., "DNA tetraplex formation in the control region of c-myc," Nucleic Acids Research, 1998, vol. 26, No. 5, 1167-1172.

\* cited by examiner

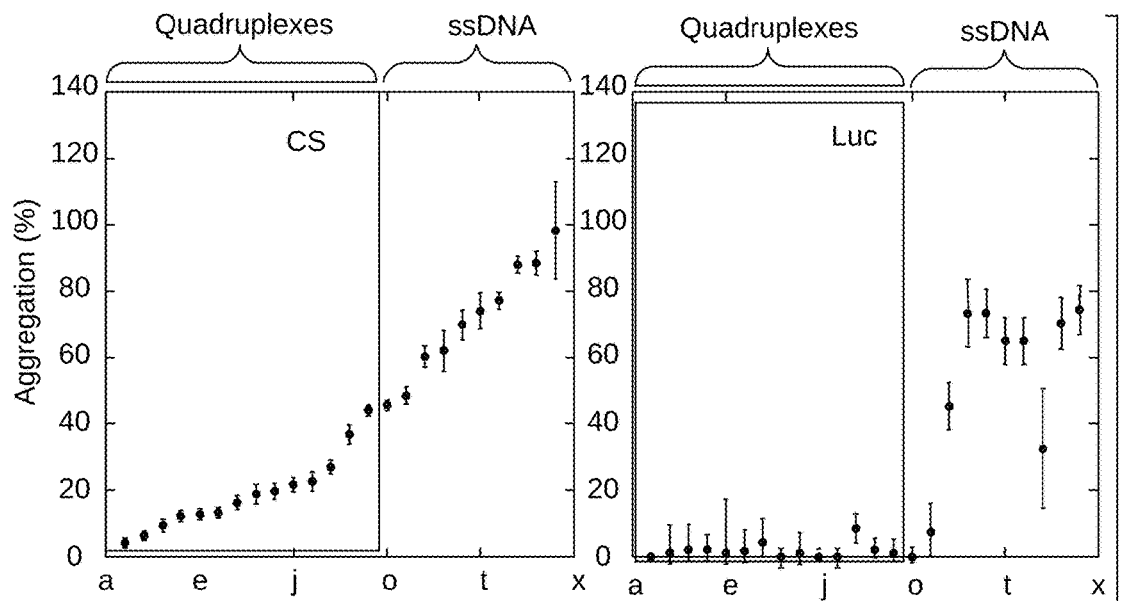
FIG. 5A   FIG. 5B
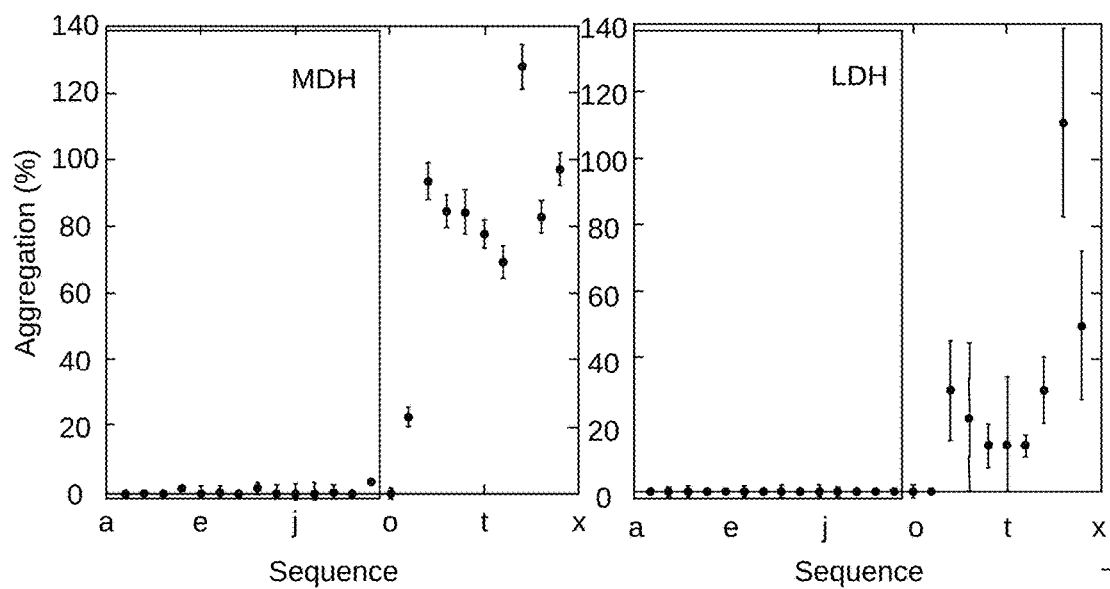
FIG. 5C   FIG. 5D

FIG. 16B-1  Taq-RFP675 + Empty
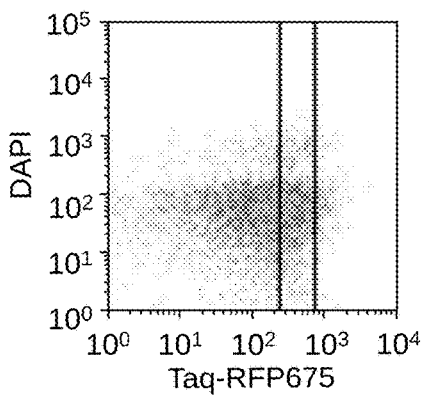
FIG. 16B-2  + GroEL
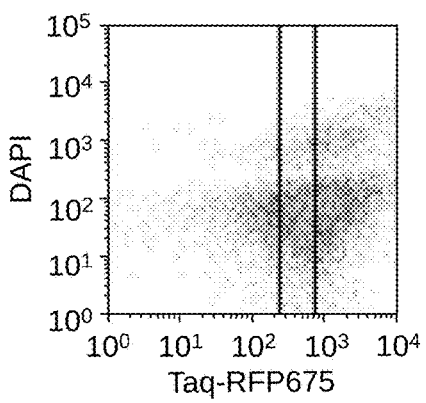
FIG. 16B-3  + Dnak
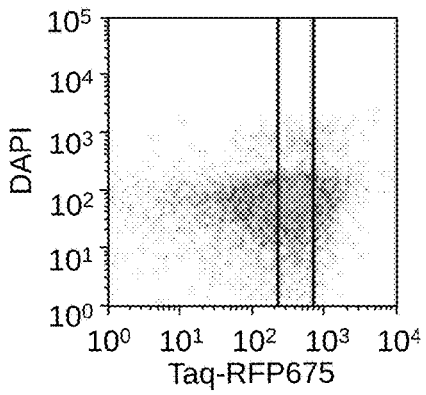
FIG. 16B-4  + Hsp33
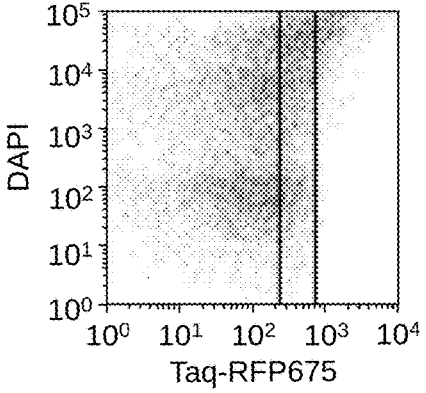
A

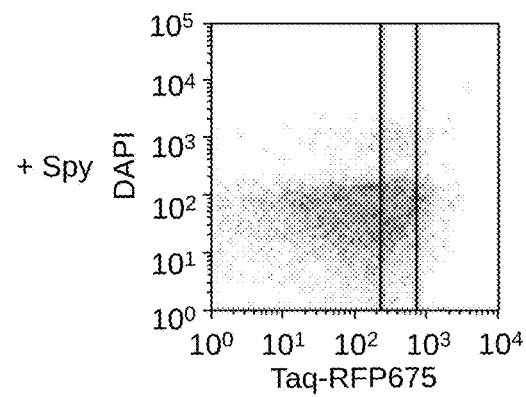
FIG. 16B-5  + Spy
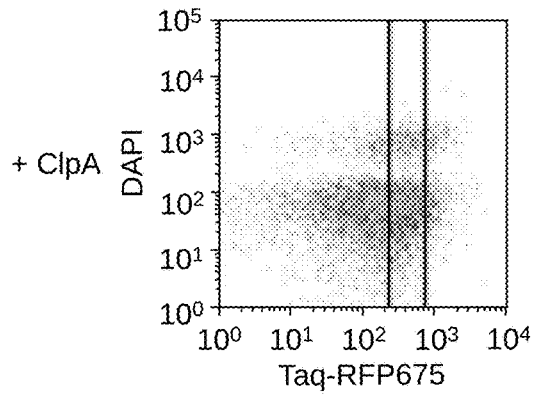
FIG. 16B-6  + ClpA
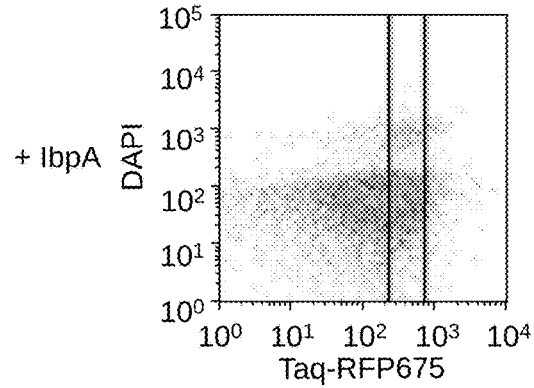
FIG. 16B-7  + IbpA
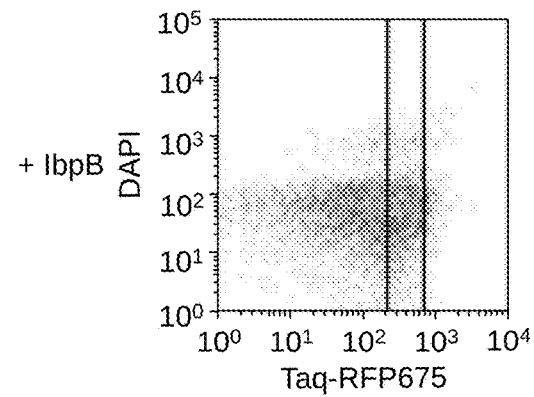
FIG. 16B-8  + IbpB

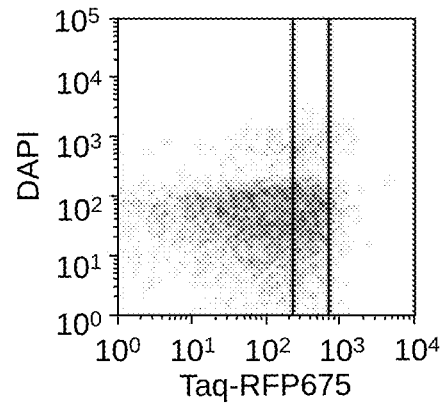
FIG. 16B-9  + Seq42
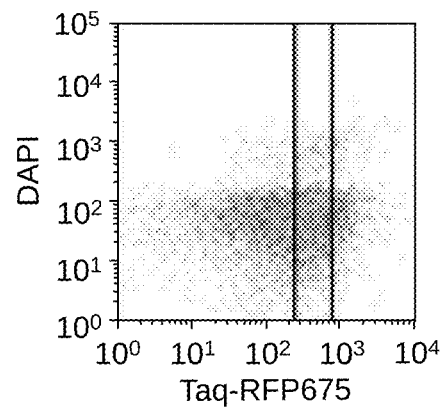
FIG. 16B-10  + Seq359
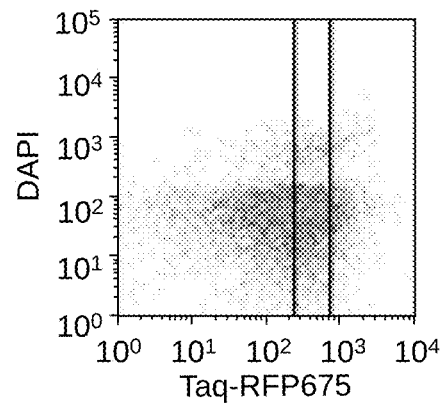
FIG. 16B-11  + Seq536
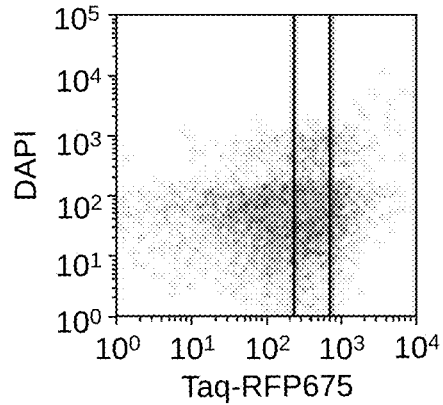
FIG. 16B-12  + Seq576

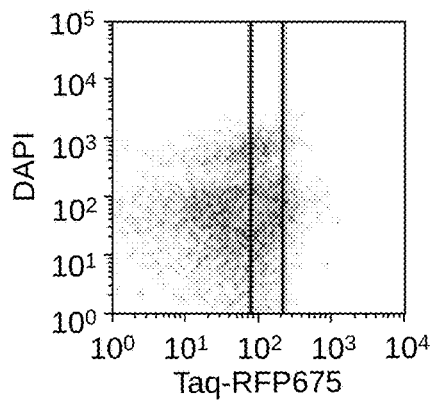
FIG. 16D-1  Taq-RFP675 + Empty
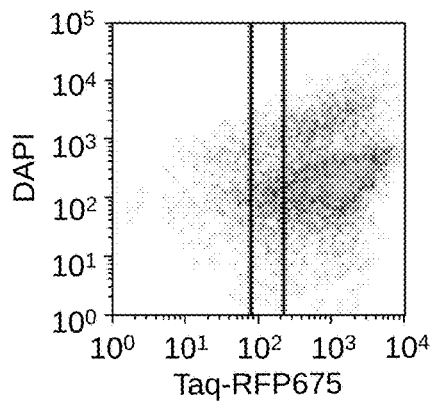
FIG. 16D-2  + GroEL
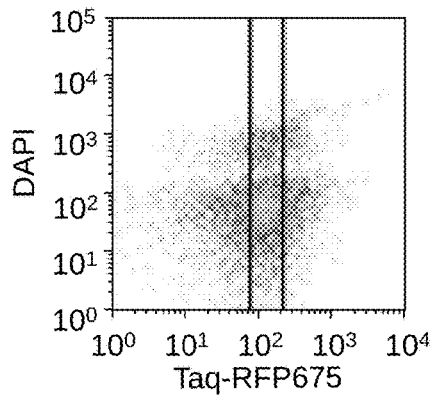
FIG. 16D-3  + Dnak
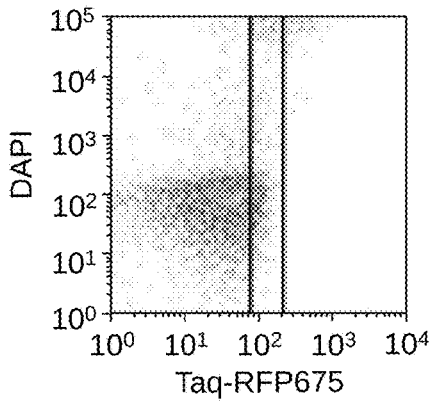
FIG. 16D-4  + Hsp33

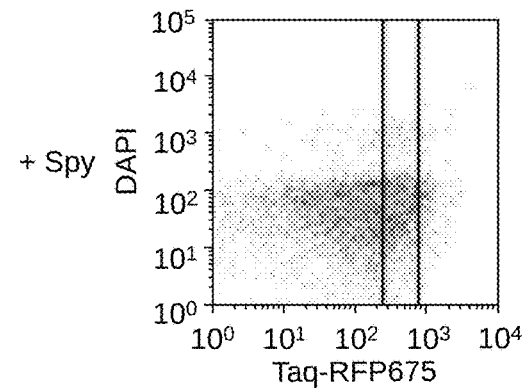
FIG. 16D-5  + Spy
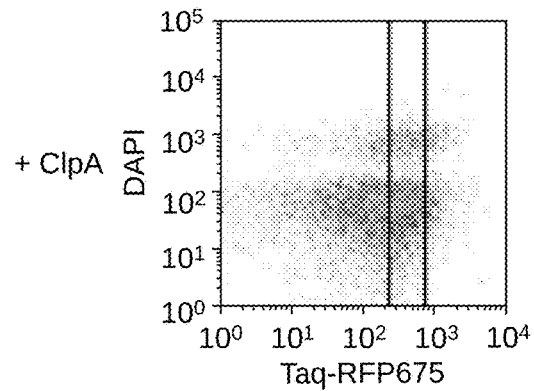
FIG. 16D-6  + ClpA
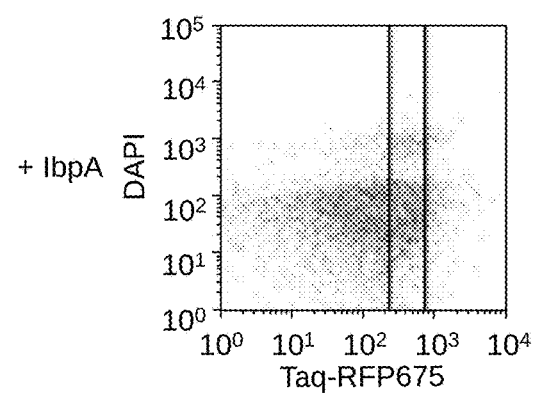
FIG. 16D-7  + IbpA
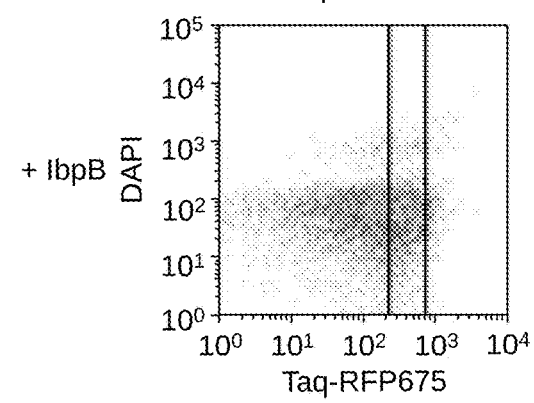
FIG. 16D-8  + IbpB

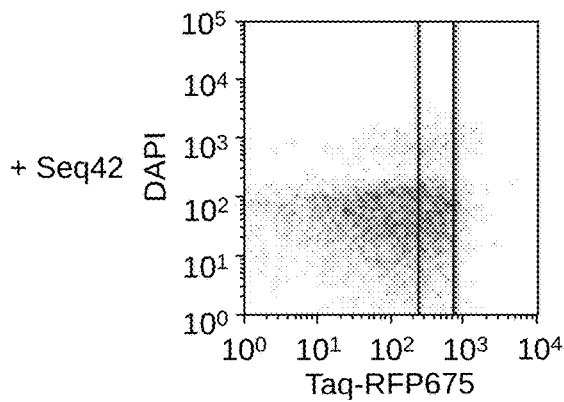
FIG. 16D-9  + Seq42
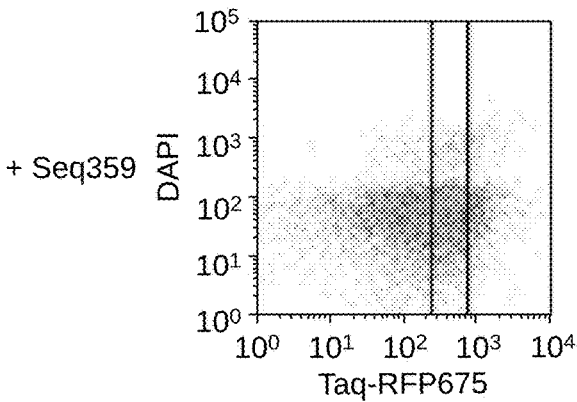
FIG. 16D-10  + Seq359
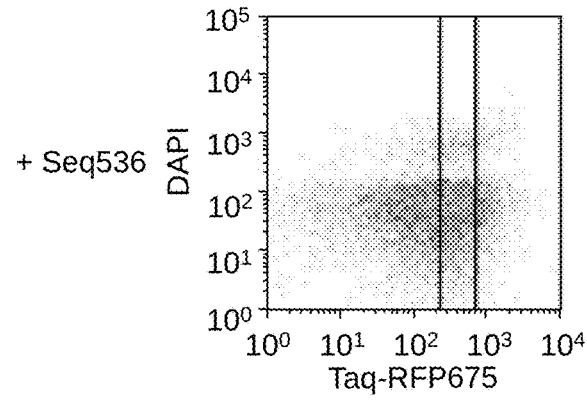
FIG. 16D-11  + Seq536
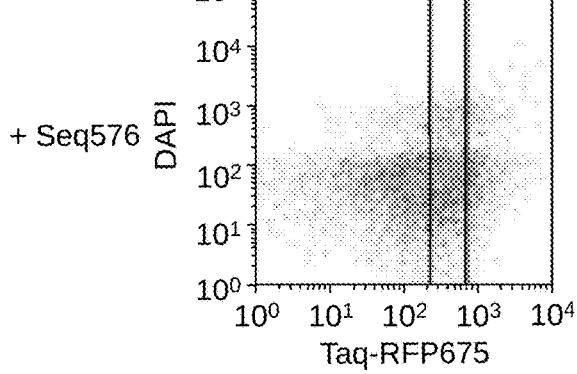
FIG. 16D-12  + Seq576

SYSTEMS, METHODS, AND COMPOUNDS FOR PROVIDING CHAPERONE ACTIVITY TO PROTEINS

SPONSORED RESEARCH AND DEVELOPMENT

This invention was made with government support under R00 GM120388 awarded by the National Institutes of Health. The government has certain rights in the invention.

CLAIM OF PRIORITY UNDER 35 U.S.C. § 119

The present Application for Patent claims priority to Provisional Application No. 62,935,481 entitled "METHODS AND COMPOUNDS FOR AFFECTING PROTEIN AGGREGATION LEVELS" filed Nov. 14, 2019, and assigned to the assignee hereof and hereby expressly incorporated by reference herein.

FIELD OF THE DISCLOSURE

The present disclosure relates generally to protein aggregation, oligomerization, and folding. In particular, but not by way of limitation, the present disclosure relates to systems, methods, and compounds for providing chaperone activity to proteins.

BACKGROUND

Chaperones are a diverse group of proteins and other molecules that regulate proteostasis in the cell by preventing protein aggregation (holdases) and helping protein folding (foldases). In many compounds, from pharmaceutical drugs to naturally occurring compounds found in and produced by plants, animals, and humans, it may be desirable to limit protein aggregation. Recently, molecules other than traditional protein chaperones have been shown to play important roles in these processes. It has also been recently shown that nucleic acids can possess potent holdase activity, with the best sequences having higher holdase activity than any previously characterized chaperone. Nucleic acids can also collaborate with Hsp70 to help protein folding, acting similarly to small heat shock proteins. Nucleic acids can also bring misfolded proteins to stress granules, and are a primary component of the nucleolus, which was recently shown to store misfolded proteins under stress conditions. However, the structural characteristics, sequence dependence, and mechanistic understanding of how nucleic acids act as chaperones has remained unclear.

Therefore, a need exists for demonstrating how particular nucleic acids act as chaperones and how such activity may be usefully applied to the prevention of protein aggregation in various compounds.

SUMMARY

The following presents a simplified summary relating to one or more aspects and/or embodiments disclosed herein. As such, the following summary should not be considered an extensive overview relating to all contemplated aspects and/or embodiments, nor should the following summary be regarded to identify key or critical elements relating to all contemplated aspects and/or embodiments or to delineate the scope associated with any particular aspect and/or embodiment. Accordingly, the following summary has the sole purpose to present certain concepts relating to one or more aspects and/or embodiments relating to the mechanisms disclosed herein in a simplified form to precede the detailed description presented below.

Some aspects of the present disclosure may be characterized a method for providing chaperone activity to a protein-containing compound. The method may include selecting a nucleic acid based on one or more of the nucleic acid's particular properties and a specific sequence of the nucleic acid. The method may also include applying the nucleic acid to a compound comprising one or more proteins to provide chaperone activity to the compound.

Other aspects of the present disclosure may be characterized as a product of a process for providing chaperone activity to a protein-containing compound. The product may include a solution that includes an oligonucleotide with a quadruplex-containing specific sequence, the oligonucleotide selected based on the specific sequence. The solution may also include one or more proteins to which chaperone activity is provided by the oligonucleotide.

Other aspects of the present disclosure may be characterized as a system configured for providing chaperone activity to a protein containing compound. The system may include means for selecting a nucleic acid based on one or more of the nucleic acid's particular properties and a specific sequence of the nucleic acid. The system may also include means for applying the nucleic acid to a compound comprising one or more proteins to provide chaperone activity to the compound.

Other aspects of the present disclosure may be characterized as a composition including as an active ingredient an effective amount of a nucleic acid to provide chaperone activity to a protein. The nucleic acid may include a G-quadruplex-containing specific sequence, wherein the nucleic acid is selected based on the specific sequence.

BRIEF DESCRIPTION OF THE DRAWINGS

FIGS. 1A-D illustrate exemplary results of an exemplary test for sequence dependence of chaperone nucleic acid activity, in accordance with one or more embodiments, wherein FIG. 1A illustrates a representative example of a citrate synthase protein aggregation assay, FIGS. 1B and 1C illustrate exemplary screens of ssDNA sequences for holdase chaperone activity, and FIG. 1D illustrates an exemplary HOMER Logo of motif found by analyzing an exemplary screen;

FIGS. 2A-D illustrate an exemplary characterization of nucleic acid quadruplex content and holdase activity (including Seq359 (SEQ ID NO:1), Seq536 (SEQ ID NO:2), Seq576 (SEQ ID NO:3), and Seq42 (SEQ ID NO:4)), in accordance with one or more embodiments, wherein FIG. 2A illustrates an exemplary structural characterization of nucleic acids using circular dichroism, FIG. 2B illustrates an exemplary characterization of nucleic acids using NMM fluorescence, FIG. 2C illustrates an exemplary characterization of citrate synthase aggregation during chemically induced denaturation, and FIG. 2D illustrates an exemplary characterization of holdase activity towards citrate synthase of ssDNA compared to its duplexed counterpart;

FIGS. 5A-5E illustrate exemplary experimental results regarding the generality of G-quadruplex holdase activity using four different proteins: Luciferase, Citrate Synthase, L-Malate Dehydrogenase, and L-Lactate Dehydrogenase (including SeqA (SEQ ID NO:1), SeqB (SEQ ID NO:5), SeqC (SEQ ID NO:6), SeqD (SEQ ID NO:7), SeqE (SEQ ID NO:8), SeqF (SEQ ID NO:2), SeqG (SEQ ID NO:9), SeqH (SEQ ID NO:10), SeqI (SEQ ID NO:11), SeqJ (SEQ ID NO:3), SeqK (SEQ ID NO:12), SeqL (SEQ ID NO:13), SeqM (SEQ ID NO:14), SeqN (SEQ ID NO:15), SeqO (SEQ ID NO:16), SeqP (SEQ ID NO:17), SeqQ (SEQ ID NO:18), SeqR (SEQ ID NO:19), SeqS (SEQ ID NO:20), SeqT (SEQ ID NO:21), SeqU (SEQ ID NO:22), SeqV (SEQ ID NO:23), SeqW (SEW ID NO:24), and SeqX (SEQ ID NO:25)), in accordance with one or more embodiments;

FIGS. 6A-C illustrate exemplary experimental results of quadruplex-containing sequences promoting oligomerization (including Seq359 (SEQ ID NO:1), Seq536 (SEQ ID NO:2), Seq576 (SEQ ID NO:3), and Seq42 (SEQ ID NO:4)), in accordance with one or more embodiments, wherein FIG. 6A illustrates an exemplary right-angle light scattering of chemically induced aggregation of citrate synthase, FIG. 6B illustrates an exemplary spin down assay with four different proteins denatured at 60° C. in the presence of DNA, and FIG. 6C illustrates exemplary transmission electron microscopy negative stain images of soluble fractions from chemically induced aggregation spin down assays;

FIGS. 9A-B illustrate exemplary results of exemplary spin down assays utilizing thermal aggregation of IgG antibodies, in accordance with one or more embodiments, wherein FIG. 9A illustrates exemplary results of a spin down assay including Seq42 (SEQ ID NO:4), Seq576 (SEQ ID NO:3), and Seq359 (SEQ ID NO:1), and FIG. 9B illustrates exemplary results of a spin down assay utilizing agitation and including Seq42 (SEQ ID NO:4) and Seq576 (SEQ ID NO:3);

FIGS. 13A-D illustrate an exemplary experiment showing the selection of sRNA sequences which have an effect on the folding status of TauK19, in accordance with one or more embodiments, wherein FIG. 13A shows an exemplary schematic illustration for selection of sRNA sequences, FIG. 13B illustrates exemplary expression vectors, FIG. 13C illustrates exemplary results of a protein aggregation assay using PROTEOSTAT® dye, and FIG. 13D illustrates an exemplary SDS-PAGE of TauK19 expression;

FIGS. 15A-C illustrate an exemplary experiment showing the effect of various folding enhancer factors on the folding status of TagRFP675, in accordance with one or more embodiments, wherein FIG. 15A shows an exemplary schematic illustration for determining the effect of various factors on the folding status of TagRFP675, FIG. 15B illustrates structures of exemplary expression vectors, and FIG. 15C illustrates results of an exemplary fluorescence assay of TagRFP675;

FIGS. 16A-G illustrate exemplary results of an exemplary experiment showing the folding status of TagRFP675 modulated by various folding enhancing factors (including Seq359 (SEQ ID NO:1), Seq536 (SEQ ID NO:2), Seq576 (SEQ ID NO:3), and Seq42 (SEQ ID NO:4)), in accordance with one or more embodiments, wherein FIG. 16A illustrates exemplary harvested cells, some of which were induced at 37° C., from the exemplary experiment showing color differences, FIGS. 16B-1-16B-12 illustrate exemplary experimental fluorescent-activated cell sorting results of TagRFP675, wherein some of the experimental cells were induced at 37° C., FIG. 16C illustrates exemplary harvested cells, some of which were induced at 42° C., from the exemplary experiment showing color differences, FIGS. 16D-1-16D-2 illustrate exemplary experimental fluorescent-activated cell sorting results of TagRFP675, wherein some of the experimental cells were induce at 42° C., FIG. 16E illustrates exemplary results of an exemplary cellular fluorescence assay of TagRFP675 with various folding enhancing factors, FIG. 16F illustrates exemplary expression vectors, one of which includes wtGFP, and FIG. 16G illustrates exemplary results of an exemplary cellular fluorescence assay of wtGFP with various folding enhancing factors;

DETAILED DESCRIPTION

Figure 1A:
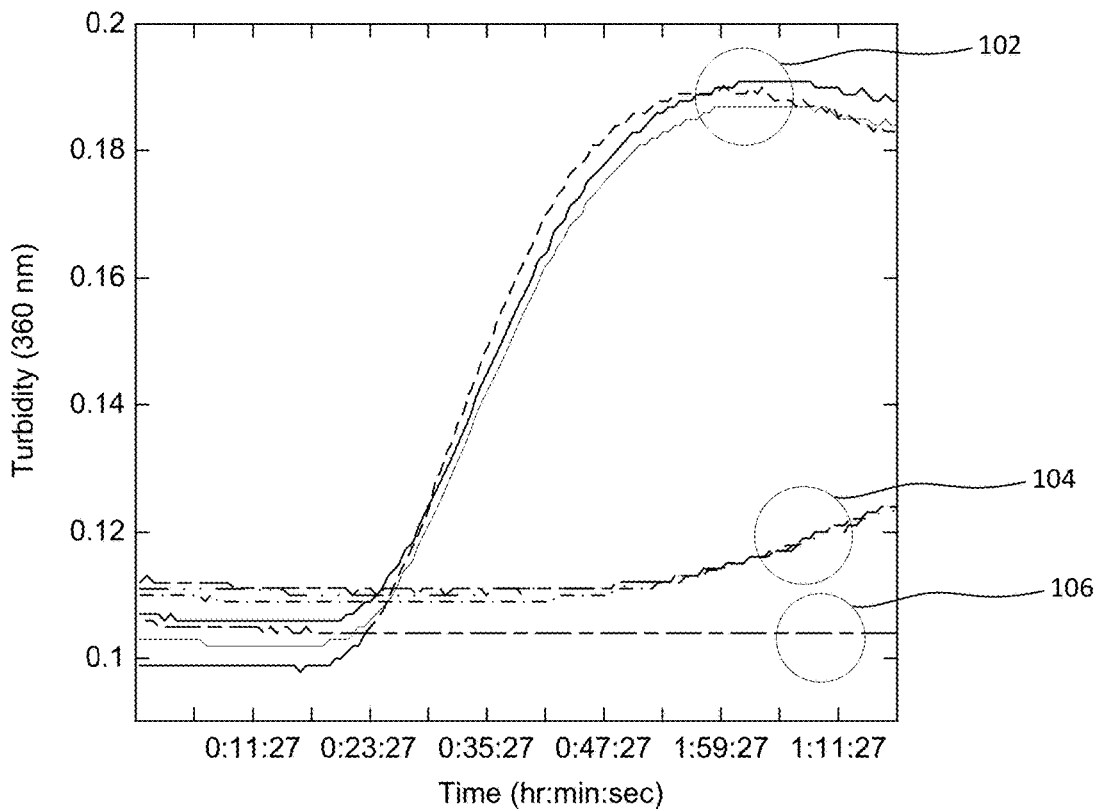

The word "exemplary" is used herein to mean "serving as an example, instance, or illustration." Any embodiment described herein as "exemplary" is not necessarily to be construed as preferred or advantageous over other embodiments.

The present disclosure provides systems, methods, and compounds that use nucleic acids in providing chaperone activity to proteins, such as through affecting protein aggregation in various synthetic and naturally occurring compounds. In embodiments, the methods include specifically using G-quadruplex nucleic acids to provide chaperone activity to proteins, such as to prevent protein aggregation or improve protein folding in synthetic or naturally occurring compounds, which may include effects produced by promoting protein-nucleic acid oligomerization. Further, in embodiments, the methods may include using sequence-specific G-quadruplex nucleic acids to tightly control the level of chaperone activity, such as to control protein aggregation or protein folding, in synthetic or naturally occurring compounds. Specific non-quadruplex nucleic acids that are also found to have effects on chaperone activity may be used in methods of the present disclosure. The teachings of the present disclosure may enable an increased stability of proteins in a variety of compounds and compositions, which may reduce costs associated with the degradation of such proteins as well as improve medical outcomes where protein stability is an important factor.

Synthetic compounds may include compounds that do not occur in nature in their synthetic form, such as compounds that have undergone alterations from their natural state, compounds that were synthesized outside of their naturally-occurring environment, or compounds that have been purified from their naturally-occurring form. For the purposes of the present disclosure, recombinant protein expression techniques may be considered to produce synthetic compounds as the compounds are produced outside of their naturally-occurring environment through the alteration of naturally-occurring genetic material. Examples of synthetic compounds to which the nucleic acids of the present disclosure may be applied include pharmaceutical compounds (including drugs and drug excipients), cosmetic compounds, industrial compounds, edible compounds for use in food, commercial compounds, and a variety of other protein-containing compounds. However, this is not an exhaustive list of synthetic compounds, and others may be used in methods of the present disclosure.

Examples of naturally occurring compounds to which nucleic acids of the present disclosure may be applied also include pharmaceutical compounds (both as drugs and drug excipients), cosmetic compounds, industrial compounds, edible compounds for use in food, commercial compounds and additionally include substances produced by plants, animals, and humans, such as extracts, fluids, and those comprising tissue. Nucleic acids of the present disclosure may also be applied to a variety of other naturally occurring, protein-containing compounds.

Methods for applying nucleic acids of the present disclosure to various compounds may include: dissolving in solution, mixing, topically applying, and expressing in organisms. Other methods of applying nucleic acids may also be used without departing from the scope of the disclosure.

Maintaining proteome health is important for cell survival. Nucleic acids possess the ability to prevent aggregation up to 300-fold more efficiently than traditional chaperone proteins. In the below experiments, the sequence specificity of the chaperone activity of nucleic acids is explored. Evaluating over 500 nucleic acid sequences' effects on aggregation, the experiments demonstrate that the holdase chaperone effect of nucleic acids may be highly sequence dependent. Quadruplexes, in particular, may have especially potent effects on aggregation with many different proteins via quadruplex:protein oligomerization. These observations contextualize recent reports of quadruplexes playing important roles in aggregation-related diseases, such as Fragile X and Amyotrophic lateral sclerosis (ALS).

A key question in understanding the holdase activity of nucleic acids is whether this activity is sequence specific? Previously, polyA, polyT, polyG, and polyC were shown to prevent aggregation with varying kinetics, suggesting that sequence specificity was possible. In the below experiments, sequence specificity may be tested by examining over 500 nucleic acids of varying sequence for holdase activity. The holdase activity may be highly sequence specific, with quadruplexes showing the greatest activity. Several quadruplexes may display generality, with potent holdase activity for a variety of different proteins. Such holdase activity may also be verified to occur in *Escherichia coli* (*E. coli*) through the below experiments. Further examination of specific quadruplex sequences can be used to demonstrate that the holdase activity may largely arise through quadruplex:protein oligomerization. The results of the below experiments may help explain several recent reports of quadruplex sequences playing important roles in oligomerization, aggregation, and phase separation in biology and pathology, and that these are common properties of quadruplex interactions with partially unfolded or disordered proteins. Additionally, the results may demonstrate the ability of nucleic acids in modulating protein folding in *E. coli*.

Sequence Specificity of Holdase Activity

The following paragraphs describe several experiments conducted to validate theories about particular nucleic acids discussed in the present disclosure and methods for utilizing them. Other systems, compounds, and methods may be implemented without departing from the scope of the present disclosure, and the experiments described herein should not be construed to be the only methods for implementation.

Figure 1B:
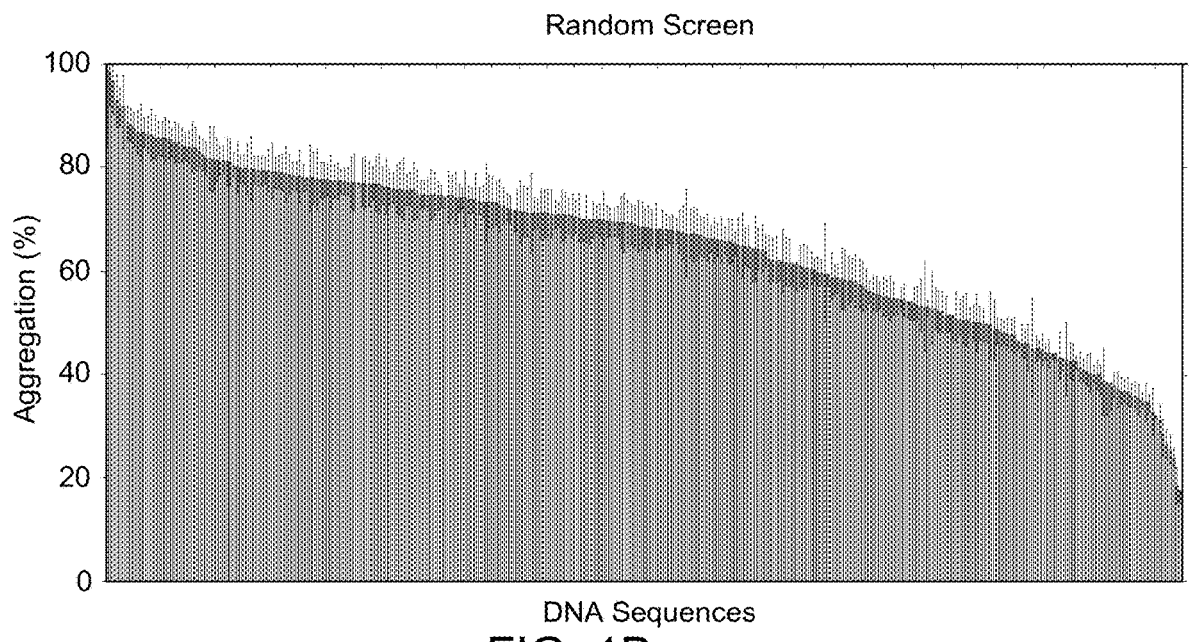
Figure 1C:
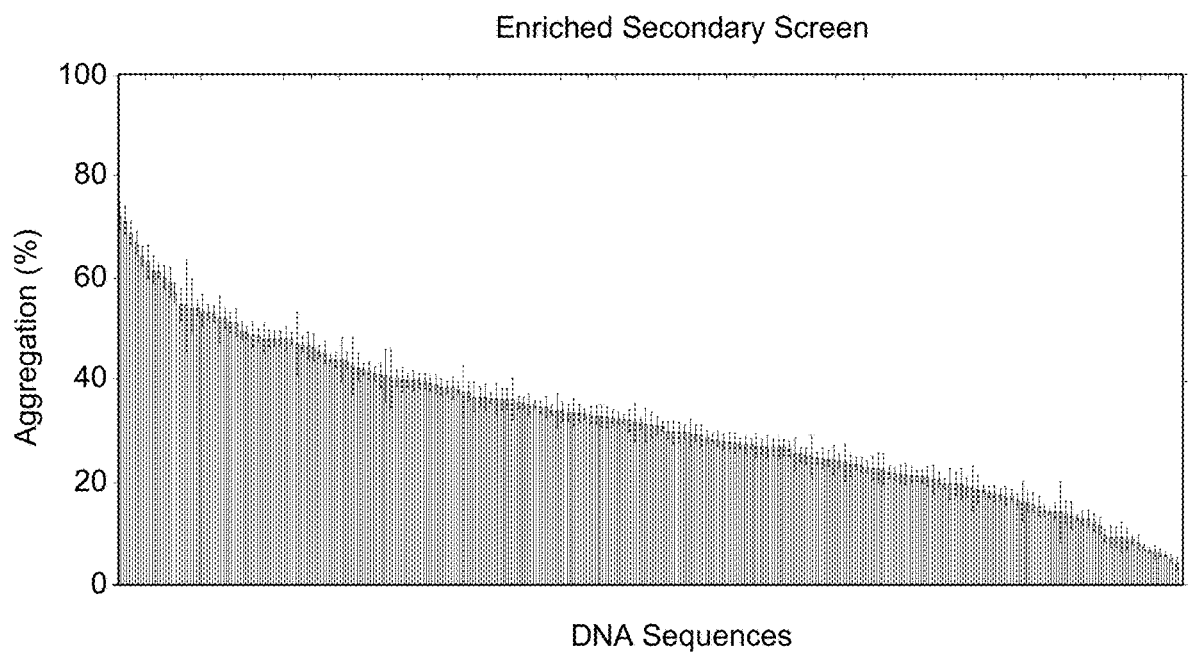

FIGS. 1A-D show the following results of an exemplary testing for sequence dependence of chaperone nucleic acid activity: (FIG. 1A) A representative example citrate synthase protein aggregation assay. Turbidity and light scattering were measured in a multimode plate reader at 360 nm for 1.5 hours of incubation at 50° C. The three sharply upward-trending lines 102 represent triplicate citrate synthase alone, the three slightly upward-trending lines 104 represent triplicate citrate synthase incubated with a single ssDNA sequence, and the nearly flat line 106 represents buffer alone. (FIGS. 1B and 1C) A screen of ssDNA sequences for holdase chaperone activity. Each bar represents a different 20-nt sequence, sorted by activity. Aggregation % was measured as the normalized average of triplicate citrate synthase turbidity measurements after 1.5 hours of incubation at 50° C. Lower aggregation may indicate greater holdase function. The initial screen used random, non-redundant sequences, as shown in FIG. 1B, which led to a followup enriched screen, as shown in FIG. 1C. Error bars are SE. (FIG. 1D) A HOMER Logo of motif found by analyzing screen (statistics: $p<1.0\times10^{-13}$, FDR<0.001, % of Targets: 53.85, % of Background: 7.69).

To determine the sequence specificity of the holdase activity of nucleic acids, light scattering and turbidity were measured via absorbance in a thermal aggregation assay (FIG. 1A) for 312 nucleic acid sequences (FIG. 1B). These nucleic acids were nearly all 20 bases in length, single stranded DNA (ssDNA) sequences of random composition. Bulk DNA was used as a positive control. Plotting the percent aggregation for each sequence as shown demonstrates that the holdase activity of the ssDNA is very sequence dependent (FIGS. 1B and 1C). Sequences nearly spanned the complete range in activity, from barely affecting aggregation, to nearly preventing all protein aggregation for over an hour.

Figure 1D:
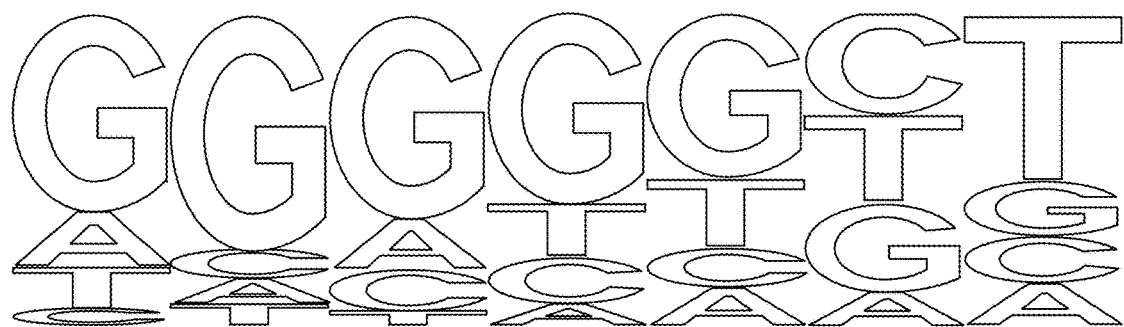

With this high level of sequence dependence, bioinformatics were performed to determine if any sequence motifs encoded holdase activity. Holdase activity was found to be positively correlated with the guanine content in the sequences ($\rho=0.24$, p-value=$1.5\times10^{-5}$). Comparing the top third in holdase activity to the bottom third, only one motif was found to be significantly enriched in sequences with higher holdase activity (53.85% vs 7.69%, FDR=0.001) (FIG. 1D). This motif contained five consecutive guanines followed by any base and then thymine. A similar G-rich motif (consensus pattern: BGGSTGAT) was also found by a regression-based method ($R^2=0.61$, p-value=$1\times10^{-5}$). This analysis suggested that the most potent holdase activity was encoded by a polyG motif.

To verify this polyG motif, another 192 sequences were tested for holdase activity that had high guanine content (FIG. 1C). These sequences included 96 sequences with a 55% bias towards guanine bases, 40 sequences with a 75% bias towards guanine bases, and 56 having different positional variations of the aforementioned polyG motif (FIG. 1D). Comparing the original random sequences to these guanine-rich sequences, the average aggregation was substantially reduced in the enriched guanine set, from 64.8% to 32.0%. Within the enriched guanine set; however, there was still a great deal of variation, with the data spanning aggregation from 72% to 4%. This wide variability suggested that the motif required more than just high guanine content. Within the subset of sequences with a 55% bias towards guanine, a significant polyG motif was again identified by comparing sequences having different holdase activity. Within the subset of 75% guanine-containing sequences, no statistically significant differences were found, as most sequences contained at least one polyG motif. Holdase activity was also tested for 56 sequences having different positional variations of the aforementioned polyG motif, which did not find positional dependency within the sequence for the holdase activity. In the best performing sequences from this enriched assay, the nucleic acid completely prevented protein aggregation for the entire hour and a half experiment. These results suggest that the holdase activity was associated with a polyG motif.

G-Quadruplexes as Potent Holdases

PolyG is well known to form quadruplexes when provided with appropriate counter ions. Composed of polyG bases forming pi-stacked tetrads, guanine quadruplexes are a class of structured nucleic acids that have been of increasing interest due to their regulatory role in replication, transcription, and translation. Quadruplexes have also recently been implicated in several protein aggregation genetic disorders, such as Fragile X syndrome and ALS.

FIGS. 2A-D show the following: Characterization of quadruplex content and holdase activity. Sequences 359, 536, and 576 all displayed holdase activity and contain a polyG motif. Sequence 42 was used as a negative control, as it performed poorly as a holdase chaperone and did not contain a polyG motif. (FIG. 2A) Structural characterization of holdase nucleic acids using circular dichroism in sodium phosphate buffer. Peaks are observed at 260 nm and 210 nm, as well as a trough at 245 nm, indicating the presence of parallel G-quadruplexes. Thermal stability of quadruplexes shown in FIG. 3 in potassium phosphate buffer. (FIG. 2B) NMM fluorescence measured at 610 nm. (FIG. 2C) Citrate Synthase aggregation during chemically induced denaturation via right angle light scattering at 360 nm. (FIG. 2D) Holdase activity towards citrate synthase of ssDNA compared to its duplexed counterpart.

Figure 3:
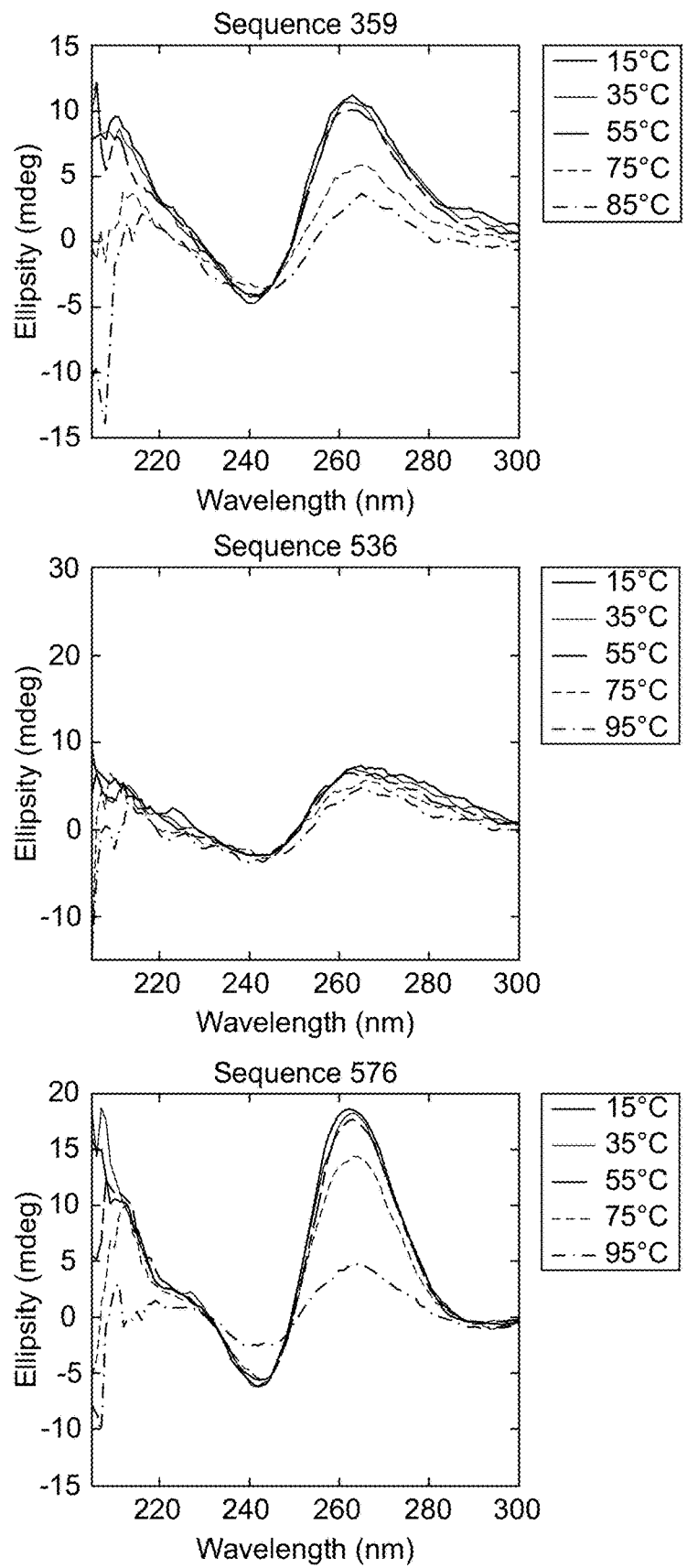
FIG. 3 illustrates exemplary experimental CD spectroscopy results investigating the thermal stability of quadruplex-containing sequences (including Seq359 (SEQ ID NO:1), Seq536 (SEQ ID NO:2), and Seq576 (SEQ ID NO:3)), in accordance with one or more embodiments.
Figures 4A, 4B, 4C:
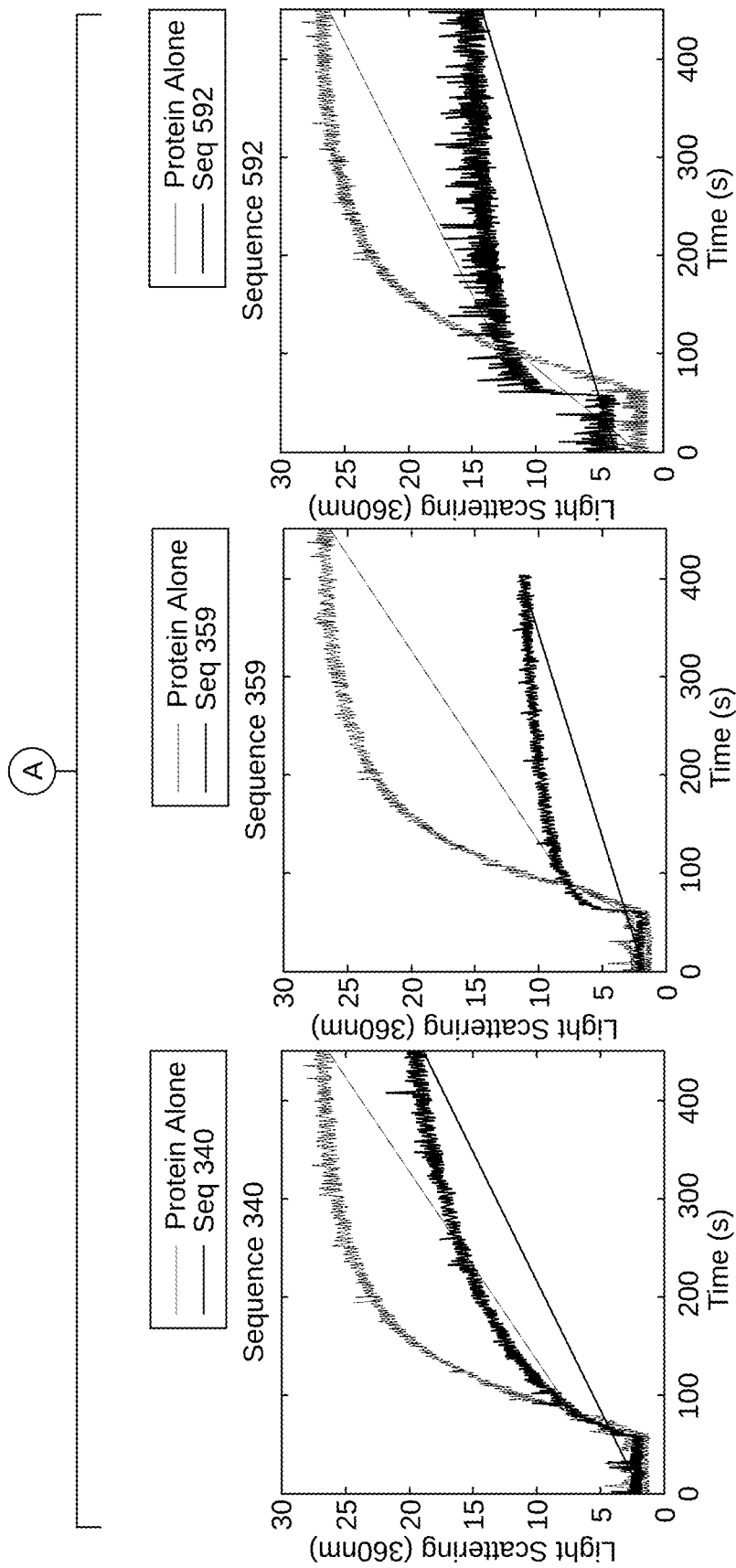
FIGS. 4A-4I illustrate exemplary results of exemplary chemical aggregation tests of multiple quadruplex-containing sequences with citrate synthase (including Seq340 (SEQ ID NO:26), Seq359 (SEQ ID NO:1), Seq592 (SEQ ID NO:13), Seq589 (SEQ ID NO:27), Seq536 (SEQ ID NO:2), Seq573 (SEQ ID NO:8), Seq576 (SEQ ID NO:3), Seq580 (SEQ ID NO:28), and Seq583 (SEQ ID NO:4)), in accordance with one or more embodiments.
Figures 4D, 4E, 4F:
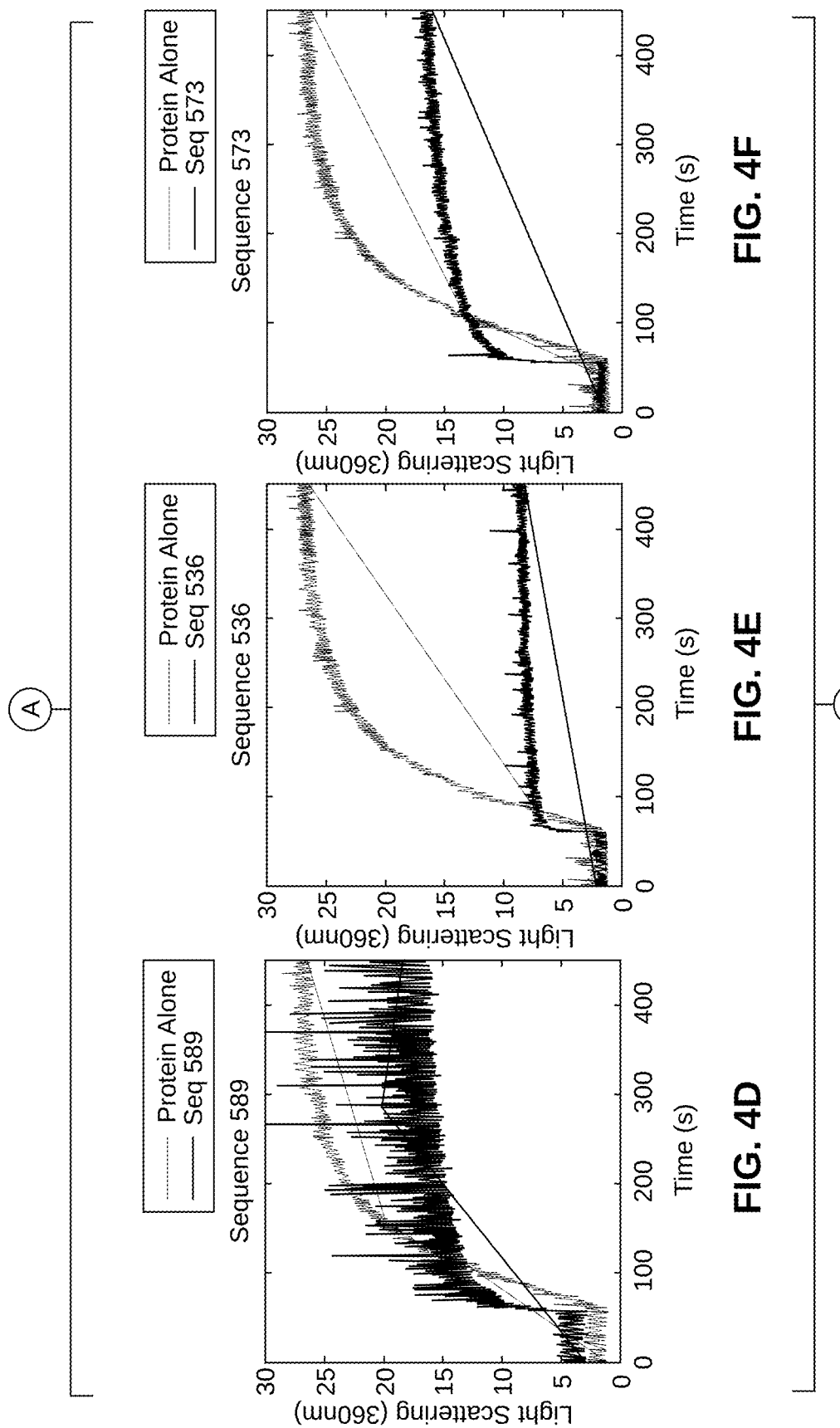
Figures 4G, 4H, 4I:
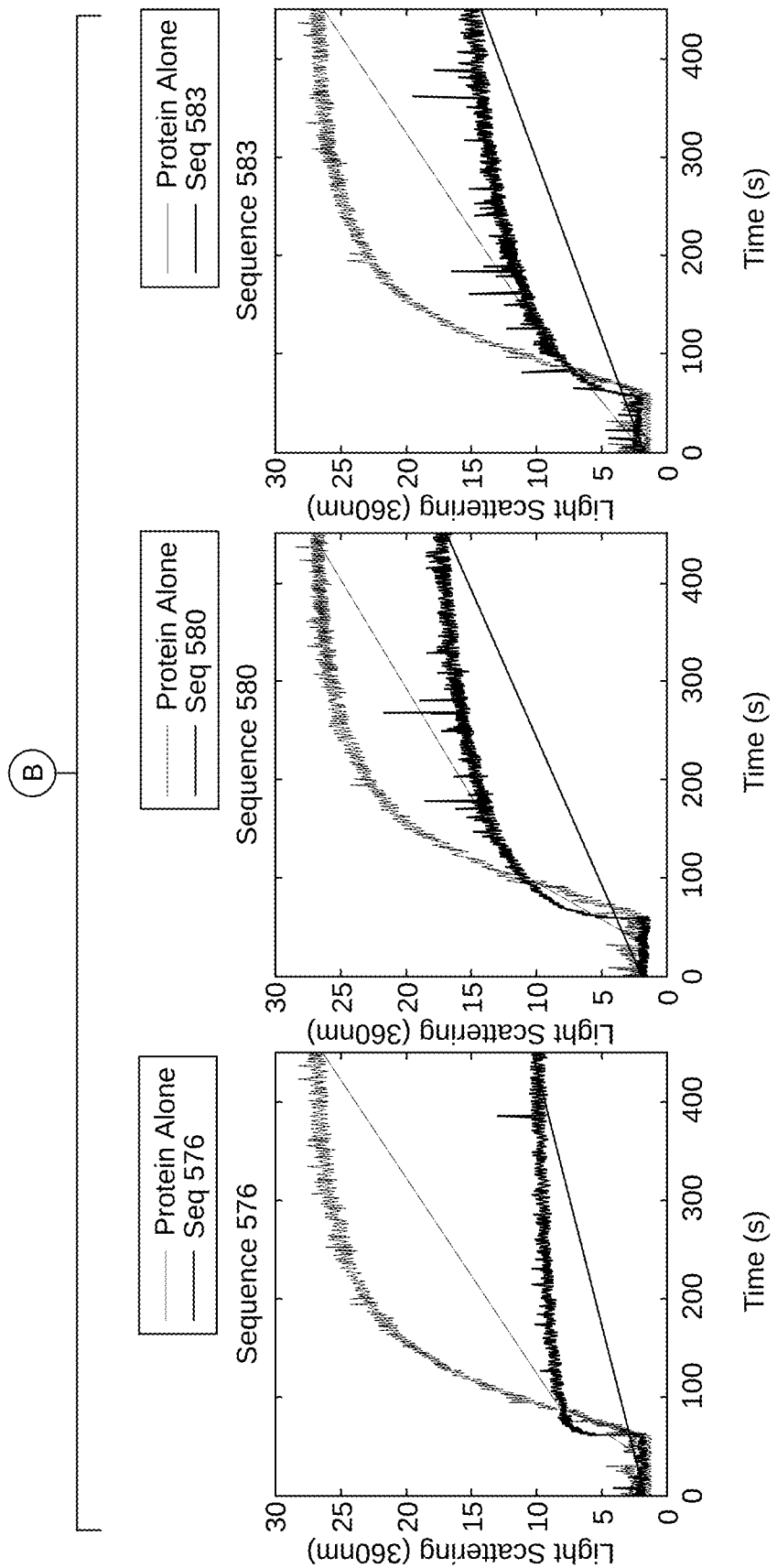

FIG. 3 shows the following: Examples of experimental results investigating the thermal stability of quadruplex-containing sequences as measured by CD spectroscopy. Each line represents a wavelength scan at the indicated temperature.

Figure 2A:
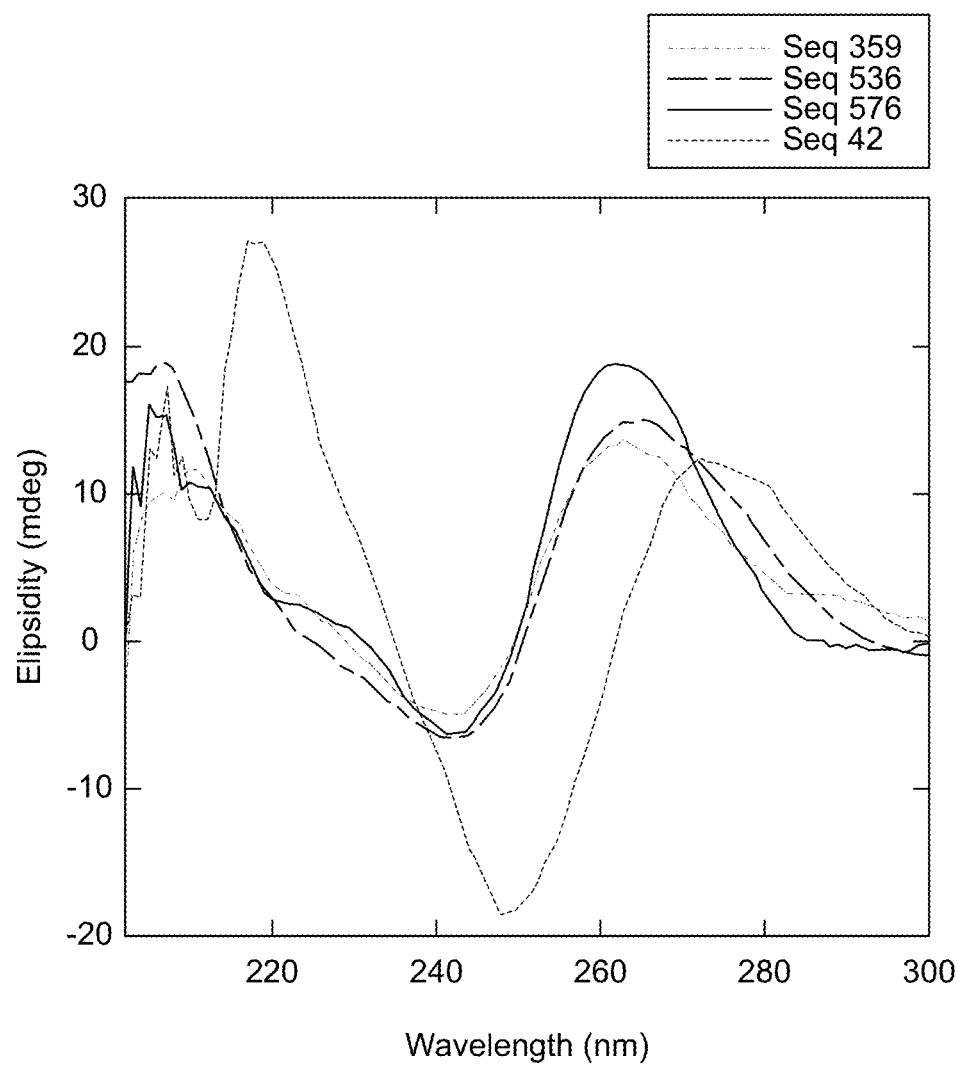
Figure 2B:
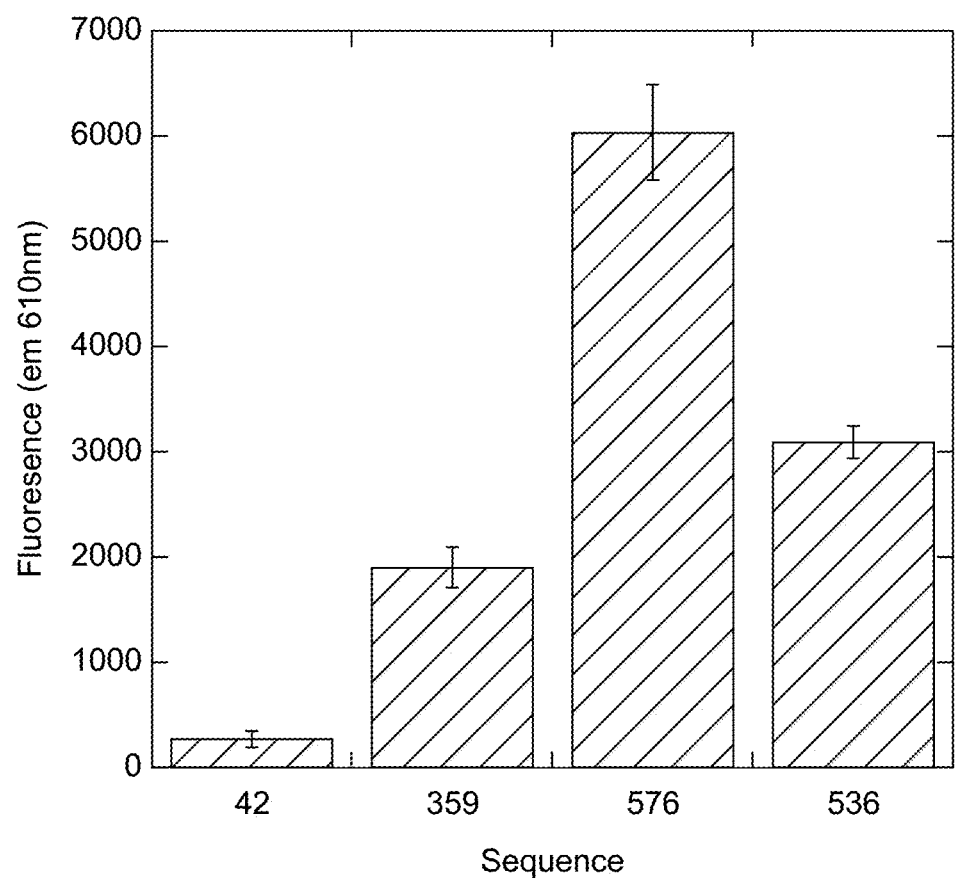
Figure 2C:
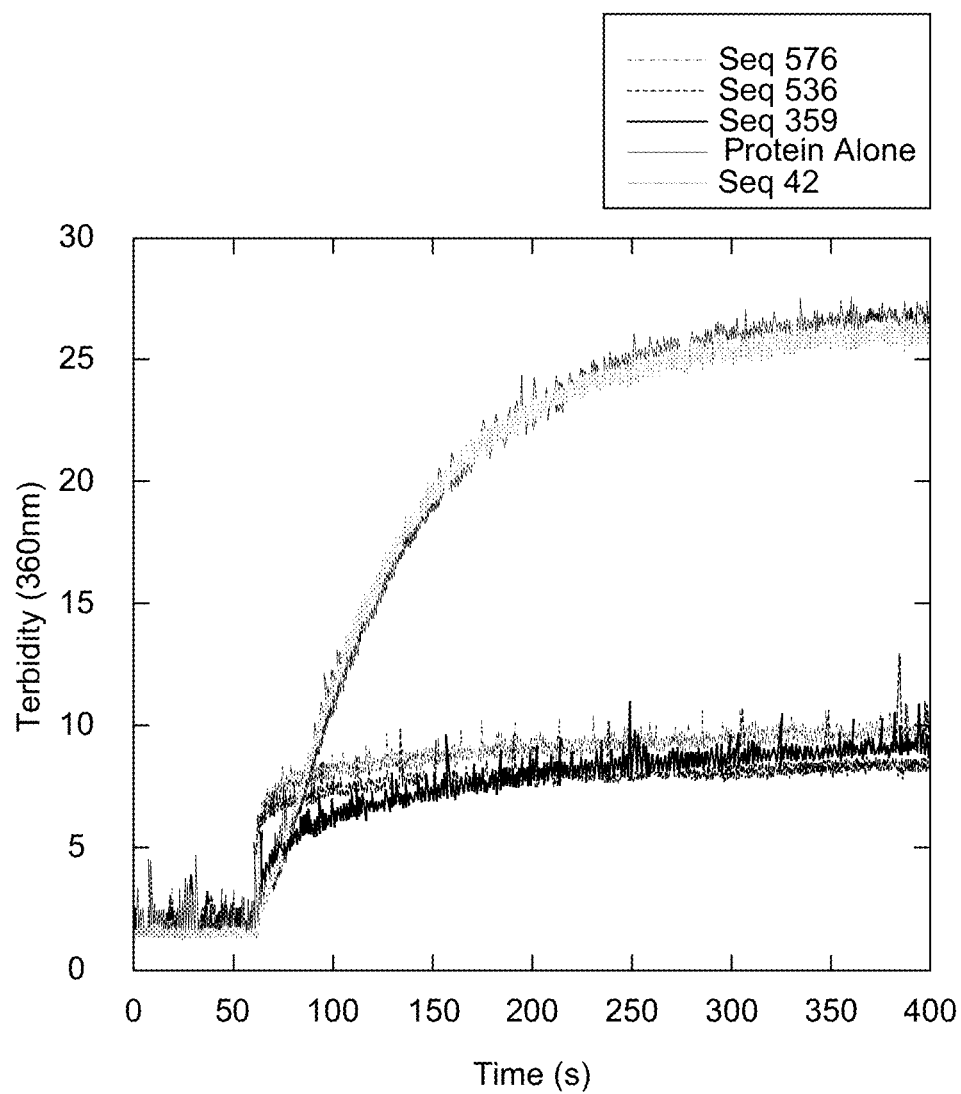

To test if the sequences containing polyG that had potent holdase activity were forming quadruplexes, circular dichroism (CD) spectroscopy experiments were performed on three sequences (sequences 359, 536, and 576) to determine their secondary structure, as shown in FIG. 2A, with a fourth sequence (sequence 42) being used as a negative control, and the resulting CD spectra were indicative of parallel quadruplex formation in the three sequences and no quadruplex formation in the fourth, negative control, sequence. This supposition was further supported by examining the emission spectra of N-methylmesoporphyrin IX (NMM), a well characterized parallel quadruplex binding fluorophore. The fluorescence spectra of NMM was examined in the presence of 1 µM DNA, which was the same concentration used in the holdase assays. The NMM spectra indicated that all three sequences formed parallel quadruplexes at the concentration used in aggregation assays, unlike the ssDNA control, as shown in FIG. 2B. CD melting experiments indicated that these quadruplex structures were stable, with >90% of the quadruplex structures remaining at 45° C. for sequences 536 and 576 and 70% for sequence 359 (FIG. 3 shows exemplary results of such thermal stability experiments).

Further investigation was done to determine whether RNA versions of these sequences would also form quadruplexes. For sequences 536 and 576, the conformation was shown to be similar for both DNA and RNA, with all spectra indicating parallel quadruplex formation. However, for sequence 359, the type and stability of quadruplex conformation was shown to depend on the type of nucleic acid present. The DNA version at 45° C. had spectra showing a mixture of parallel and anti-parallel quadruplex. The RNA version appeared to be more stable, with 80% of the original quadruplex structure remaining at 45° C. Furthermore, the spectra indicate that only the parallel quadruplex is formed in the case of sequence 359 RNA. The change in structure for 359 from a mixed topology to parallel merited separate testing of its chaperone activity. Heat denaturation assays demonstrated that the RNA version also had potent chaperone activity, preventing aggregation even more than its DNA counterpart.

These experiments confirmed that the holdase activity of these polyG-containing sequences were associated with quadruplex structure. Re-analyzing the heat denaturation aggregation assay data, of the 160 sequences tested that had the sequence properties to form quadruplexes, 133 appeared in the top third of data, making up 79% of the sequences in that subset. 152 of the 160 quadruplex sequences also decreased aggregation by at least 50%.

FIGS. 4A-4I show the following: Representative examples of the results of chemical aggregation tests of multiple quadruplex-containing sequences with citrate synthase. Light scattering was measured at 360 nm. Concentration ratio is 1:2 protein to DNA strand.

The holdase activity of the quadruplex-forming sequences was further characterized using chemical denaturation aggregation assays in which the protein starts in a denatured state, such as in the FIGS. 4A-4I examples. Light scattering experiments confirmed the holdase activity in at least nine different quadruplex sequences (FIG. 2C, FIGS. 4A-4I, and Table 1). This data also suggests that the quadruplexes are binding a misfolded or partially denatured form of the protein rather than the native state.

Figure 2D:
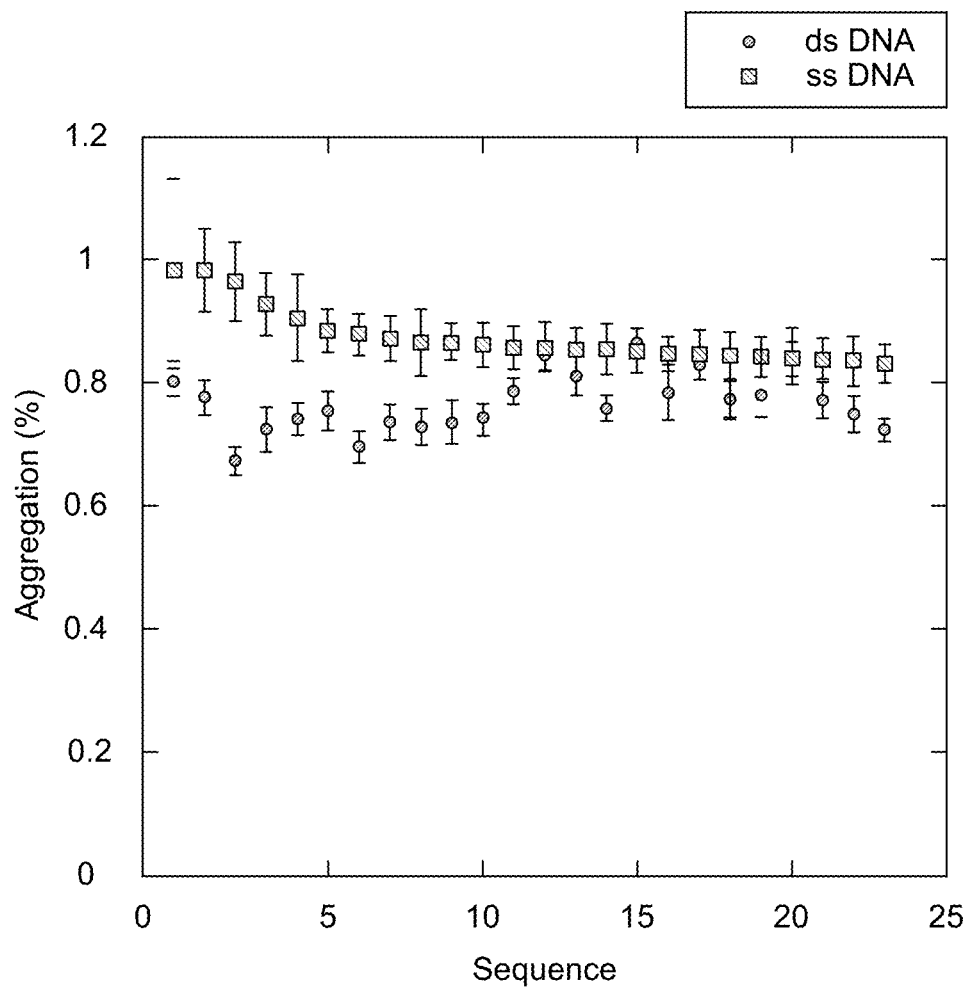

The higher level of activity from quadruplex DNA raised the question of whether any structured DNA could have a similar effect. In other words, could the activity arise from any DNA with greater structure than ssDNA? To test this possibility, the holdase activity of 24 duplexed sequences was tested to compare directly with their single-stranded counterparts. Overall, the differences were small, and in many cases statistically insignificant (FIG. 2D). These experiments suggest that the holdase activity displayed could be specific to quadruplex structures, and not to other structured DNAs.

Generality of Holdase Activity

Figure 5E:
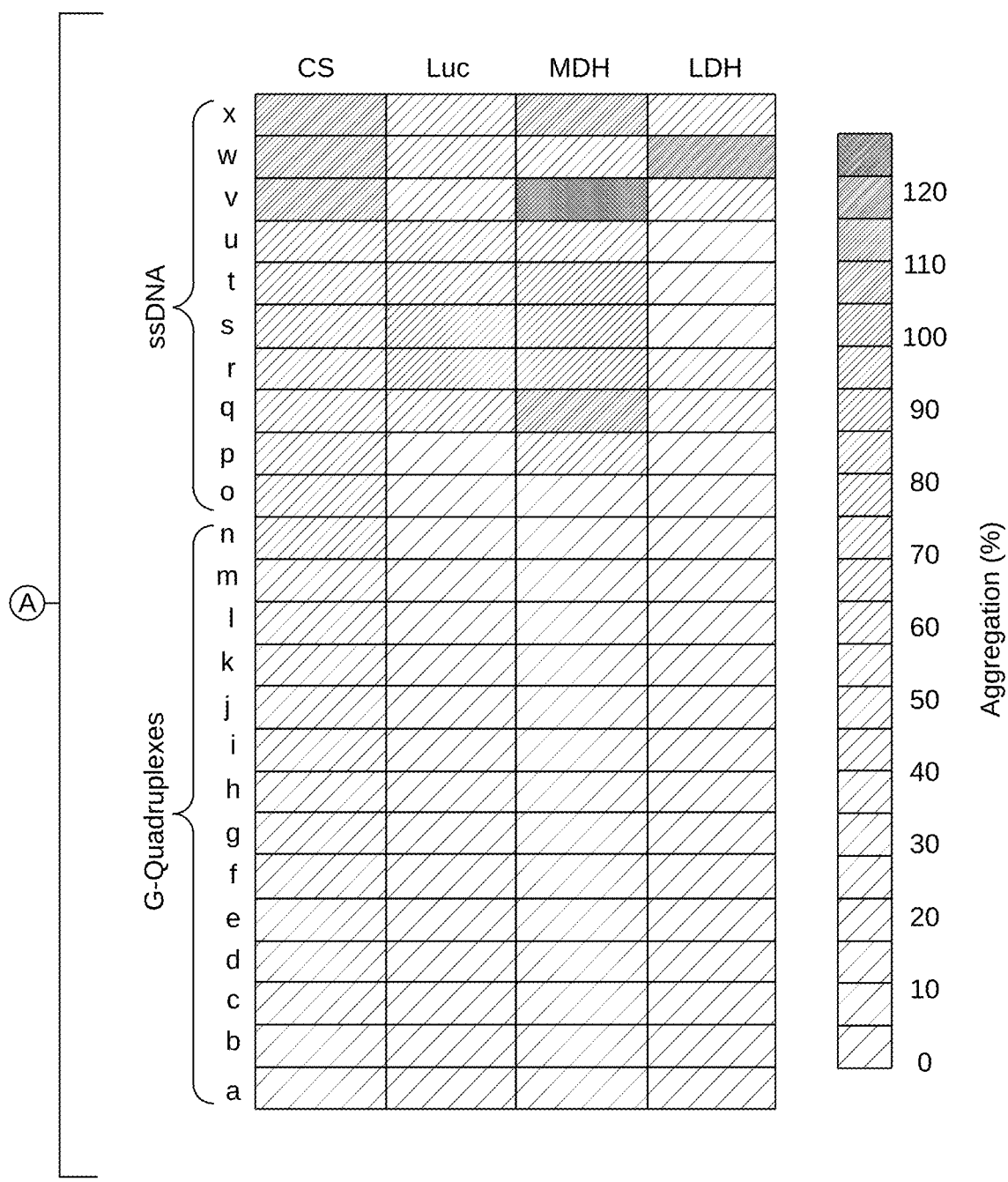

FIGS. 5A-5E show the following: FIGS. 5A-5D show experimental results regarding the generality of G-quadruplex holdase activity using four different proteins: Luciferase (Luc), Citrate Synthase (CS), L-Malate Dehydrogenase (MDH), and L-Lactate Dehydrogenase (LDH). Boxed are the 14 sequences with the propensity to form quadruplexes, while the remaining 10 sequences are non-structured ssDNA (left). This data is also shown as a heat map (FIG. 5E).

To determine the generality of quadruplex holdase activity, aggregation assays were performed with three other proteins (Luc, LDH, and MDH) in addition to CS. To check whether this holdase activity was quadruplex-specific with multiple proteins, 14 quadruplex sequences and 10 single-stranded sequences were tested with each protein (see Table 1). The proteins used have varying structural properties, ranging in pI from 6.1 to 8.5, and size from 62.9 kD to 140 kD. With all four proteins, the quadruplex sequences severely decreased protein aggregation, demonstrating strong holdase activity. For Luc, LDH, and MDH, most of the quadruplex sequences tested were able to completely prevent protein aggregation. However, the single-stranded sequences demonstrated little to no activity for all of these proteins, as shown in FIGS. 5A-5E. These data strongly suggest that the holdase activity displayed by quadruplex sequences is general, while also unique to quadruplex-forming sequences. Of note, LDH is the only of these proteins with previously characterized DNA-binding activity towards both duplex and ssDNA, but its aggregation was only significantly reduced by binding to quadruplex sequences. Also of note, two sequences (O and P) not predicted as having high quadruplex probability but showing significant holdase activity, do have substantial guanine content and could potentially still form quadruplexes despite being listed as ssDNA.

Chaperone Activity in *Escherichia coli*

With the newfound quadruplex-containing sequences possessing powerful holdase activity in vitro, testing was conducted to determine whether they would have chaperone-like activity in a cellular system. In these experiments, assays were used to determine the ability of these quadruplex-containing nucleic acids to improve the folding of fluorescent proteins in *E. coli*.

Green fluorescent protein's (GFP) fluorescence is dependent almost solely on its folding to its native state, which allows self-catalyzed chromophore formation, and continued maintenance of the native state causes continued fluorescence. Furthermore, although many variants of GFP were later engineered to have fast maturation times and high stability, wildtype GFP (wtGFP) folds slowly and poorly in *E. coli*, thereby producing little fluorescence. These properties previously enabled directed evolution of chaperones in *E. coli* to improve chaperone activity and therefore increase wtGFP fluorescence brightness. Similarly, wtGFP fluorescence can be used to monitor the protein folding stress level in *E. coli*. Of importance, the underlying reason why expressing proteins with GFP fusions in *E. coli* increase their overall folding levels is due to productive folding interactions between the GFP and known chaperones. The experiments of the present disclosure have confirmed the previous findings that co-expressing known chaperones increases the fluorescence (and therefore the folded protein) of wtGFP in *E. coli* (see FIG. 16G).

However, a major barrier existed to using wtGFP to examine chaperone nucleic acid activity. Bulk nucleic acids may have little to no effect on GFP folding or aggregation. This lack of effect likely stems from electrostatic inhibition, as wtGFP is quite acidic (pI=5.67), and would likely be repelled by the negative charge of the nucleic acids' phosphate backbone. However, there are now many other GFP-like variants with differing sequence properties.

TagRFP675 was especially attractive due to its combination of its basicity (pI=8.53), relatively long maturation time that would make it susceptible to aggregation or degradation, and long wavelength to allow easy detection. Testing the same set of chaperones as wtGFP with TagRFP675 demonstrated that like wtGFP, the amount of folded TagRFP675 is considerably higher in *E. coli* co-expressing many known chaperones (compared to the empty vector control) (see FIGS. 16A-G). Notably, the only known chaperone tested to not cause an increase in the fluorescence in the TagRFP675 was Hsp33 (see FIG. 16E), which is activated specifically by oxidative stress, and would not be expected to be active under the test conditions.

The fluorescence of TagRFP675 was compared when co-expressed under heat stress with three of the best-characterized quadruplex-containing nucleic acids from the experiments above (sequences 359, 536, and 576). As controls, the experiment compared both against empty vector, as well as sequence 42, which displayed little to no in vitro activity. Expressing the quadruplex-containing or control sequences did not significantly affect *E. coli* growth rate. Unlike the above in vitro testing, in this experiment, the quadruplex-containing sequences were expressed as RNA from a pBAD33 plasmid modified for small RNA expression. Notably, this plasmid does not contain a ribosome-binding site, and so little translation of these RNAs is expected.

Figure 16A:
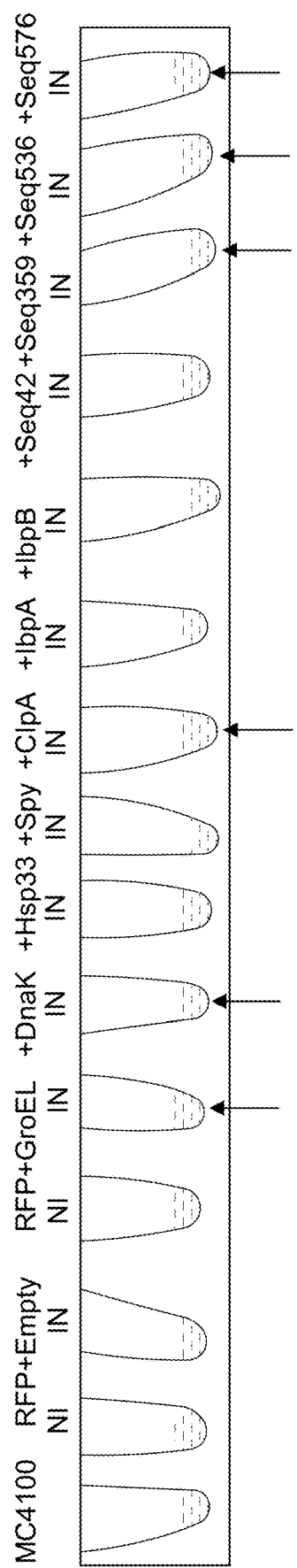
Figure 16C:
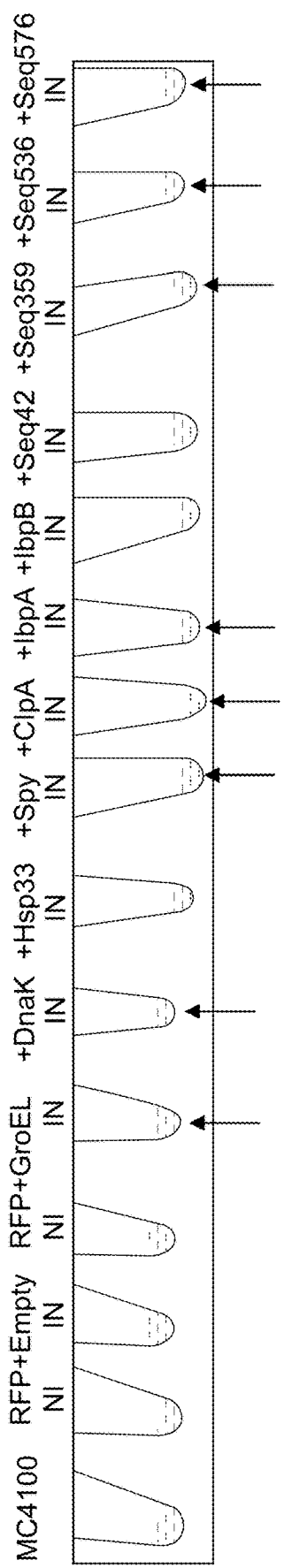
Figure 16E:
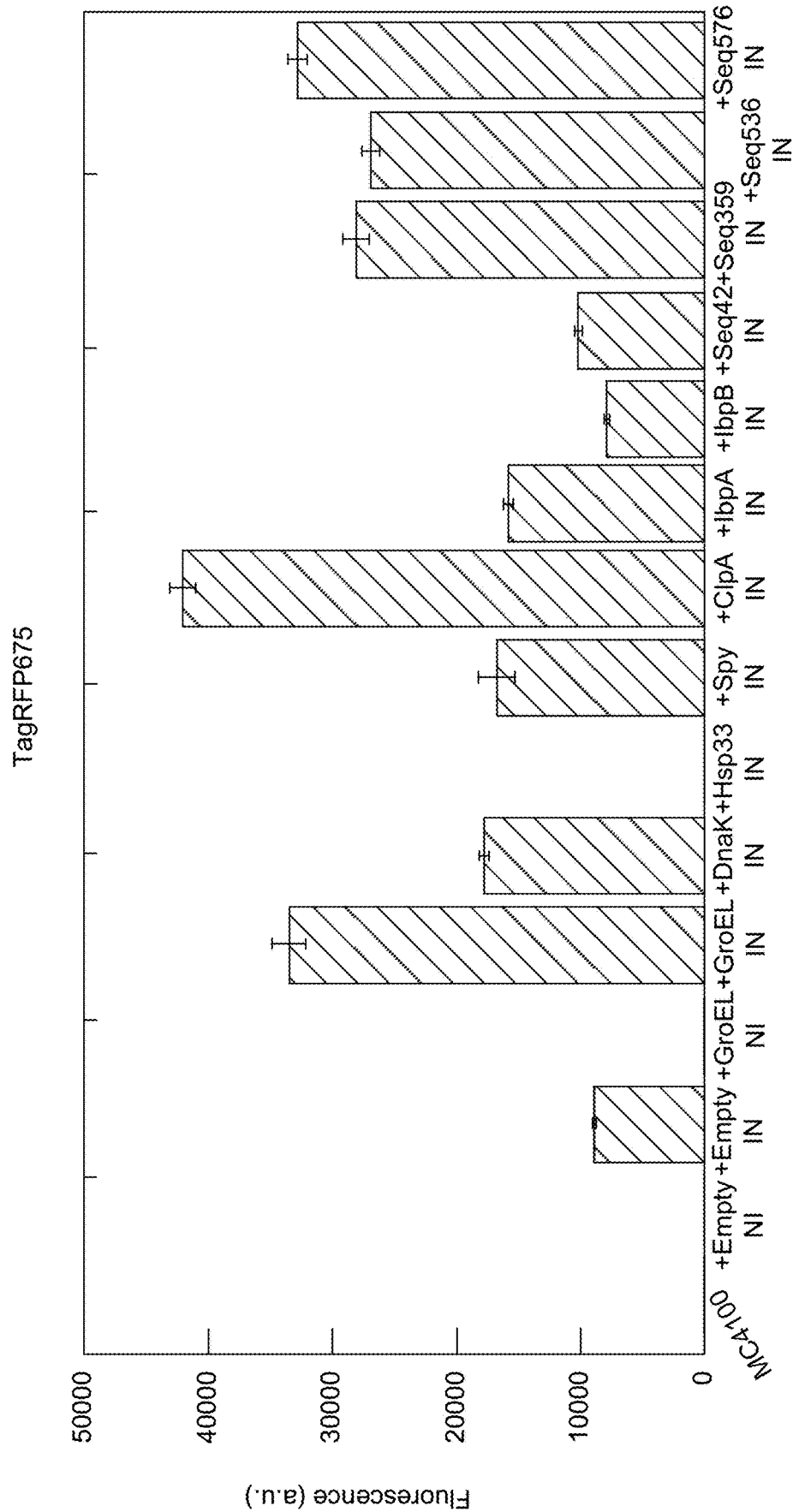

Testing the fluorescence of TagRFP675 in each of these cases demonstrated that there is considerably higher fluorescence in cells co-expressing the quadruplex-containing sequences than either the empty vector or Seq42 (SEQ ID NO:4), indicating a higher level of properly folded TagRFP675; the effects of the quadruplex-containing sequences were greater than that of several known chaperones, including DnaK, Hsp33, IbpA, and IbpB (see FIG. 16E). As a control, the acidic wtGFP was also tested and was less affected by the quadruplex-containing sequences (see FIG. 16G). These experiments show that the chaperone nucleic acids found in vitro are also able to improve the folding of a fluorescence protein that usually struggles to stably fold in *E. coli*. Of note, only three of the quadruplex-containing sequences chosen from the above in vitro screening experiments were tested, and all three have shown chaperone-like effects. The three chaperone sequences used in this test ranked 1st, 18th, and 52nd in the initial screen experiment; based on this ranking it is also expected that dozens more sequences from the initial screen may potentially display chaperone activity in *E. coli*.

Holdase Activity Due to Oligomerization

Figure 6A:
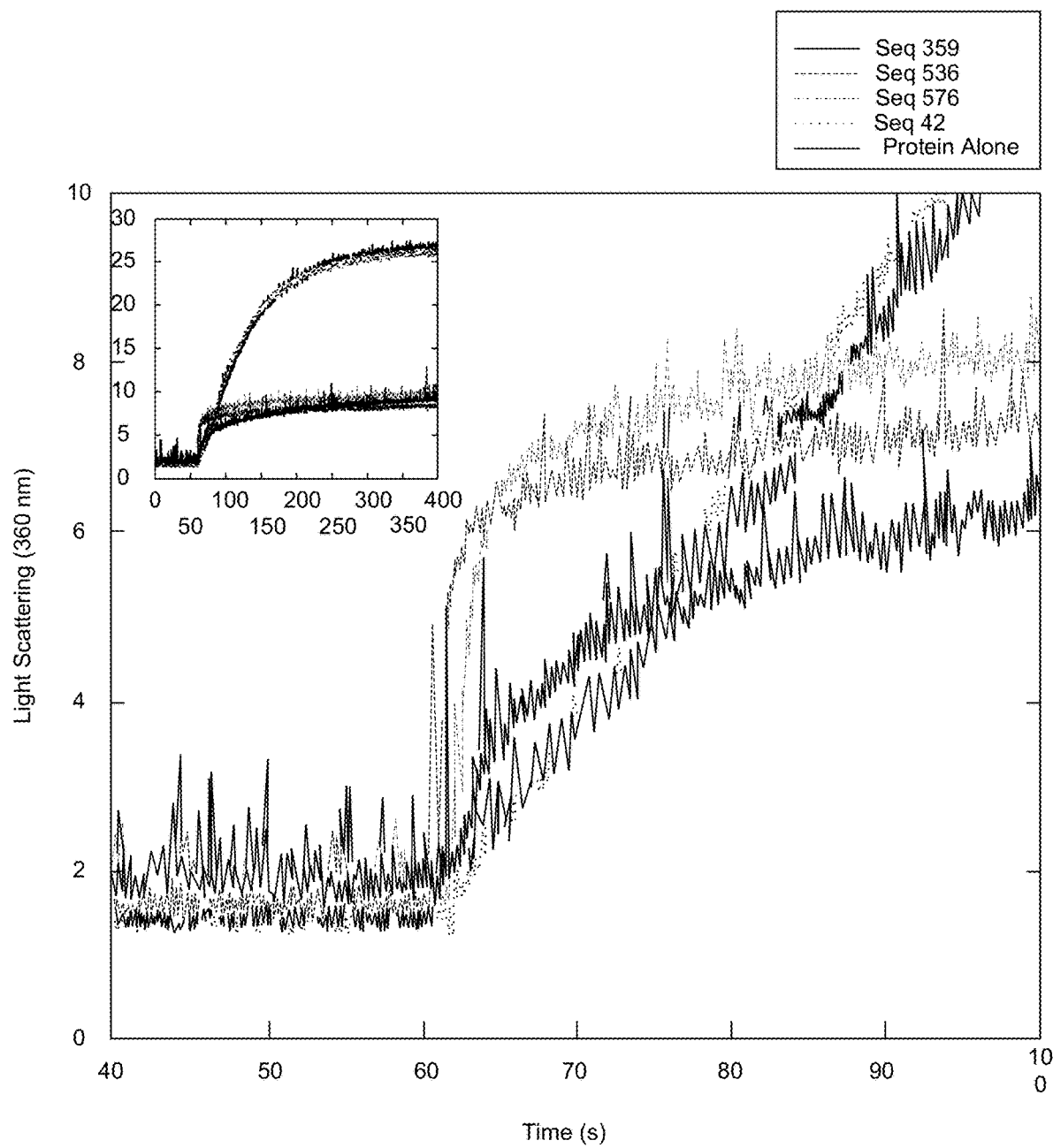
Figure 6B:
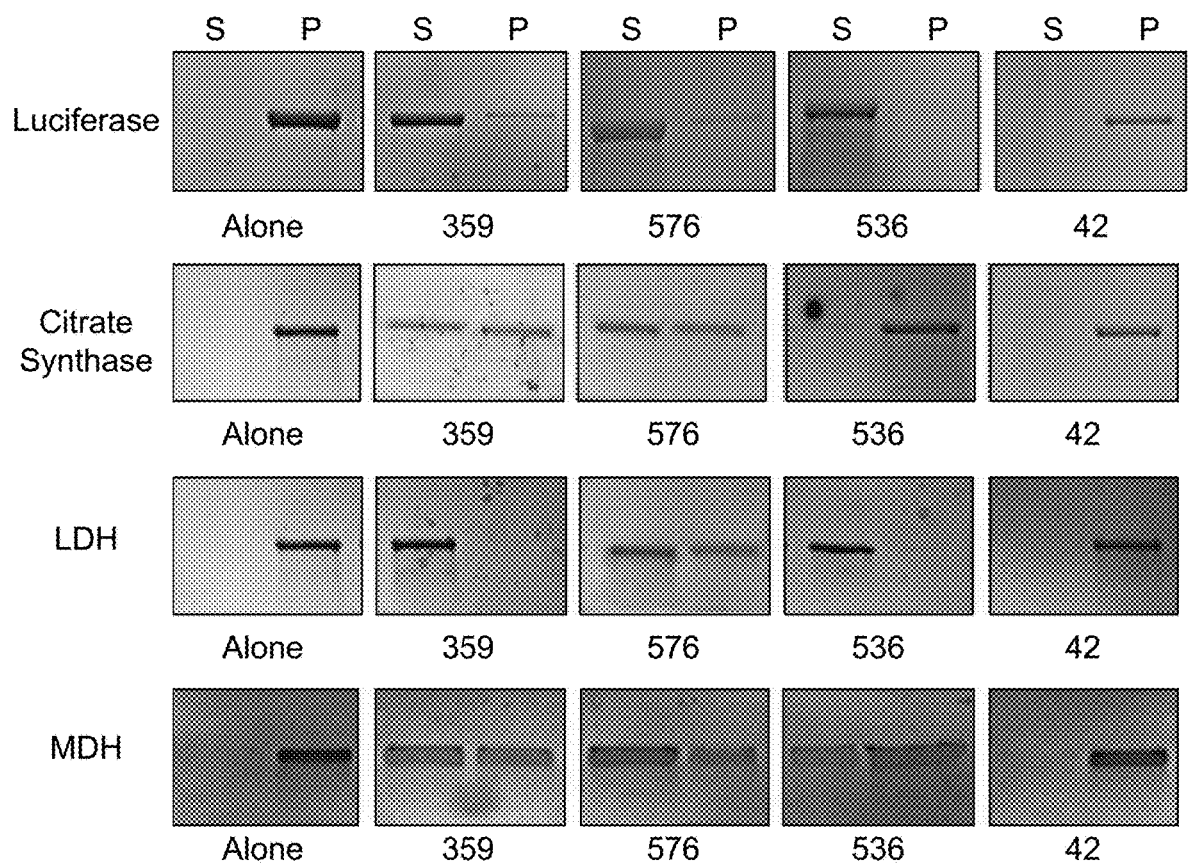
Figure 6C:
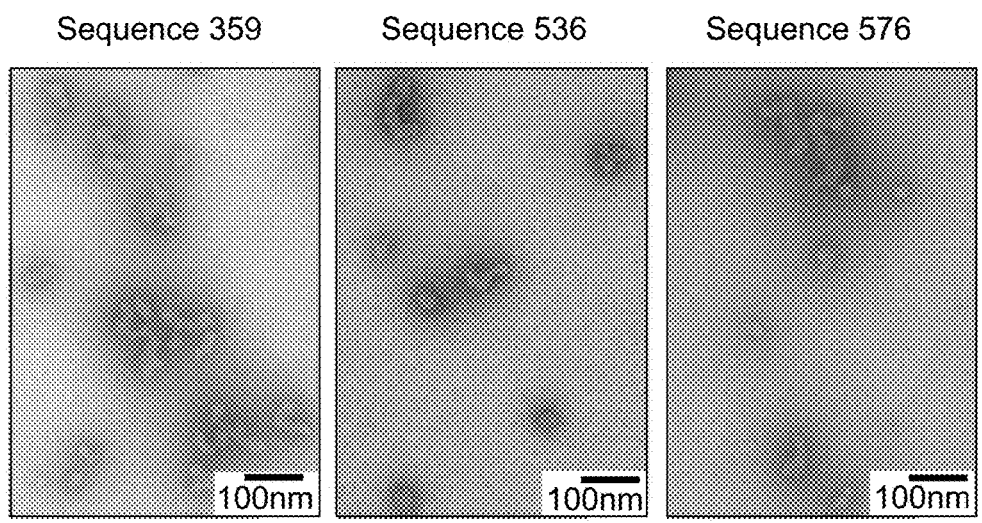

FIGS. 6A-C show the following: Experimental results of quadruplex-containing sequences promoting oligomerization. Sequences 359, 536, and 576 all displayed holdase activity and contain a polyG motif. Sequence 42 was used as a negative control, as it performed poorly as a holdase chaperone and did not contain a polyG motif. (FIG. 6A) Right angle light scattering of chemically induced aggregation of citrate synthase. Initial kinetics of aggregation shown with full time scale as the top-left insert. (FIG. 6B) Spin down assay with four different proteins denatured at 60° C. in the presence of DNA. S represents the soluble fraction, while P represents the insoluble fraction or pellet. (FIG. 6C) Transmission electron microscopy negative stain images of soluble fractions from chemically induced aggregation spin down assays. Citrate synthase oligomers were observed in each of the quadruplex cases, although the morphology of the quadruplex was dependent on the DNA sequence.

While analyzing the light scattering data from chemically denatured citrate synthase in the presence of quadruplexes, it was observed that although the total light scattering was greatly decreased by the presence of the quadruplexes, the quadruplexes caused a small initial jump in light scattering (FIG. 6A). These data are highly reminiscent of a pattern observed recently in which nucleic acids could prevent protein aggregation by promoting protein:nucleic acid oligomerization.

To determine whether the tested quadruplexes were acting in a similar manner, additional spin-down assays, CD, and transmission electron microscopy (TEM) experiments were performed. Spin-down assays were performed by heating citrate synthase, luciferase, MDH, or LDH with quadruplexes to 60° C. for 15 min, and then returning them to room temperature. The samples were centrifuged to then separate soluble and pellet fractions. SDS-PAGE gels demonstrated that the quadruplexes kept the proteins soluble even at extreme temperatures, as shown in FIG. 6B, similar to previously characterized oligomerization cases. Of note, a control single stranded sequence of the same length (sequence 42) did not keep the proteins soluble under these conditions, even for the well-characterized DNA binding protein LDH (FIG. 6B). Measuring CD spectra of luciferase protein as a function of temperature in the presence of quadruplexes showed that the protein maintained partial β-sheet structure as high as 80° C., and that this non-native structure was retained upon return to room temperature, similar to previous oligomerization cases. Furthermore, negative stain TEM imaging showed that the quadruplexes caused the formation of protein oligomers, such as shown in FIG. 6C. Notably, the morphology of the oligomers varied with different quadruplex structures, suggesting that the sequence or structural details of the quadruplex influence the structure of the subsequent oligomerization that occurs. Further spin-down assays in chemically denaturing conditions, such as the exemplary assay of FIG. 7, suggest that these oligomers tend to not form large aggregates.

Figure 7:
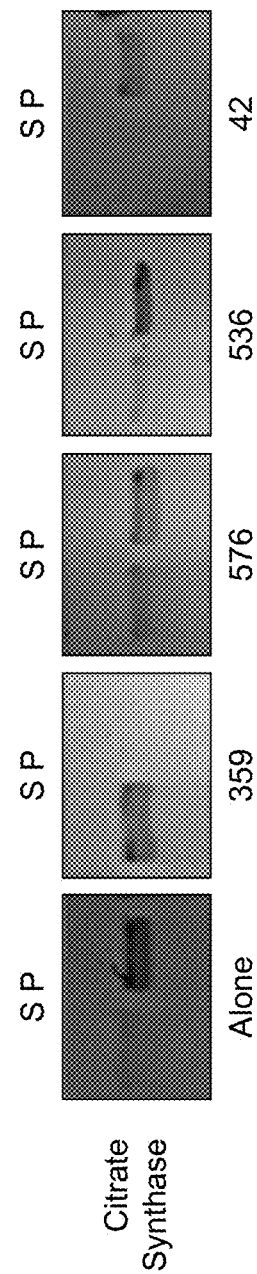
FIG. 7 illustrates exemplary results of an exemplary chemical spin down assay using citrate synthase demonstrating prevention of protein aggregation (including Seq359 (SEQ ID NO:1), Seq536 (SEQ ID NO:2), Seq576 (SEQ ID NO:3), and Seq42 (SEQ ID NO:4)), in accordance with one or more embodiments.

FIG. 7 shows the following: An example of prevention of protein aggregation in a chemical spin down assay using citrate synthase. Sequences 359, 536, and 576 all displayed holdase activity and contain a polyG motif. Sequence 42 was used as a negative control, as it performed poorly as a holdase chaperone and did not contain a polyG motif.

Figure 8:
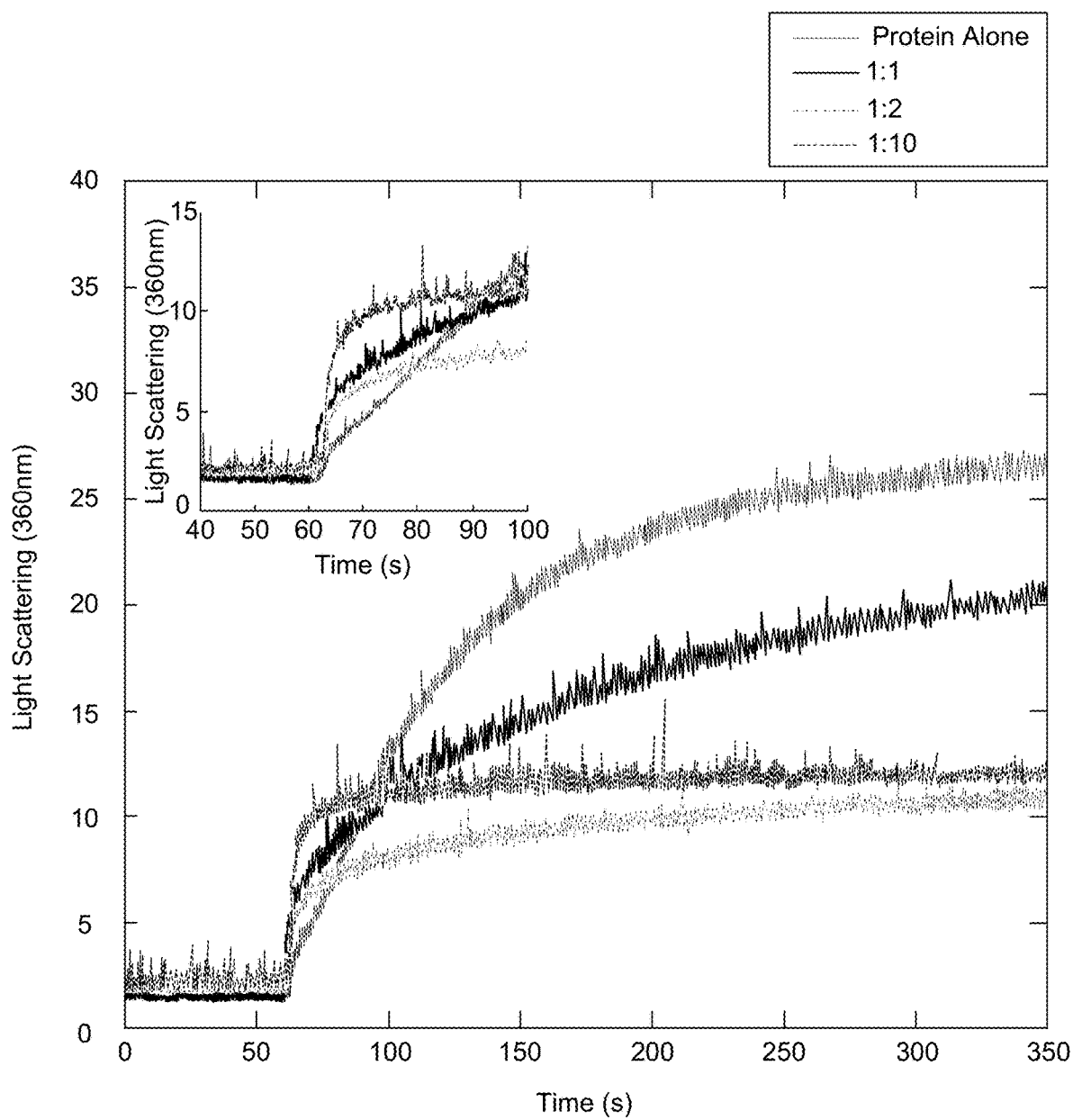
FIG. 8 illustrates exemplary results from an exemplary chemical aggregation test of the concentration dependence of holdase activity of sequence 359 (SEQ ID NO:1), in accordance with one or more embodiments.

Additional chemical aggregation tests showed variations in holdase activity of the quadruplex-containing sequences based on sequence and protein concentration, such as in FIG. 8.

FIG. 8 shows the following: Example of results from a chemical aggregation test of the concentration dependence of holdase activity of sequence 359, one of the best-performing holdase sequences in the experiments, showing a strong concentration dependence in holdase activity. Citrate Synthase aggregation from chemically induced denaturation via right angle light scattering at 360 nm is shown. Concentration ratios are citrate synthase:DNA strand.

Preventing Aggregation of Monoclonal IgG Antibodies

Figure 9A:
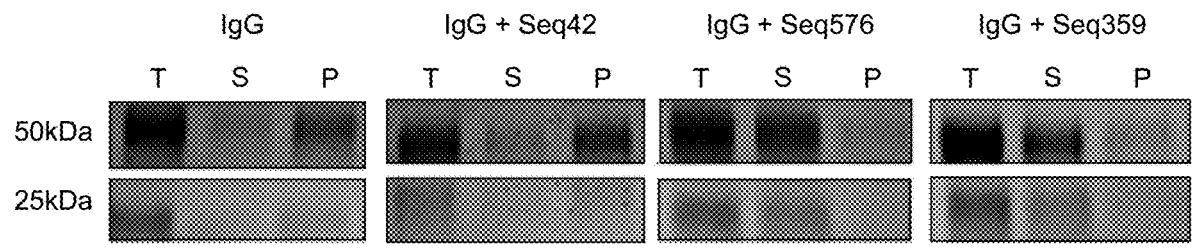

Additional tests were conducted to determine whether nucleic acids could be used to prevent the aggregation of monoclonal IgG antibodies, as antibodies are now commonly used drugs, but often have aggregation problems. Therefore, thermal aggregation experiments were performed using two of the best characterized quadruplex-containing chaperone nucleic acids from the disclosed exemplary experiments, Seq359 (SEQ ID NO:1) and Seq576 (SEQ ID NO:3), to test whether they could prevent IgG aggregation. Briefly, the experiments were performed as described herein for spin-down assays, with the exception that the IgG was at 1.3 µM concentration in a 1:1 ratio with the nucleic acid strand, heated at 75° C. for 15 minutes while shaking at 350 rpm in 10 mM potassium phosphate buffer at pH 7.0. Seq42 (SEQ ID NO:4), which showed no significant chaperone activity in experiments discussed herein, was used as a negative control. The results of such experiments, as shown in FIG. 9A, showed that both Seq576 (SEQ ID NO:3) and Seq359 (SEQ ID NO:1) prevented the aggregation of IgG under these conditions. In the FIG. 9A experimental spin down assay results, T represents the total fraction, S represents the soluble fraction, while P represents the insoluble fraction or pellet. Seq576 (SEQ ID NO:3) and Seq359 (SEQ ID NO:1) showed greater content within the soluble fraction, rather than the pellet, suggesting reduced aggregation of IgG.

Figure 9B:
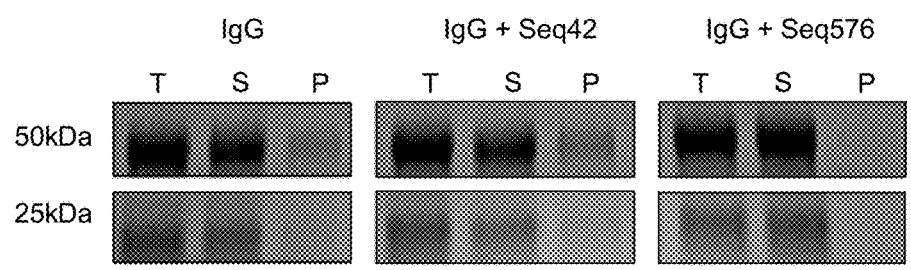

Because agitation such as that experienced by solutions during shipping and handling can cause protein aggregation, experiments were conducted to determine whether the sequences could prevent aggregation caused primarily by agitation. Therefore, a second set of experiments were performed where the temperature of the assay was decreased to 65° C., and then shaken at 1200 rpm for 72 hours in the presence of DNA in a 10:1 ratio, at a concentration of 3.3 µM IgG. As shown in the FIG. 9B experimental spin down assay results, the inclusion of Seq576 (SEQ ID NO:3) also led to a decrease in IgG aggregation in this case.

Improving Chaperone Activity

Figure 10:
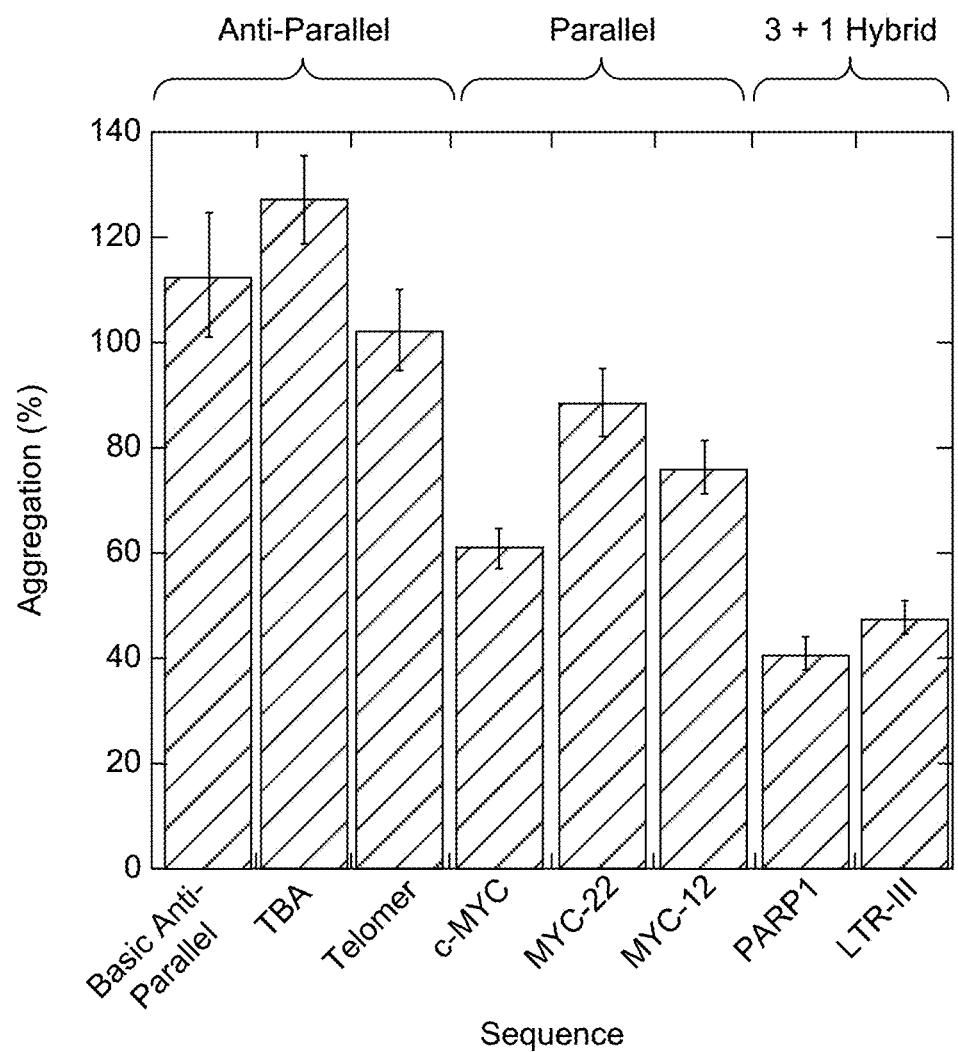
FIG. 10 illustrates exemplary results of an exemplary heat denaturation aggregation experiment comprising quadruplex-containing nucleic acid sequences of varying topology (including Basic Anti-Parallel (SEQ ID NO:30), TBA (SEQ ID NO:31), Telomer (SEQ ID NO:32), c-MYC (SEQ ID NO:33), MYC22 (SEQ ID NO:34), MYC12 (SEQ ID NO:35), PARP1 (SEQ ID NO:36), and LTRIII (SEQ ID NO:37)), in accordance with one or more embodiments.

Some of the experiments described above found that quadruplex containing sequences can be powerful aggregation-prevention protein chaperones. However, it could be useful to vary nucleic acid sequences to continue to improve and tune chaperone activity. To determine whether different forms of quadruplex structures potentially have different intrinsic aggregation or chaperone activity tendencies, sequences were chosen that had previously determined quadruplex structures and that were ~20 bases in length, and the sequences were subjected to a heat denaturation aggregation experiment, as described above. The different sequences displayed varying activities that appeared to correlate with structural properties. As shown in the experimental results illustrated in FIG. 10, which compare holdase activity of different quadruplex-containing sequences of known topology, anti-parallel quadruplexes appeared to have no chaperone activity or appeared to increase protein aggregation; parallel quadruplexes showed minor chaperone activity; 3+1 mixed quadruplexes displayed greater chaperone activity. These results suggest that the topology of a quadruplex matters in its chaperone function, along with adjacent sequences.

Given LTRIII's (SEQ ID NO:37) demonstrated medium level of chaperone activity, a series of mutations were designed to test if its activity could be improved.

Briefly, assays were performed as the citrate synthase plate reader turbidity assays were described herein, with minor modifications: for the thermal aggregation assays, LTRIII (SEQ ID NO:37) and its variants were incubated with 550 nM Citrate Synthase from porcine heart in a 1:2 protein:DNA strand concentration. Aggregation was measured at an absorbance at 360 nm in a multimode plate reader, using black clear flat bottom half-area plates, with shaking and measurements every 36 s. In each of these assays, the plates were transferred from ice to a preheated 50° C. plate reader, and the temperature was held constant throughout the entire experiment. Each plate was run for 1.5 h in 10 mM potassium phosphate, pH 7.5 buffer. The sequences were run in triplicate.

Figure 11:
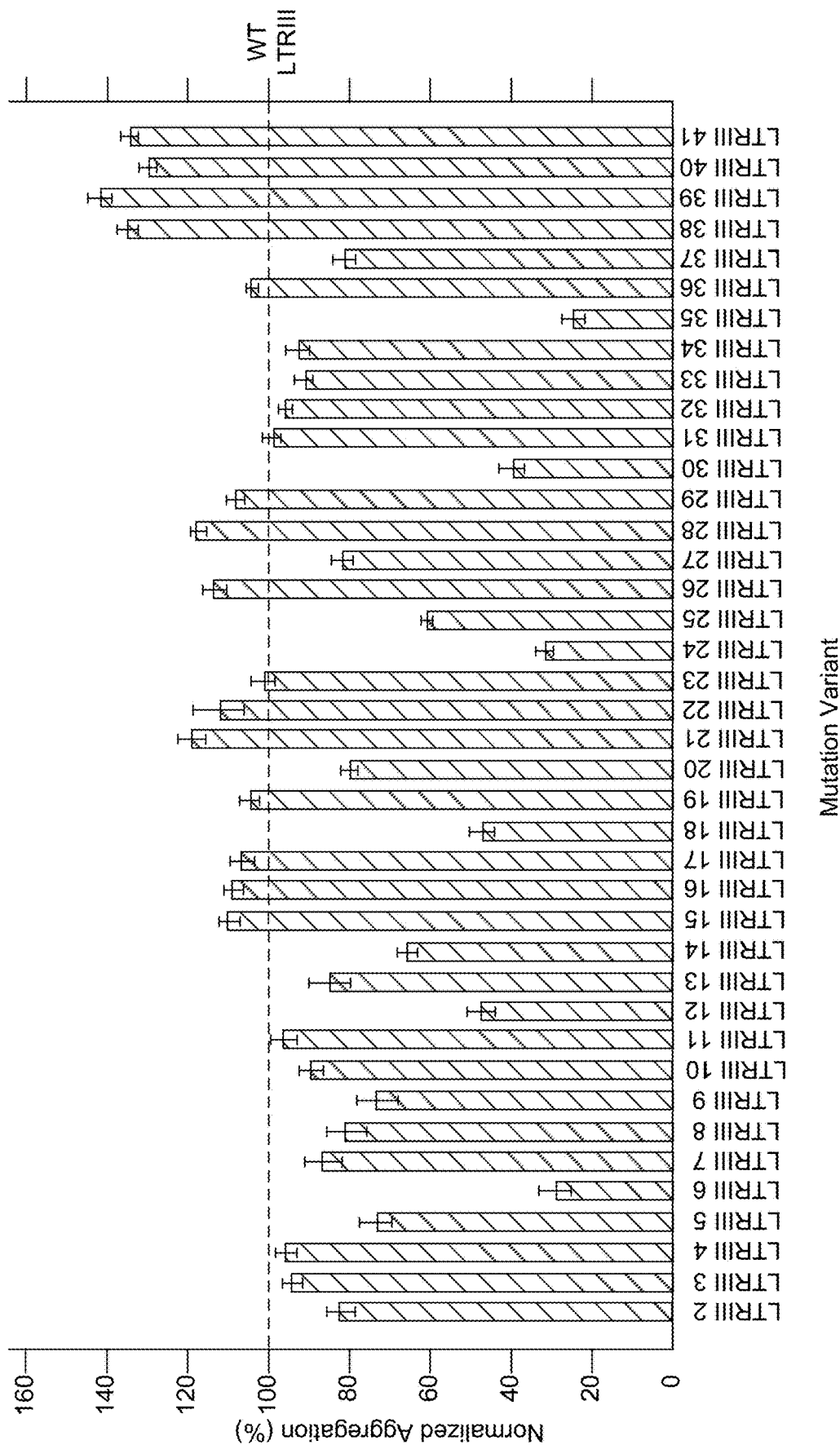
FIG. 11 illustrates exemplary results of an exemplary thermal aggregation experiment comprising LTRIII (SEQ ID NO:37) sequence mutation variants, in accordance with one or more embodiments.
Figure 12:
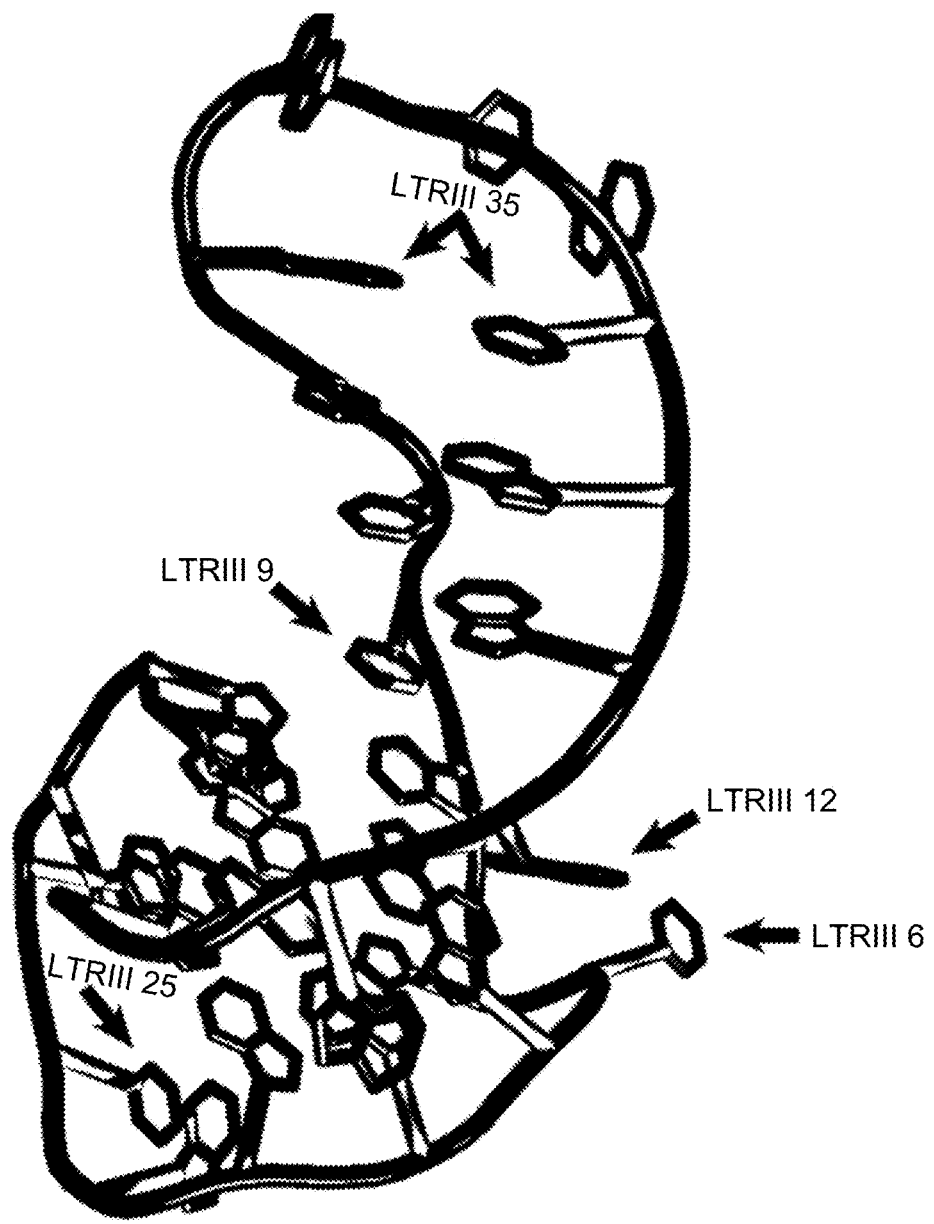
FIG. 12 illustrates an exemplary visual representation of LTRIII (SEQ ID NO:37) sequence structure showing locations of select mutations (including mutation locations of LTRIII6 (SEQ ID NO:38), LTRIII9 (SEQ ID NO:39), LTRIII12 (SEQ ID NO:40), LTRIII25 (SEQ ID NO:41), and LTRIII35 (SEQ ID NO:42)), in accordance with one or more embodiments.

In FIG. 11 shown are the experimental thermal aggregation results to such assays. Percent aggregation of LTRIII (SEQ ID NO:37) was calculated as a function of the maximum absorbance value recorded in the hour and a half divided by the maximum protein alone absorbance value. The percent aggregation of the LTRIII (SEQ ID NO:37) variants compared to LTRIII (SEQ ID NO:37) was normalized to the LTRIII (SEQ ID NO:37)+CS signal for each given plate. Error bars shown are standard error propagated from both the triplicate protein alone and triplicate experimental measurement. As a control, herring testes DNA was also run on each plate to ensure consistency of data. 40 mutants of LTRIII (SEQ ID NO:37) in both loop regions, as well as the quadruplex and duplex regions, were tested to determine the importance of different structural features. As seen in FIG. 11, improvements have been made in holdase activity using several different mutants. For the most part, these mutations have caused only small changes to the topology of the quadruplexes as measured by CD (Table 1, CD r-values of select mutations used to quantify quadruplex topology). Therefore, the mutations may likely be causing only localized structural changes, but can cause major improvements in anti-aggregation and chaperone activity. FIG. 12 is a visual representation of the LTRIII (SEQ ID NO:37) structure that shows the specific location of select mutations with arrows. Several of the changes that caused improved activity were to extrahelical bases that could more easily interact with proteins.

DISCUSSION

In the above experiments, a systematic investigation of the holdase activity of nucleic acids demonstrated that this activity may be sequence specific, and that quadruplex sequences may display potent holdase activity. This holdase activity was demonstrated to be general, preventing the aggregation of multiple proteins that differed considerably in pI, size, and function. Further testing showed that this activity arose in part via protein:nucleic acid oligomerization. This activity was also found to be more efficient than any previously characterized protein chaperone.

Despite the ability of nucleic acids to serve as powerful chaperones in vitro, previously known chaperone-like activities described in living cells for nucleic acids are restricted to well-known RNA binding proteins with typical RNA-binding motifs, or for RNAs binding to their evolved RNA-binding partners. The present disclosure demonstrates the ability of nucleic acids optimized for chaperone activity in vitro to improve the folding environment for a separate protein in E. Coli, with the activity similar to that of many known chaperones. Based on the differences between wtGFP and TagRFP675, it appears that electrostatics are an important component of this activity in E. Coli. Additionally, it is likely that the chaperone and oligomerization behavior observed for quadruplex-containing sequences underlies a capacity to accumulate in and help form stress granules.

Quadruplex sequences have recently been implicated in aggregation and phase separation events in the cell that are associated with pathology. The quadruplex-forming GGGGCC repeat expansion in the c9orf72 gene is thought to be a frequent cause of both ALS and frontotemporal dementia (FTD). This quadruplex sequence is transcribed into sense and anti-sense RNA that have been shown to sequester numerous RNA binding proteins into toxic intranuclear foci, resulting in aggregation. GGGGCC quadruplexes forming foci with disordered proteins in the cell is highly consistent with the results of the above experiments. FMRP protein has been shown to be one of the leading causes of the fragile X syndrome as well as one of the leading causes of monogenetic forms of autism. In addition to aggregating in disease, FMRP is a known quadruplex-binding protein. Future studies on whether these roles are related would be of significant interest. The results of the above experiments suggest that these disease-relevant cases are not unique, as this behavior appears to be a general property of quadruplex interaction with partially unfolded or disordered proteins under stress conditions. As demonstrated above, the parallel vs anti-parallel nature of these systems could have a strong effect on their oligomerization and aggregation.

Also of note, some of the quadruplex sequences shown to have the highest chaperone activity also contain sequence regions that are not expected to form quadruplexes or regular secondary structure, suggesting that the inter-relation of the quadruplex and single-stranded regions could be important for activity. For example, pure polyG by itself is not a very efficient chaperone. The sequences characterized herein to have high activity likely bear some structural resemblance to known chaperones; specifically, the end of the quadruplex may be a large hydrophobic surface, surrounded on four sides by flexible charged tails of single-stranded sequences. Known chaperone mechanisms could be used as a starting place for understanding the chaperone activity of quadruplex-containing sequences. As demonstrated in the above experiments, different known topologies of quadruplexes show very different aggregation properties. Specifically, the demonstrated large difference in activity between anti-parallel and mixed 3+1 topology suggests that the quadruplex topology is an important component in its oligomerization properties. Greater topology variance may be achieved utilizing longer sequences than in the experiments above.

Quadruplexes preventing protein aggregation by oligomerizing with their clients is reminiscent of the action by small heat shock proteins (sHsps). This class of sHsps chaperones forms large hetero-oligomer complexes with different clients, keeping these clients soluble and in an accessible state for later refolding by ATP-dependent chaperones. The quadruplexes investigated in the above experiments also formed stable and soluble oligomer complexes with partially folded proteins, suggesting that quadruplexes could use a molecular mechanism similar to those of the sHsps. Of note, the morphology of the oligomers varied with quadruplex sequence in the experiments, further suggesting that altering quadruplex sequence could be a way to control the oligomerization of proteins, particularly under stress conditions.

The following methods were used in experiments of and in relation to the present disclosure:

Sourcing DNA

All DNA was ordered from Integrated DNA Technology using their standard desalting and purification procedures. For the above heat aggregation plate reader assays, DNA was ordered lyophilized, and normalized to guaranteed molar weights by IDT. This DNA was then resuspended in the given buffer and pipetted directly into the plate wells after thorough pipette mixing. The duplex DNA was pre-annealed by IDT using their standard annealing protocol. For all other experiments described above, DNA or RNA was ordered lyophilized in tube form from IDT at the maximum yield achieved during synthesis. The nucleic acids were then resuspended and thoroughly mixed with the given buffer or DEPC-treated water to a known concentration.

Thermal Aggregation Plate Reader Assays

For the initial thermal aggregation assays, 312 single stranded sequences of random sequence, 24 of which varied in length from 15 to 20 bases long, while the rest were all 20 bases long, were incubated with 500 nM Citrate Synthase from porcine heart in a 1:2 protein:DNA strand concentration. Aggregation was measured absorbance at 360 nm in a Biotek Powerwave multi-mode plate reader, with shaking and measurements every 36 seconds. The plates were transferred from ice to a preheated 50° C. plate reader, and the temperature was held constant throughout the experiments. Each plate was run for 1.5 hours in 40 mM Hepes, 7.5 pH (KOH) buffer. The sequences were run in triplicate. Percent aggregation was calculated as a function of the maximum absorbance value recorded in the hour and a half divided by the maximum protein alone absorbance value. Error bars shown are standard error propagated from both the triplicate protein alone and triplicate experimental measurement. As a control, herring testes DNA (Sigma) was also run on each plate to ensure consistency of data.

The enriched population of 192 G-rich sequences (length 20 bases) was performed by biasing 96 of the sequences toward guanine bases at a rate of 55%. 40 sequences were biased towards guanine bases by 75%, and the remaining 56 sequences were created with the motif GGGGGNT systematically placed throughout the sequence, with the remaining 13 bases chosen at random. This process was accomplished by altering the random bias in our random sequence generating software.

The above heat denaturation assay with varying DNA concentration was run identically to that described above, with ssDNA strand:protein ratios of: 0.5:1, 1:1, 2:1, 4:1, and 8:1. The known quadruplex heat denaturation assay was also run identically to that described above, with ssDNA of known quadruplex-forming sequences (see Table 1). The sequence 359 RNA heat denaturation assay used 0.1% DEPC-treaded autoclaved and filtered DI water.

Aggregation was also tested using Quantilum Recombinant Luciferase, L-malate dehydrogenase (MDH) from pig heart, and L-Lactate Dehydrogenase (LDH) from rabbit muscle. 24 sequences were chosen from the above citrate synthase assay whose anti-aggregation ability spanned the entire range of the data. Of these 24, 14 had a propensity to form quadruplexes. The assay with these other three proteins was carried out identically to the citrate synthase thermal denaturation assay, with LDH being run for 3 hours due to its higher stability at 50° C. These assays were run in 1:2 protein:DNA strand ratios using 10 mM sodium phosphate, 7.5 pH buffer at protein concentrations of 500 nM Luciferase, 2 µM MDH, and 4 µM LDH.

Motif Analysis

Motif analysis was performed using the HOMER package to compare the one-third of sequences with the highest holdase activity to the one-third of sequences with the lowest holdase activity. The parameters used were "-len 5,6,7,8,9,10-norevopp-noconvert-nomask-mis 2-basic-nogo-noredun-noweight-fdr 1000". MatrixREDUCE was also used to identify motifs correlated with holdase activity by regression method. Spearman correlation analysis was performed by R.

Chemical Aggregation Light Scattering

For the chemically induced aggregation, 12 µM Citrate Synthase was denatured in 6 M guanidine-HCl, 40 mM HEPES, for approximately 16 h at 23° C., then diluted to 75 nM into 40 mM HEPES, pH 7.5 (KOH), with constant stirring at 23° C. in the presence of 150 nM 20-mer ssDNA. The resulting aggregation was then measured via right angle light scattering at 360 nm in a fluorimeter with constant mixing. Results were consistently repeated on three separate days, with representative curves shown.

N-methylmesoporphyrin IX (NMM) Fluorescence

NMM is a well characterized fluorophore that increases fluorescence when bound to parallel quadruplexes. The emission spectra of 10 µM NMM was measured using an excitation wavelength of 399 nm, and an emission range of 550 to 750 nm in the presence of 1 µM DNA in 10 mM sodium phosphate, pH 7.5. Samples were run in triplicate at 25° C. in a multimode plate reader. Reported values are taken at 610 nm, the emission maxima, as a function of increase in fluorescence compared to a NMM alone triplicate control.

Construction of Expression Vectors

Expression vectors were generated of protein folding enhancing factors, i.e., pBAD33-molecular chaperone (GroEL, DnaK, Hsp33, ClpA, Spy, IbpA, and IbpB), pBAD33mut-RNA (Seq42 (SEQ ID NO:4), Seq359 (SEQ ID NO:1), Seq536 (SEQ ID NO:2), and Seq576 (SEQ ID NO:3)), and pBAD33mut-Empty. The expression vectors of pBAD33-molecular chaperone (GroEL, DnaK, Hsp33, ClpA, Spy, IbpA, and IbpB) were constructed from pBAD33 using the SacI and HindIII sites. Each molecular chaperone gene was obtained by PCR using E. coli genome. pBAD33mut-empty vector (Empty) was generated from pBAD33 vector. Briefly, the MCS of the pBAD33 vector was changed into SacI and SpeI, using MluI and BglII restriction enzymes. The genes of the selected set of RNAs (Seq42 (SEQ ID NO:4), Seq359 (SEQ ID NO:1), Seq536 (SEQ ID NO:2), and Seq576 (SEQ ID NO:3)) were synthesized (Genscript). pBAD33mut-Seq42 (SEQ ID NO:4), Seq359 (SEQ ID NO:1), Seq536 (SEQ ID NO:2), and Seq576 (SEQ ID NO:3) were generated using the SacI and SpeI sites. For the expression of biosensors, we used pBAD/HisD-TagRFP675 and pBAD18-wtGFP. Strains and plasmids used are listed in Table 2.

Protein Expression, and *Escherichia coli* Fluorescence Assay

Each resulting expression vector of protein folding enhancing factors and pBAD/HisD-TagRFP675 or pBAD33-wtGFP were co-transformed into the E. coli strain MC4100(DE3) by heat shock. To induce protein and/or RNA expression, each transformant was streaked on an LB plate containing 0.2% L-Arabinose, ampicillin (200 µg/ml), and chloramphenicol (50 µg/ml) at 42° C. overnight. To determine whether pBAD promoter is tightly controlled, non-induced LB plates containing the same amount of antibiotics were used for both +Empty and +GroEL samples. The next day, non-induced and induced cells were scraped in 170 mM NaCl and harvested by centrifugation at 10,000 g for 2 min at 4° C. Pictures of cell pellets were taken immediately after harvesting to compare color. Cells were then resuspended in 170 mM NaCl and diluted to 0.1 $OD_{600}$ for further fluorescence assays. Fluorescence emission of each sample was measured by microplate reader using a black 96-well plate. Fluorescence emissions of TagRFP675 (at 576 nm) and wtGFP (at 395 nm) were measured upon excitation at 598 nm and 509 nm, respectively.

*Escherichia Coli* Growth Assay

To measure cell growth of each sample, each strain was inoculated into 3 ml of LB medium containing ampicillin (200 µg/ml) and chloramphenicol (50 µg/ml), and cultured at 37° C. overnight. The next day, 1 µl of each culture was transferred into 99 µl of LB medium containing 0.08% L-Arabinose, ampicillin (200 µg/ml), and chloramphenicol (50 µg/ml). The samples were added into a clear flat bottom 96-well plate and grown for 19 h at 42° C. with shaking for 10 min every hour. $OD_{600}$ of each sample was measured with a microplate reader every hour. All samples were measured in triplicate.

GFP In Vitro Fluorescence Assay

A GFP stock was prepared using Recombinant *A. victoria* green fluorescent protein in 20 mM potassium chloride and 20 mM Tris, pH 7.5 buffer (HCl) containing 1 mM DTT. Herring Testes DNA (htDNA) was prepared using deoxyribonucleic acid sodium salt from herring testes dissolved in 20 mM KCl and 20 mM Tris, pH 7.5 buffer. The htDNA solution was washed three times at 4° C., using a 3 kD molecular cutoff weight cellulose ultra-centrifuge spin filter, according to manufacturer's protocol. All samples were prepared on ice.

Experimental samples were prepared with a final GFP concentration of 1.4 nM containing 0.2408 mg/ml htDNA or GFP alone, as a control. Samples were then denatured at 93° C. for 20 min. Following denaturing, 100 µl of each sample was immediately transferred to a treated black 96-well plate. Fluorescence was measured at 37° C. using a fluorescent plate reader (excitation/emission: 390/508 nm), over a 60-minute incubation period. All samples were blank subtracted from buffer containing 0.2408 mg/ml htDNA. Experiments were controlled for using non-denatured GFP with htDNA, at the same concentrations. All samples were measured in at least triplicate.

Transmission Electron Microscopy (TEM)

For the oligomer TEM samples shown above, chemical denaturation spin down assays were run using citrate synthase. 46.4 µM Citrate synthase was denatured in 4.8 M guanidine-HCl, 40 mM HEPES buffer for 16 hours. The citrate synthase was then diluted to 1.5 µM in a 100 µL sample containing 3 µM of the target sequence that induced oligomerization. 15 minutes after injection, the sample was spun down at 16,100 g for 20 min at 4° C. The soluble portion was pipetted off and transferred on ice for TEM analysis.

In other oligomer TEM samples from the above experiments, thermal denaturation spin-down assays were run using citrate synthase. 100 µl of 3.8 µM protein and 7.6 µM ssDNA were thermally denatured together at 60° C. for 15 min in 10 mM sodium phosphate, pH 7.5 buffer. The resulting solution was then centrifuged at 16,100 g for 15 min at 4° C. to separate the soluble and insoluble fractions. The soluble portion was pipetted off and transferred on ice for TEM analysis.

In both chemical and thermal denaturation cases, a positively charged copper mesh grid coated in formvar and carbon using the PELCO easiGlow™ glow discharge cleaning system was used for each soluble sample. The charged copper grids had 5 µL of sample applied for 20 seconds and then lightly blotted off using a Whatman filter paper. The grids were then rinsed using 2 drops of water from a MILLI-Q® water purification system, with filter paper bloating for each wash. The grids were then stained using two drops of a 0.75% uranyl formate solution. The first drop served as a quick wash, followed by 20 seconds of staining using the second drop. The grids were then blotted and allowed to dry. The TEM images were captured using a FEI Company Tecnai™ G2 Spirit Bio (TWIN) transmission electron microscope at 80 kV with a side-mount digital camera from AMT Imaging. In order to better visualize the intricacies of each oligomer, the images' contrast and brightness was uniformly enhanced using ADOBE® Photoshop photo and design software.

Circular Dichroism

The CD spectra were obtained using a Jasco J-1100 circular dichroism at 23° C. For the CD spectra shown in FIG. 2A, the sequences were resuspended in 10 mM sodium phosphate pH 7.5 buffer and diluted in the same buffer to 25 µM (per strand) DNA. The CD measurements were taken from 300 nm to 190 nm at 1 nm intervals using a 1 nm/sec scanning speed. The shown spectra are a product of three accumulations using the same conditions.

The luciferase protein denaturation CD spectra were captured in protein:DNA ratios of 1:2 using 3.2 µM luciferase. The CD spectra were captured at 10° C. intervals from 15° C. to 85° C. using a ramp rate of 3° C./min captured from 260 to 190 nm. The concentrations were chosen such that the DNA concentration was below the observable sensitivity range of the instrument.

For nucleic acid melting curves, the sequences were resuspended in 10 mM pH 7.5 potassium phosphate for DNA or DEPC-treated DI water for RNA, both of which were diluted into 10 mM potassium phosphate for spectra acquisition. Spectra were taken at 10° C. intervals from 25° C. to 85° C. at a ramp rate of 2° C./min. Spectra were captured from 320 nm to 190 nm at 1 nm intervals using a 50 nm/min scanning speed over three accumulations.

For annealed quadruplex sequence spectra, quadruplex-forming sequences were heated to 95° C. for two minutes and allowed to cool to room temperature by the internal fan of the heating block, which took 30 min to cool to 25° C. Samples had their CD spectra taken immediately upon their return to 25° C.

Spin-Down Aggregation Assays

For the spin-down aggregation assays, 100 µL of 3.2 µM protein and 6.4 µM ssDNA were thermally denatured together at 60° C. for 15 min in 10 mM sodium phosphate, pH 7.5 buffer. The resulting solution was then centrifuged at 16,100 g for 15 minutes at 4° C. to separate the soluble and insoluble fractions. After centrifugation, the supernatant (approximately 97 µL) was removed and the pellet resuspended using 1 mM β-mercaptoethanol in 1× TG-SDS buffer to the original sample volume of 100 µL. 10 µL of the soluble and pellet fractions were then run on a denaturing SDS-PAGE gel and visualized using Coomassie blue. Gels were reproduced on three separate days, with representative assays shown.

For the chemical denaturation spin down assay, 46.4 µM citrate synthase was denatured in 4.8 M guanidine-HCl, 40 mM HEPES buffer for 16 hours. The citrate synthase was then diluted to 2.5 µM in a 100 µL sample containing 5 µM of the target sequence that induced oligomerization. After 5 minutes, the samples soluble and pellet fractions were separated via the same methods as the thermal denaturation spin down assays. The gels were then run in triplicate identically to the thermal denaturation experiments, with representative gels shown.

Turning now to FIGS. 13A-16E, shown are experiments and experimental results related to the selection of particular nucleic acid sequences and their specific effect on protein aggregation in cells.

Figure 13A:
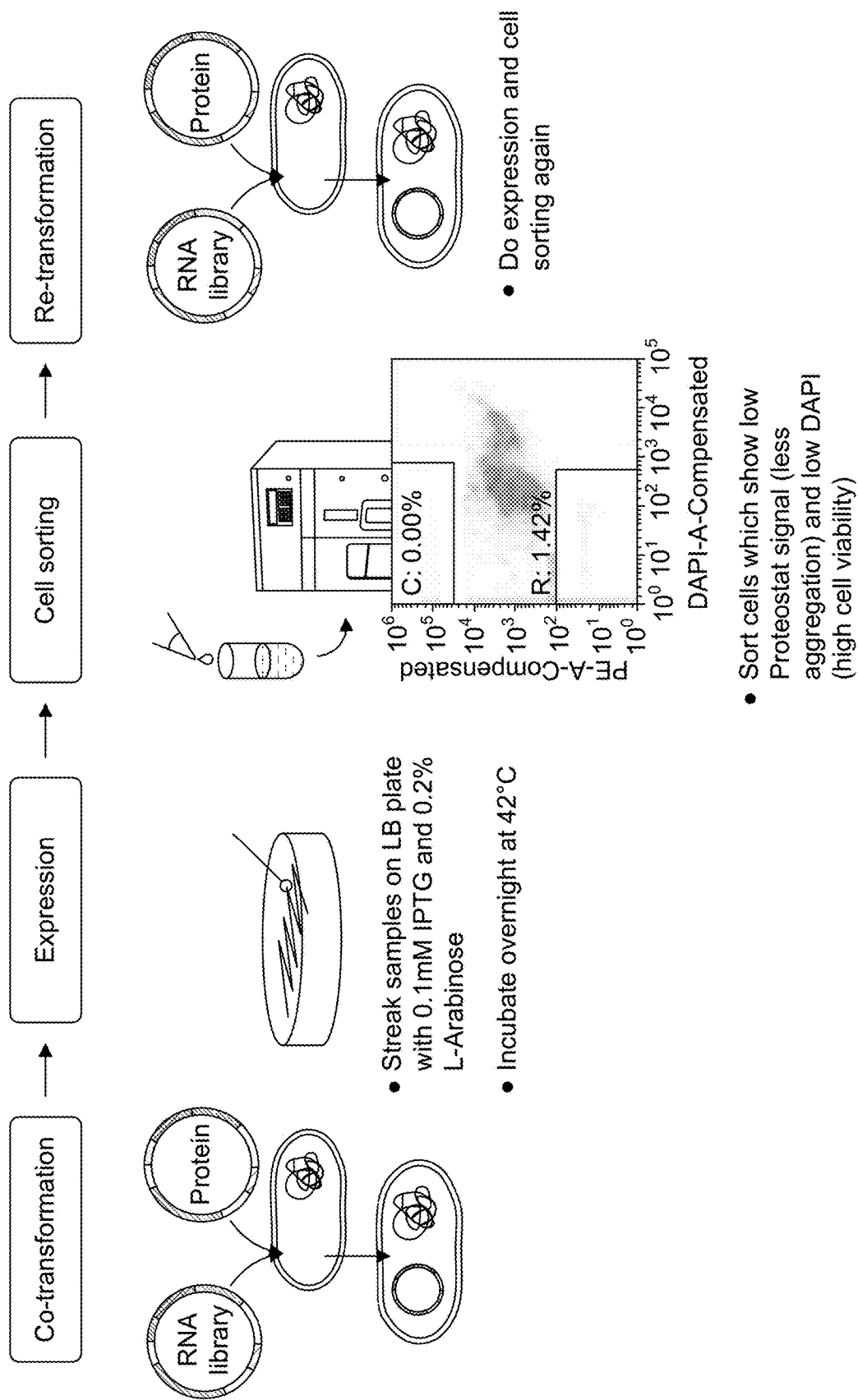
Figure 13B:
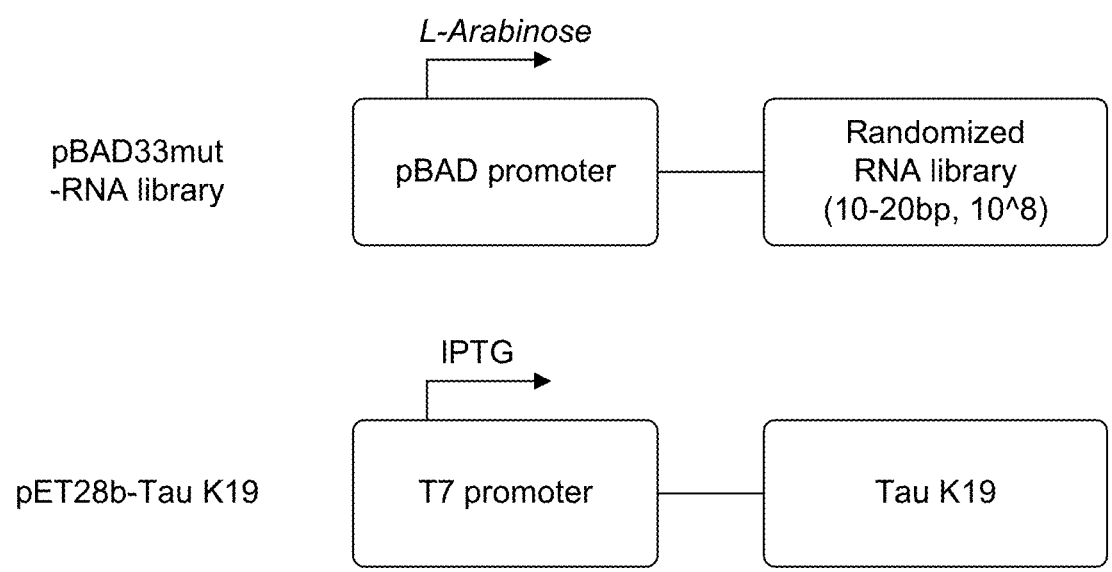
Figure 13C:
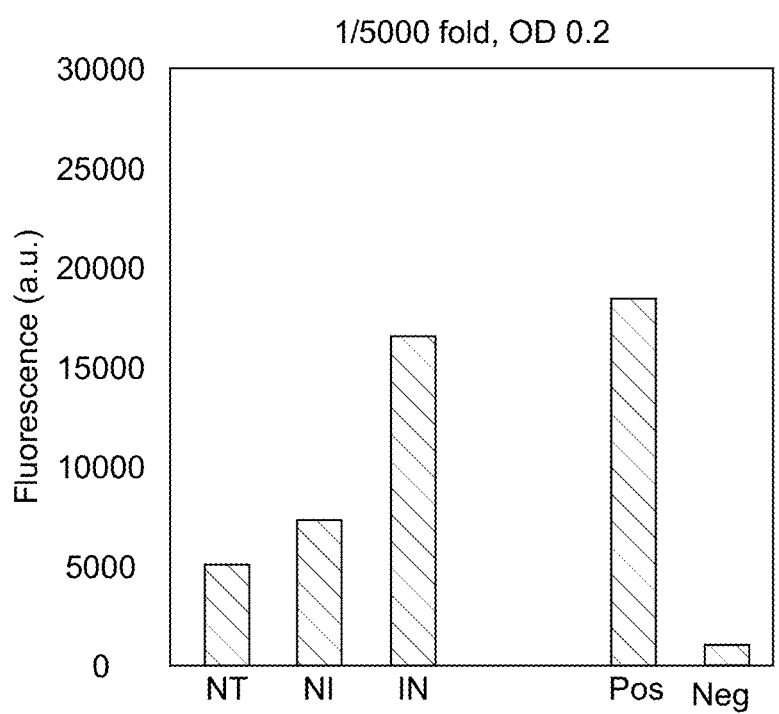
Figure 13D:
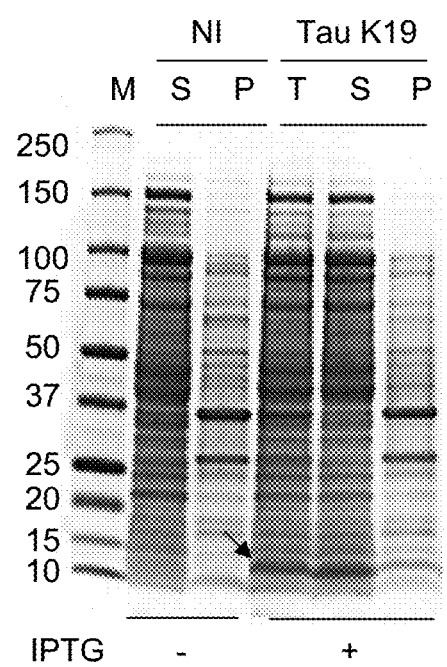

FIGS. 13A-D illustrate an exemplary experiment showing the selection of sRNA sequences which have an effect on the folding status of TauK19. TauK19 is a commonly used, truncated version of the wild type Tau that aggregates in Alzheimer's disease. Using TauK19 as an experimental model of Tau aggregation may enable selection of a specific sequence of sRNA that potentially effects the folding status of both TauK19 and the wild type Tau of Alzheimer's disease, which may provide a means for improving the medical outcome of Alzheimer's patients. FIG. 13A shows a schematic illustration for selection of sRNA sequences. RNA library and TauK19 were co-transformed into E. coli cells, and TauK19 was co-expressed with RNA library on LB plates at 42° C. To detect protein aggregation, PROTEOSTAT® dye was used. Cells which have low or high protein aggregation were sorted and re-transformed into E. coli in order to verify whether sorted sRNA library has a role in the folding status of TauK19. FIG. 13B shows illustrations of exemplary expression vectors. The expression of RNA library is under the control of pBAD promoter, which is induced by L-Arabinose. TauK19 expression is under the control of T7 promoter, which is induced by IPTG. FIG. 13C shows the results of a protein aggregation assay using PROTEOSTAT® dye. NT, NI, IN, Pos, and Neg indicate Non-transformant, Non-induced, Induced, Positive control, and Negative control, respectively. Cells were diluted into 0.2 OD600, and 1:5,000-fold diluted PROTEOSTAT® dye was used to detect protein aggregation. FIG. 13D shows a SDS-PAGE of TauK19 expression. NI, M, S, P, and T, represent Non-induced, Molecular weight marker, soluble fraction, pellet fraction, and total fraction, respectively. The arrow indicates expressed TauK19 protein.

Experiments, such as depicted in FIGS. 13A-D, show that using PROTEOSTAT® dye (which is designed to detect protein aggregates, and has been used in E. coli), appreciable levels of Tau aggregation can be detected in E. coli. Tau is a protein whose aggregation is believed to be causative in several neurological diseases.

Figure 14:
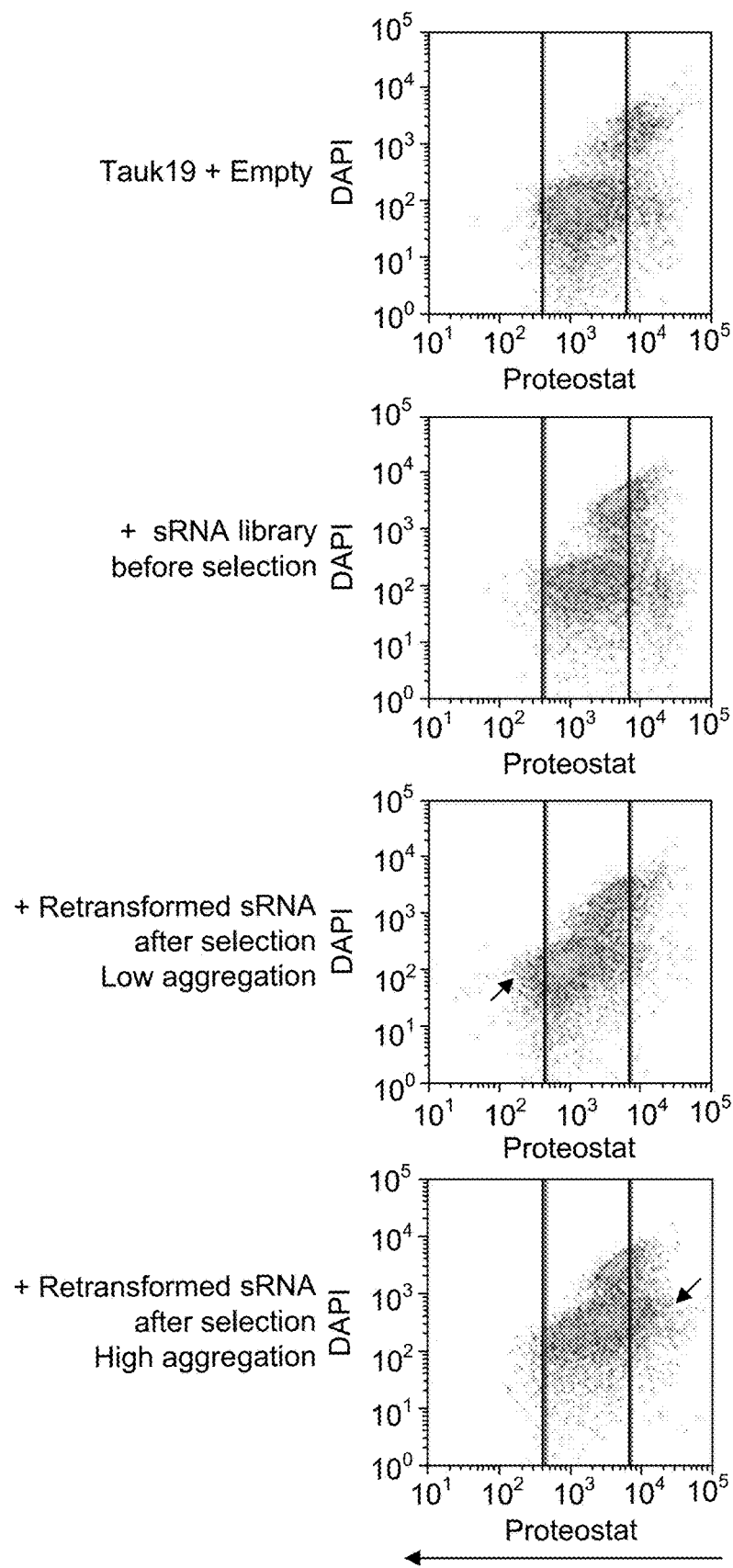
FIG. 14 illustrates exemplary experimental fluorescent-activated cell sorting results of TauK19 with co-expression of empty vector or selected sRNAs, in accordance with one or more embodiments.

FIG. 14 shows exemplary experimental fluorescent-activated cell sorting (FACS) results of TauK19 with co-expression of empty vector or selected sRNAs, such as depicted in FIGS. 13A-D. X-axis and Y-axis represent protein aggregation (i.e., results of PROTEOSTAT® protein aggregation assay or, simply, Proteostat as shown in FIG. 14) and Cell death (DAPI). TauK19 was expressed with empty vector (negative control), Randomized RNA library, and retransformed sRNA selections (Low aggregation and High aggregation). The arrows indicate the decreased or increased aggregation of TauK19 in the presence of selected sRNAs Low aggregation, or High aggregation, respectively. Left and right vertical bars indicate the left and right end of the main cell group with the co-expression of empty vector, respectively.

The FIG. 14 experimental results show that using PROTEOSTAT® fluorescence and the ability for a cell sorter to sort cells two separate ways based on PROTEOSTAT® protein aggregation assay signal, cells that either have low or high aggregation levels in the presence of a specific RNA and Tau may be selected. Retransforming the cells with the plasmid may ensure that the effect is plasmid-encoded (i.e., not due to random chromosomal mutations). However, it should be noted that in some instances such a process may not include a complete analysis of the sequencing of the selected RNAs, leaving some uncertainty as to which specific RNAs were selected.

Figure 15A:
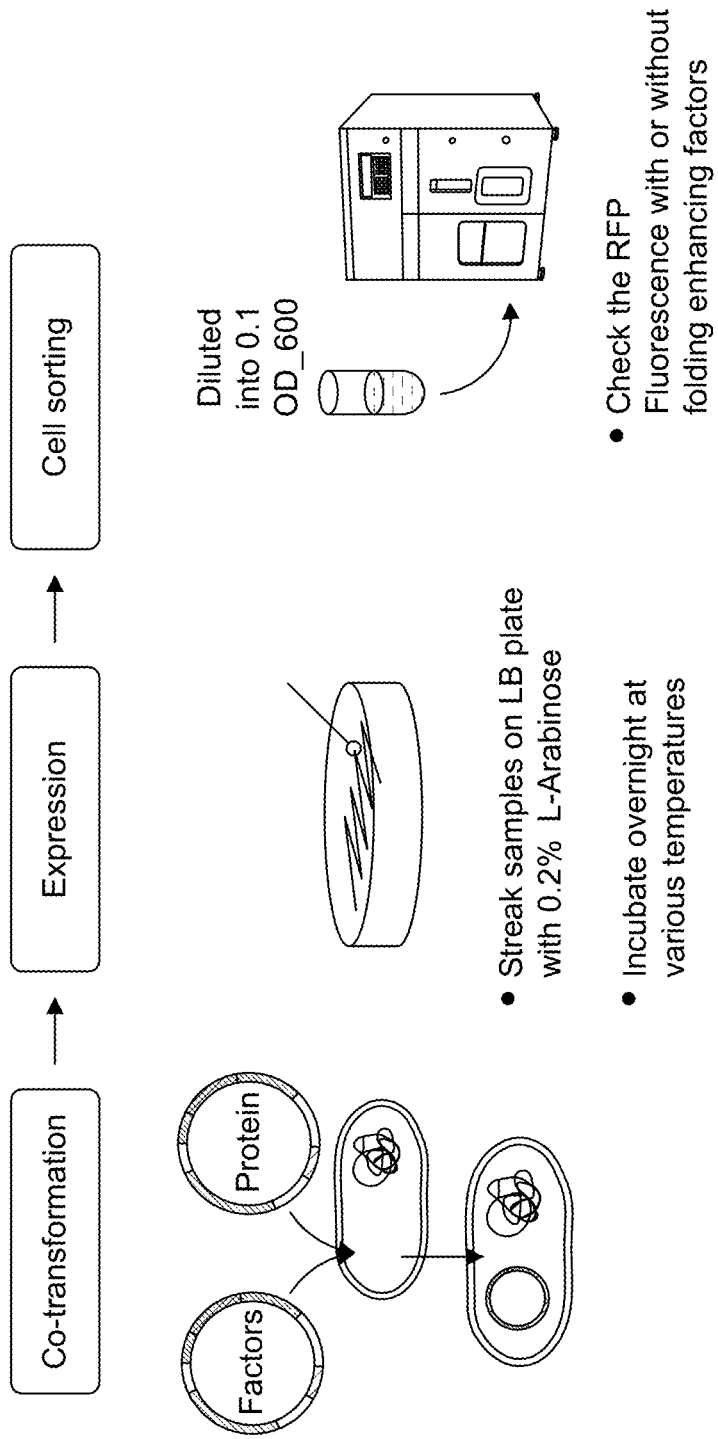
Figure 15B:
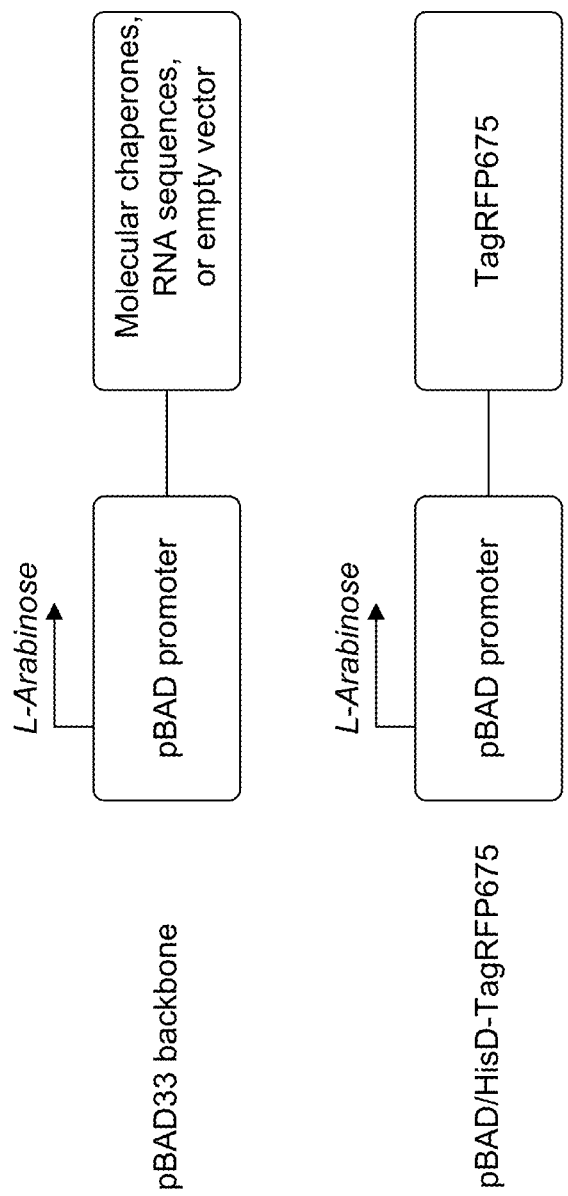
Figure 15C:
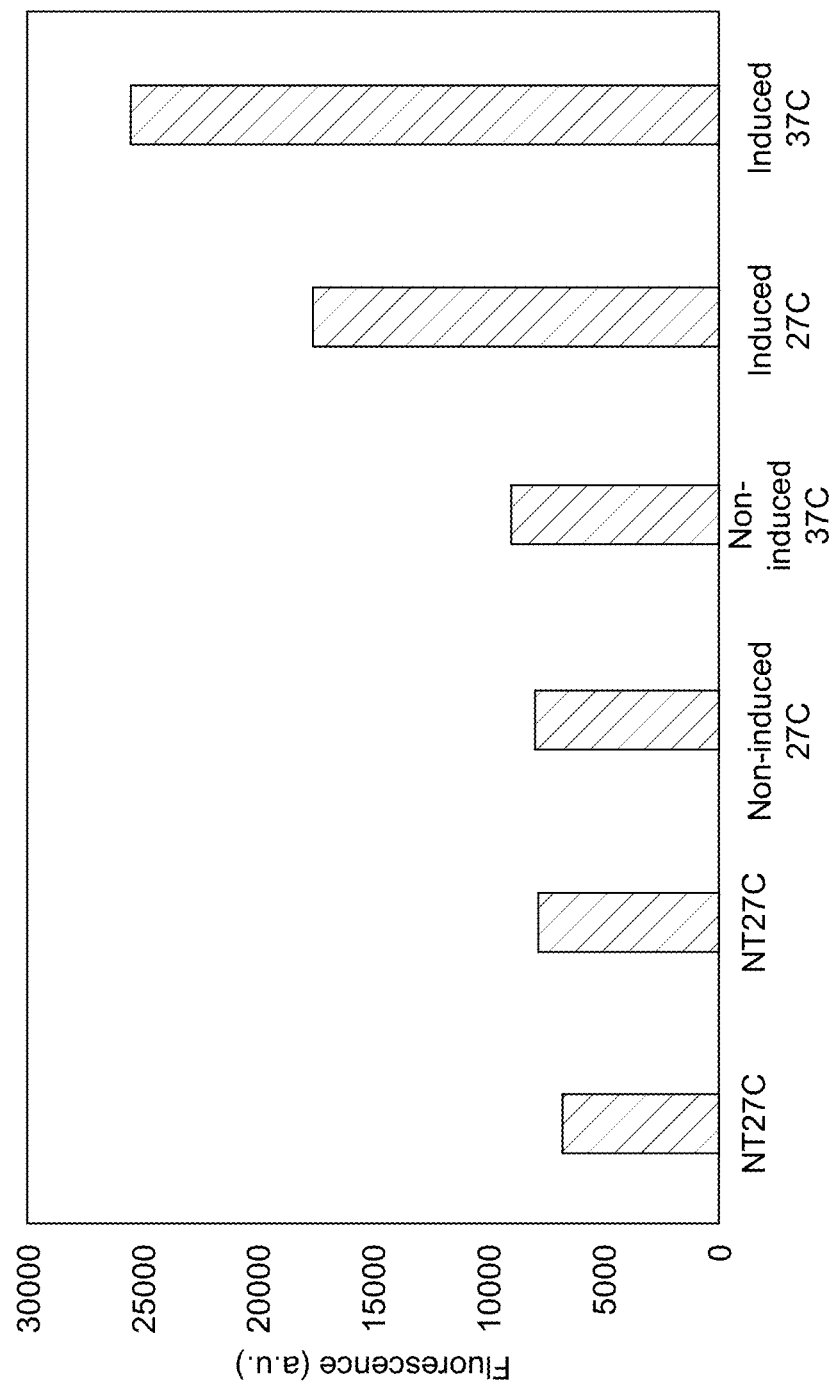

FIGS. 15A-C illustrate an exemplary experiment showing the effect of various folding enhancer factors on the folding status of TagRFP675 protein. FIG. 15A shows a schematic illustration for elucidation of the effect of various factors on the folding status (fluorescence) of TagRFP675 protein. Various folding enhancing factors, such as molecular chaperones, RNA sequences, or empty vector, and TagRFP675 protein were co-transformed into E. coli cells, and the protein and various factors were co-expressed on LB plates at various temperatures. The fluorescence of TagRFP675 in the presence or absence of the factors was examined using a cell sorter. FIG. 15B shows structures of exemplary expression vectors. Both of the expression of protein folding enhancing factors and TagRFP675 are under the control of pBAD promoter, which is induced by L-Arabinose. FIG. 15C shows the results of an exemplary fluorescence assay of TagRFP675. NT indicates Non-transformant. Protein expression was induced at 27° C. or 37° C., and the fluorescence of each sample was measured with a plate reader.

Figure 16F:
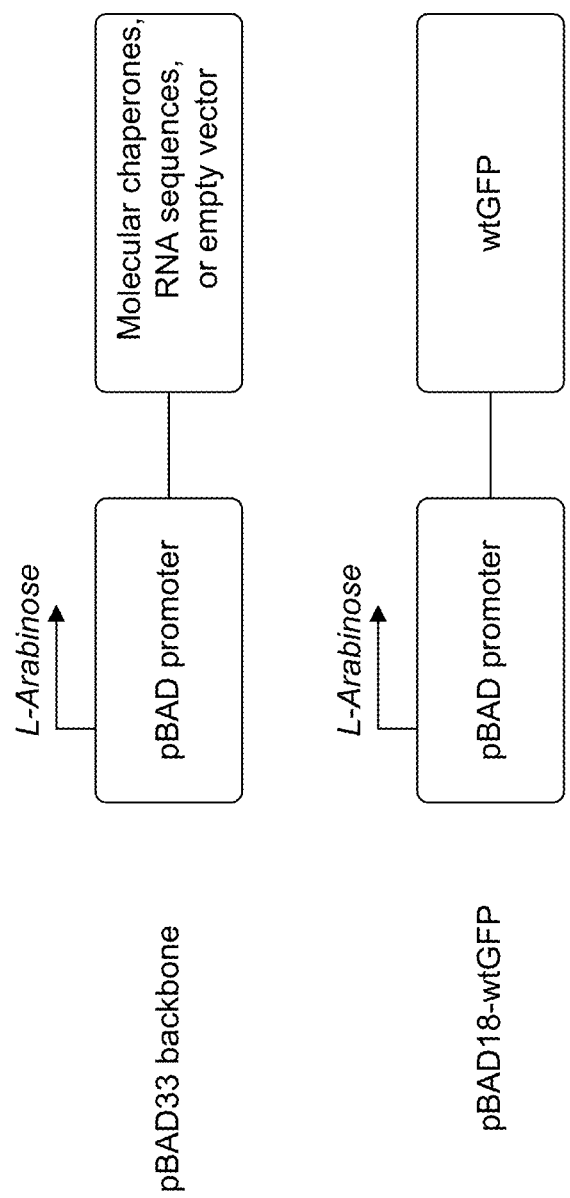
Figure 16G:
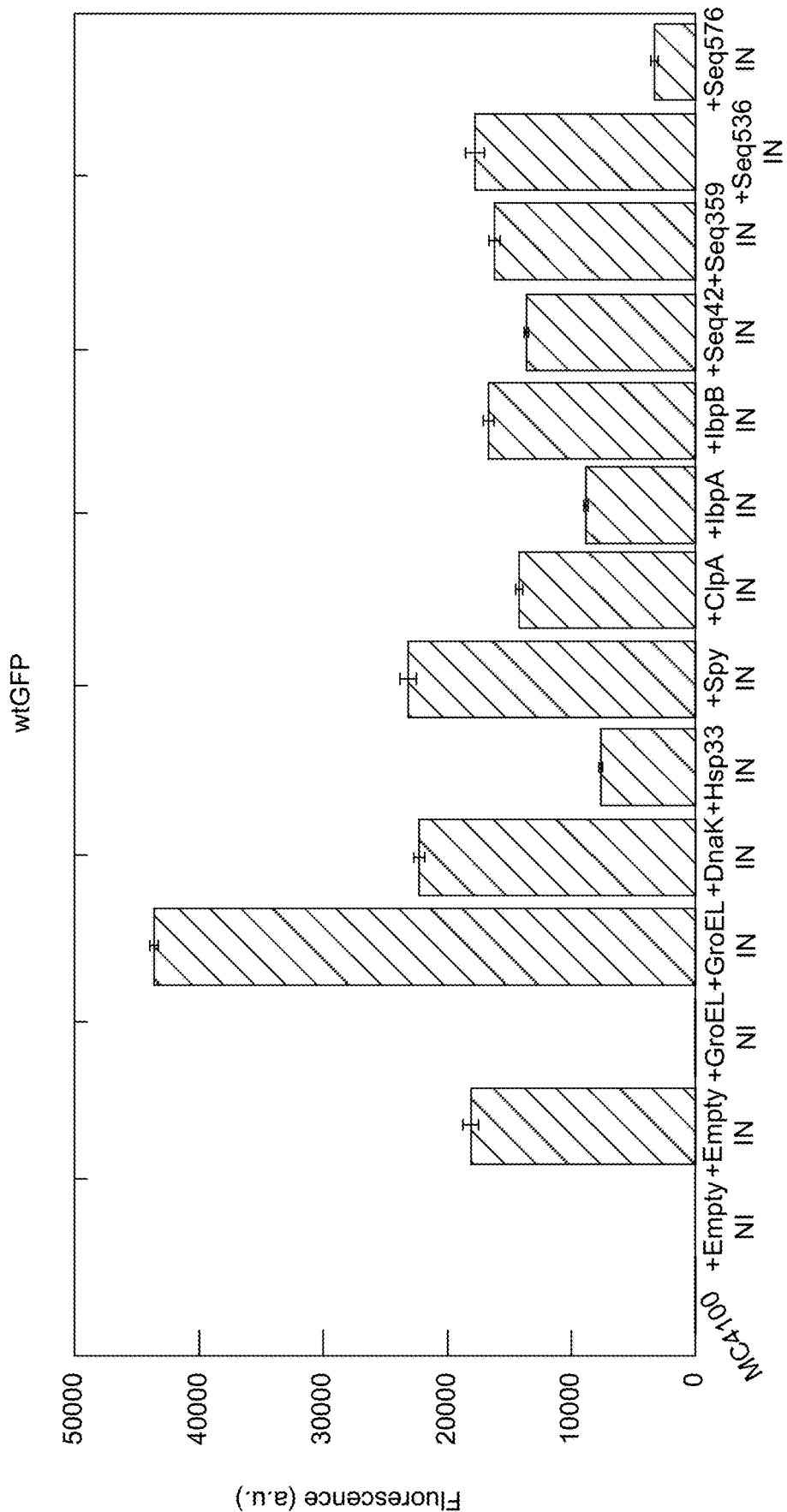

FIGS. 16A-G illustrate the results of an exemplary experiment showing the folding status of TagRFP675 and wtGFP modulated by various folding enhancing factors. In the experiment cells induced at 37° C. (FIGS. 16A-B) and 42° C. (FIGS. 16C-G) were used for FACS analysis. FIGS. 16A and 16C show harvested cells. Arrows indicate cells which showed strong color difference. Empty vector (negative control), molecular chaperones (GroEL, DnaK, Hsp33, Spy, ClpA, IbpA, and IbpB), and selected RNA sequences (Seq42 (SEQ ID NO:4), Seq359 (SEQ ID NO:1), Seq536 (SEQ ID NO:2), and Seq576 (SEQ ID NO:3)) were used as protein folding enhancers. NI and IN indicate Non-induced and Induced. FIGS. 16B-1-16B-12 and 16D-1-16D-12 show exemplary experimental FACS results of TagRFP675. X-axis and Y-axis represent fluorescence of TagRFP675 (Protein folding) and DAPI (Cell death). Left vertical lines of each column indicate the center part of cells with the co-expression of empty vector, and right vertical lines represent the maximum boundary of fluorescence of the cells in the presence of empty vector. FIG. 16F shows structures of exemplary expression vectors, one of which includes wtGFP. FIGS. 16E and 16G show the results of cellular fluorescence assays of TagRFP675 and wtGFP, respectively, with the various folding enhancing factors used in the experiment. Fluorescence of each sample was measured with a spectrometer.

Of the variety of known chaperones included, several are shown to cause a color change in the cells, including GroEL DnaK, and ClpA, indicative of increased TagRFP675 folding. The same types of color changes are observed from the three quadruplexes tested. This indicates that these quadruplexes are improving the folding environment of E. coli for TagRFP675 folding. The observed increase in the effect from 37° C. to 42° C. is consistent with this interpretation. Of note, it has not been determined whether this effect is direct (quadruplexes binding to TagRFP675 and helping them to fold) or indirect (any other possible mechanism). The use of TagRFP675 as a folding biosensor is novel, and a nucleic acid being shown to have a general chaperone effect (i.e. not just for a protein it evolved to bind specifically) in cells is novel as well.

In the exemplary experiment of FIGS. 16A-G, Tau and Proteostat are replaced with a fluorescent protein, either TagRFP675 or wtGFP. In order to fluoresce, the protein must be in its native, folded state, and have the self-catalyzed chromophore reaction completed. If the protein unfolds after this reaction, it will lose its fluorescence, but it will likely refold much faster than if the reaction has not happened yet.

As shown, the particular sRNA sequences affected the folding, and therefore, the aggregation, of particular proteins. It is contemplated that other specifically selected nucleic acid sequences in addition to the ones described in the above experiments may be used to affect the levels of folding and protein aggregation in particular compounds and compositions. Thus, the teachings of the above experiments may be generalized to systems, methods, and compounds for providing chaperone activity to proteins. For example, the equipment and methods used in the above exemplary experiments, such as those described in the thermal aggregation plate reader assays, motif analysis, chemical aggregation light scattering, NMM fluorescence, construction of expression vectors, protein expression and E. coli fluorescence assay, E. coli growth assay, GFP in vitro fluorescence assay, transmission electron microscopy, circular dichroism, and spin-down aggregation assays sections, as well as those relating to FACS, may be used in and provide a means for selecting and applying specific nucleic acid sequences to provide chaperone activity to proteins.

Figure 17:
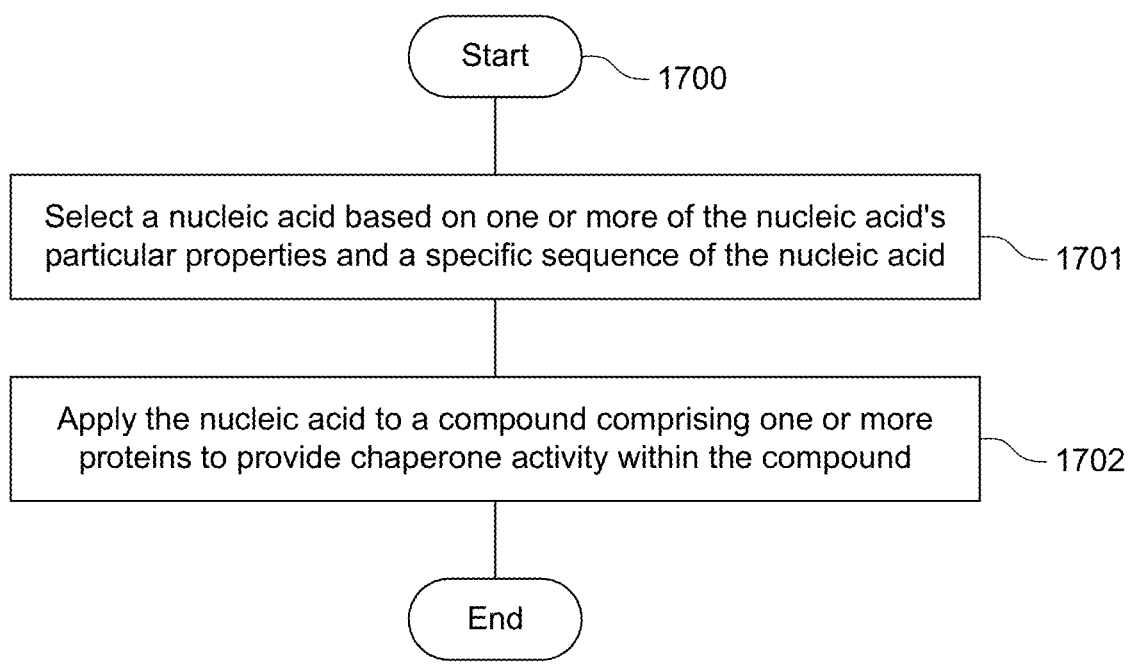
FIG. 17 illustrates an exemplary method for providing chaperone activity to a protein-containing compound, in accordance with one or more embodiments.

FIG. 17 shows a method 1700 of the present disclosure for providing chaperone activity to a protein-containing compound. The method 1700 may comprise, in block 1701, selecting a nucleic acid based on one or more of the nucleic acid's particular properties and a specific sequence of the nucleic acid. The method 1700 may further comprise, in block 1702, applying the nucleic acid to a compound comprising one or more proteins to provide chaperone activity to the compound. The applying of block 1702 may include providing chaperone activity to the compound with the nucleic acid, wherein the chaperone activity may comprise at least one of preventing protein aggregation and improving protein folding within the compound, such as of the one or more proteins. For example, applying of block 1702 may include providing chaperone activity to the compound with the nucleic acid, wherein the chaperone activity may comprise preventing protein aggregation within the compound, and the amount of protein aggregation may be within a range of under 60% of that of the protein, such as the one or more proteins, alone, without the nucleic acid, as measured by turbidity at 360 nm. The chaperone activity may, therefore, be said to reduce the protein aggregation by 40% or more. The selecting of block 1701 may include selecting based on one or more of the nucleic acid's particular properties, wherein the particular properties of the nucleic acid may include, for example, at least one of degree of efficacy of the nucleic acid's chaperone activity provided to the compound, and the one or more proteins therein, and the nucleic acid's effect on protein:nucleic acid oligomerization within the compound. The selecting of block 1701 may include selecting at least one of a nucleic acid containing a quadruplex sequence, or quadruplex nucleic acid, and a nucleic acid containing a G-quadruplex sequence, or G-quadruplex nucleic acid, as the nucleic acid. The selecting of block 1701 may include selecting a G-quadruplex nucleic acid comprising a specific sequence as the G-quadruplex nucleic acid, wherein the specific sequence of the G-quadruplex nucleic acid may comprise at least one of Seq359 (SEQ ID NO:1), Seq536 (SEQ ID NO:2), Seq576 (SEQ ID NO:3), LTRIII6 (SEQ ID NO:38), LTRIII9 (SEQ ID NO:39), LTRIII12 (SEQ ID NO:40), LTRIII25 (SEQ ID NO:41), LTRIII (SEQ ID NO:37), and any other sequence of the present disclosure. The one or more proteins may be comprised of proteins that are not known RNA biding proteins.

The applying of block 1702 may include applying the nucleic acid to a synthetic compound as the compound. For example, the applying of block 1702 may include applying the nucleic acid to a synthetic compound being at least one of a pharmaceutical compound, industrial compound, cosmetic compound, and edible compound as the synthetic compound, and the applying of block 1702 may include improving the stability of the compound utilizing the chaperone activity, potentially extending the duration of the effectiveness of the compound before expiration. Alternatively, the applying of block 1702 may include applying the nucleic acid to a naturally occurring compound as the compound. For example, the applying of block 1702 may include applying the nucleic acid to a naturally occurring compound comprising tissue or protein as the compound, and the applying of block 1702 may include reducing a disease state symptom utilizing the chaperone activity, potentially improving medical outcomes. In a particular example, the applying of block 1702 may include applying the nucleic acid to a compound comprising IgG antibodies as the compound, and the applying of block 1702 may include reducing protein aggregation related to the IgG antibodies, such as aggregation of monoclonal IgG antibodies, utilizing the chaperone activity, which may enable medical treatments utilizing IgG antibodies to become more viable with potentially longer durations until expiration. The applying of block 1702 may include applying the nucleic acid to an intracellularly contained, such as within a cell of a human or other cellular organism, compound as the compound and the nucleic acid may be applied to the one or more proteins within a cell, such as to provide chaperone activity to the one or more proteins within the cell. Intracellular application may enable the treatment of particular medical conditions, such as diseases associate with protein aggregation. Means for applying the nucleic acid to the cell may comprise various transfection or other techniques known in the art for transporting nucleic acids through cell membranes and introducing them into cells.

In some embodiments, the applying of block 1702 may include providing general chaperone activity to a plurality of proteins. For example, the nucleic acid may provide general chaperone activity to a plurality of proteins within the compound, wherein the general chaperone activity may include chaperone activity that may be provided to a plurality of proteins through a plurality of different binding domains.

The selecting of block 1701 may comprise assessing efficacy of the nucleic acid's chaperone activity, such as through the use of at least one of the multitude of techniques taught in the present disclosure. For example, a means for assessing efficacy of the nucleic acid's chaperone activity may be provided by the equipment and techniques of the present disclosure, such as those described in the thermal aggregation plate reader assays, motif analysis, chemical aggregation light scattering, NMM fluorescence, construction of expression vectors, protein expression and E. coli fluorescence assay, E. coli growth assay, GFP in vitro fluorescence assay, transmission electron microscopy, circular dichroism, and spin-down aggregation assays sections, as well as those relating to FACS. In a particular example, TagRFP675 may be used as a fluorescent marker, such as a biomarker, for protein folding to assess efficacy of the nucleic acid's chaperone activity based on the degree of fluorescence of TagRFP675, such as in vivo. The degree of fluorescence may be interpreted in one of the above fluorescence assays to assess the efficacy of the nucleic acid's chaperone activity. The assessing of the efficacy of the nucleic acid's chaperone activity may include a screening process, comprised of one or more of the above-mentioned means-for-assessing examples, screening a plurality of nucleic acids.

The selecting of block 1701 may comprise altering the specific sequence of the nucleic acid to improve chaperone activity within the compound. For example, as described above, such as in the improving chaperone activity section, various mutations of a specific nucleic acid sequence may be generated, through alteration, or tuning, of the specific sequence of the nucleic acid, and assessed based on efficacy of the resulting nucleic acid's chaperone activity. Such various mutations may be generated in a selective manner, wherein prior knowledge of the nucleic acid and nucleic acids in general, such as the topology and chaperone activity of specific sequences, may be utilized to select particular mutations to generate. Additionally or alternatively, the various mutations may be generated in a procedural, batch manner, wherein a plurality of mutations may be generated randomly. The various mutations, or alterations, may be assessed, or procedurally screened, as described above based on efficacy of the altered nucleic acid's chaperone activity.

The selecting of block 1701 may comprise determining the quadruplex content of the nucleic acid, such as through the use of at least one of the multitude of techniques taught in the present disclosure. For example, a means for determining the quadruplex content of the nucleic acid may be provided by the equipment and techniques of the present disclosure, such as those described in the NMM fluorescence and circular dichroism sections. In a particular example, CD spectroscopy and/or NMM fluorescence may be used to determine if a specific sequence of a nucleic acid contains quadruplexes.

The selecting of block 1701 may comprise a variety of other nucleic-acid-selection-related aspects of the present disclosure that may aid in the described selecting process.

The applying of block 1702 may comprise one or more of the following methods along with the respective equipment known to be used for such processes as a means for applying the nucleic acid to the compound: dissolving in solution, mixing, topically applying, expressing in organisms, and transfecting into cells. Other methods of applying nucleic acids may also be used without departing from the scope of the disclosure.

Some embodiments of the present disclosure may comprise a product of the process described in method 1700, the product comprising a solution. The solution may comprise an oligonucleotide with a quadruplex-containing specific sequence, wherein the oligonucleotide may have been selected based on the specific sequence. The solution may further comprise one or more proteins to which chaperone activity is provided by the oligonucleotide. The oligonucleotide may have been selected based on the efficacy of the chaperone activity provided to the one or more proteins by the oligonucleotide. The chaperone activity may comprise at least one of preventing protein aggregation and improving protein folding within the compound, such as of the one or more proteins. For example, the chaperone activity may comprise preventing protein aggregation within the compound, and the amount of protein aggregation may be within a range of under 60% of that of the protein, such as the one or more proteins, alone, without the oligonucleotide, as measured by turbidity at 360 nm. The specific sequence of the oligonucleotide may comprise at least one of: Seq359 (SEQ ID NO:1), Seq536 (SEQ ID NO:2), Seq576 (SEQ ID NO:3), LTRIII6 (SEQ ID NO:38), LTRIII9 (SEQ ID NO:39), LTRIII12 (SEQ ID NO:40), LTRIII25 (SEQ ID NO:41), LTRIII (SEQ ID NO:37), and any other sequence of the present disclosure. The one or more proteins may be comprised of proteins that are not previously-known RNA biding proteins. Other embodiments may utilize nucleic acids of greater length than the above-discussed oligonucleotides of the solution.

Some embodiments of the present disclosure may comprise a composition comprising as an active ingredient an effective amount of a nucleic acid to provide chaperone activity to a protein, the nucleic acid comprising a G-quadruplex-containing specific sequence, wherein the nucleic acid may be selected based on the specific sequence. The nucleic acid may also be selected based on efficacy of the chaperone activity provided to the protein. The chaperone activity may comprise at least one of preventing protein aggregation and improving protein folding within the composition, such as of the protein. The specific sequence of the nucleic acid may comprise at least one of Seq359 (SEQ ID NO:1), Seq536 (SEQ ID NO:2), Seq576 (SEQ ID NO:3), LTRIII6 (SEQ ID NO:38), LTRIII9 (SEQ ID NO:39), LTRIII12 (SEQ ID NO:40), LTRIII25 (SEQ ID NO:41), LTRIII (SEQ ID NO:37), and any other sequence of the present disclosure. The one or more proteins may be comprised of proteins that are not previously-known RNA biding proteins. The efficacy of the nucleic acid's chaperone activity may be assessed through the use of at least one of the multitude of techniques taught in the present disclosure. For example, TagRFP675 may be used as a fluorescent marker, such as a biomarker, for protein folding to assess efficacy of the chaperone activity provided to the protein by the nucleic acid based on the degree of fluorescence of TagRFP675, such as in vivo. The degree of fluorescence may be interpreted in one of the above fluorescence assays to assess the efficacy of the nucleic acid's chaperone activity. The assessing of the efficacy of the nucleic acid's chaperone activity may include a screening process, screening a plurality of nucleic acids.

The efficacy of the nucleic acid's chaperone activity may be assessed through the use of at least one of the multitude of techniques taught in the present disclosure. For example, TagRFP675 may be used as a fluorescent marker, such as a biomarker, for protein folding to assess efficacy of the chaperone activity provided to the protein by the nucleic acid based on the degree of fluorescence of TagRFP675, such as in vivo. The degree of fluorescence may be interpreted in one of the above fluorescence assays to assess the efficacy of the nucleic acid's chaperone activity. The assessing of the efficacy of the nucleic acid's chaperone activity may include a screening process, screening a plurality of nucleic acids.

In some embodiments, the composition may comprise no other nucleic acids than the nucleic acid comprising the G-quadruplex-containing specific sequence. For example, the composition may contain only a single variant of nucleic acid with a specific sequence that is optimized to provide chaperone activity to the protein. Such targeted, single-variant nucleic acid containing compositions may enable increased chaperone activity provided to the protein without the inclusion of unoptimized or ineffectual nucleic acids. Such unoptimized or ineffectual nucleic acids may potentially inhibit the ability of the optimized specific sequence to interact with the protein, such as through binding inhibition, and may increase production costs through their unnecessary production. Additionally, in some cases, such unoptimized or ineffectual nucleic acids may introduce negative, harmful aspects to the composition when paired with the single-variant nucleic acid, such as through the induction of cytotoxic effects to living cells. Therefore, the targeted, single-variant nucleic acid containing compositions described above may enable an improvement in composition safety, by removing potentially harmful components, as well as efficacy and production cost.

Some embodiments of the present disclosure may comprise a system configured for providing chaperone activity to a protein-containing compound. The system may comprise means for selecting a nucleic acid based on one or more of the nucleic acid's particular properties and a specific sequence of the nucleic acid and means for applying the nucleic acid to a compound comprising one or more proteins to provide chaperone activity to the compound. Such means for selecting and means for applying are discussed in the description of the method 1700 of FIG. 17 and may be applied in the system. The chaperone activity may comprise at least one of preventing protein aggregation and improving protein folding within the compound, such as of the one or more proteins. For example, the chaperone activity may comprise preventing protein aggregation within the compound, and the amount of protein aggregation may be within a range of under 60% of that of the protein, such as the one or more proteins, alone, without the nucleic acid, as measured by turbidity at 360 nm. The particular properties of the nucleic acid may include, for example, at least one of degree of efficacy of the nucleic acid's chaperone activity provided to the compound, and the one or more proteins therein, and the nucleic acid's effect on protein:nucleic acid oligomerization within the compound. The nucleic acid may be at least one of a nucleic acid containing a quadruplex sequence, or quadruplex nucleic acid, or a nucleic acid containing a G-quadruplex sequence, or G-quadruplex nucleic acid. The specific sequence of the nucleic acid may comprise at least one of Seq359 (SEQ ID NO:1), Seq536 (SEQ ID NO:2), Seq576 (SEQ ID NO:3), LTRIII6 (SEQ ID NO:38), LTRIII9 (SEQ ID NO:39), LTRIII12 (SEQ ID NO:40), LTRIII25 (SEQ ID NO:41), LTRIII (SEQ ID NO:37), and any other sequence of the present disclosure. The one or more proteins may be comprised of proteins that are not previously-known RNA biding proteins.

The compound of the system may be a synthetic compound. For example, the compound may be a synthetic pharmaceutical compound, and the chaperone activity may improve the stability of the pharmaceutical compound, potentially extending the duration of the effectiveness of the pharmaceutical compound before expiration. Alternatively, the compound the system may be a naturally occurring compound. For example, the compound may be naturally occurring, comprising elements such as tissue or protein, and the chaperone activity may reduce a disease state symptom, potentially improving medical outcomes. In a particular example, the compound may comprise IgG antibodies and the chaperone activity may reduce protein aggregation related to the IgG antibodies, such as aggregation of monoclonal IgG antibodies. The compound of the system may be contained intracellularly, such as within a cell of a human or other cellular organism, and the nucleic acid may be applied to the one or more proteins within a cell, such as to provide chaperone activity to the one or more proteins within the cell.

The system may comprise means for assessing efficacy of the nucleic acid's chaperone activity, such as through the use of at least one of the multitude of techniques taught in the present disclosure. Such means for assessing are discussed in the method 1700 of FIG. 17 and may be applied in the system. In a particular example, TagRFP675 may be used as a fluorescent marker, such as a biomarker, for protein folding as a means for assessing efficacy of the nucleic acid's chaperone activity based on the degree of fluorescence of TagRFP675, such as in vivo. The degree of fluorescence may be interpreted in one of the above fluorescence assays to assess the efficacy of the nucleic acid's chaperone activity. The assessing of the efficacy of the nucleic acid's chaperone activity may include a screening process, screening a plurality of nucleic acids.

The means for selecting of the system may comprise means for altering the specific sequence of the nucleic acid to improve chaperone activity within the compound. Such means for altering are discussed in the method 1700 of FIG. 17 and may be applied in the system. For example, as described above, such as in the improving chaperone activity section, various mutations of a specific nucleic acid sequence may be generated, through alteration, or tuning, of the specific sequence of the nucleic acid, and assessed based on efficacy of the resulting nucleic acid's chaperone activity. Such various mutations may be generated in a selective manner, wherein prior knowledge of the nucleic acid and nucleic acids in general, such as the topology and chaperone activity of specific sequences, may be utilized to select particular mutations to generate. Additionally or alternatively, the various mutations may be generated in a procedural, batch manner, wherein a plurality of mutations may be generated randomly. The various mutations, or alterations, may be assessed, or procedurally screened, as described above based on efficacy of the altered nucleic acid's chaperone activity.

The system may comprise means for determining the quadruplex content of the nucleic acid, such as through the use of at least one of the multitude of techniques taught in the present disclosure. Such means for determining are discussed in the method 1700 of FIG. 17 and may be applied in the system. For example, CD spectroscopy and/or NMM fluorescence may be used to determine if a specific sequence of a nucleic acid contains quadruplexes.

In some embodiments, it is contemplated that aspects of a system, such as the system described above, may be automated and/or preprogrammed to execute the described method 1700 of FIG. 17. For example, the equipment and methods described in the exemplary experiments may be conducted in an automated fashion within a preprogrammed system. Such a preprogrammed system may be configured to receive a protein and a variety of nucleic acids, execute one or more of the methods described in the exemplary experiments, such as assays, in an automated fashion, and interpret the results, such as through measured absorbance or scattering of light, to select one or more nucleic acids based on, for example, a specific sequence of the nucleic acids and/or efficacy of the nucleic acids' chaperone activity provided to the protein, from the variety of nucleic acids. For example, the results may be interpreted by a preprogrammed system using AI and/or machine learning to select one or more nucleic acids that may be optimal for providing chaperone activity to the protein.

Figure 18:
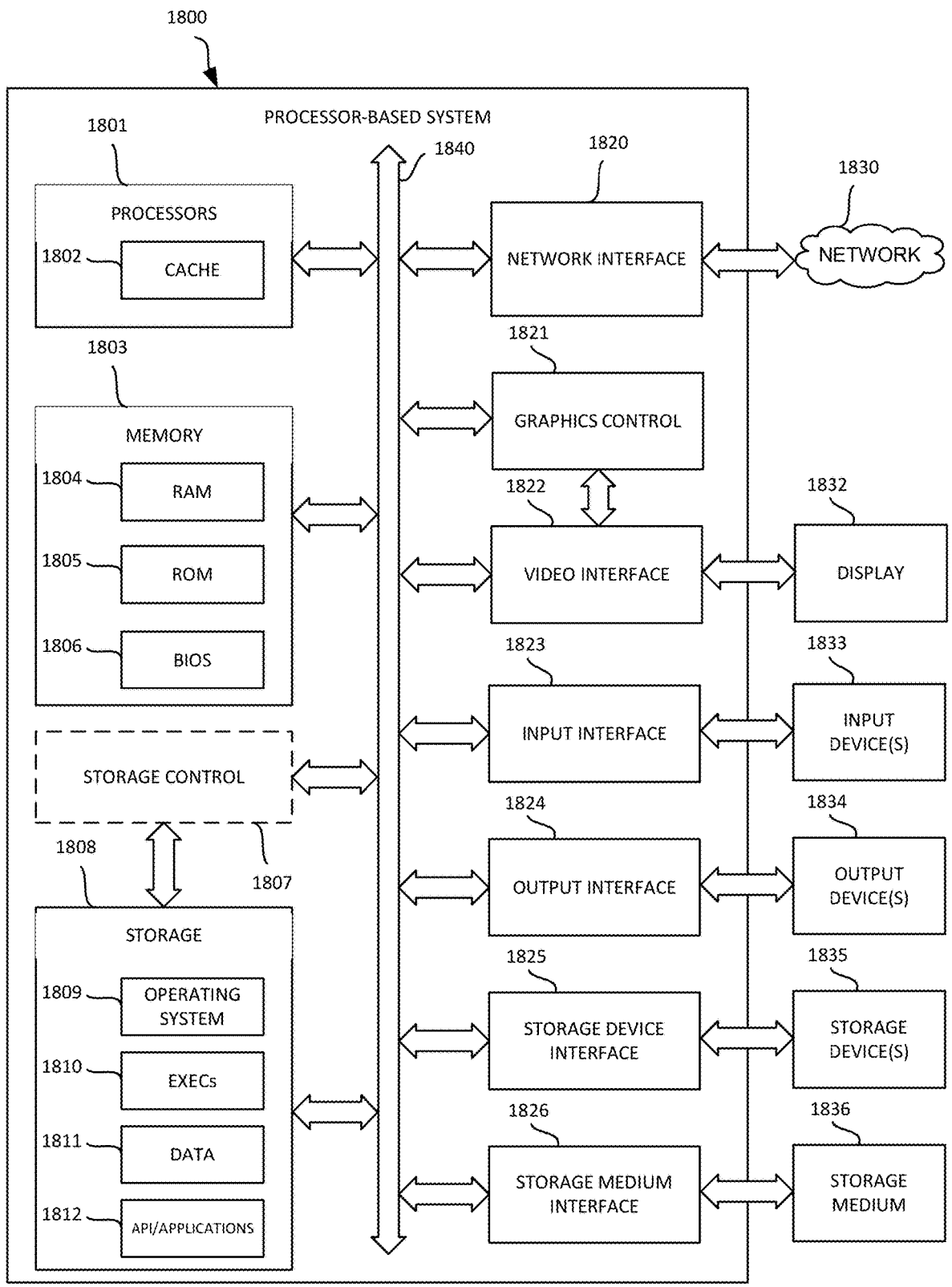
FIG. 18 illustrates an exemplary block diagram depicting physical structures that may be utilized in connection with implementing the embodiments disclosed herein.

The systems and methods described herein can be implemented in a machine such as a processor-based system in addition to the specific physical devices described herein. FIG. 18 shows a diagrammatic representation of one embodiment of a machine in the exemplary form of a processor-based system 1800 within which a set of instructions can execute for causing a device to perform or execute any one or more of the aspects and/or methodologies of the present disclosure. The components in FIG. 18 are examples only and do not limit the scope of use or functionality of any hardware, software, embedded logic component, or a combination of two or more such components implementing particular embodiments.

Processor-based system 1800 may include processors 1801, a memory 1803, and storage 1808 that communicate with each other, and with other components, via a bus 1840. The bus 1840 may also link a display 1832 (e.g., touch screen display), one or more input devices 1833 (which may, for example, include a keypad, a keyboard, a mouse, a stylus, etc.), one or more output devices 1834, one or more storage devices 1835, and various tangible storage media 1836. All of these elements may interface directly or via one or more interfaces or adaptors to the bus 1840. For instance, the various non-transitory tangible storage media 1836 can interface with the bus 1840 via storage medium interface 1826. Processor-based system 1800 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Processors 1801 (or central processing unit(s) (CPU(s))) optionally contain a cache memory unit 1802 for temporary local storage of instructions, data, or computer addresses. Processor(s) 1801 are configured to assist in execution of processor-executable instructions. Processor-based system 1800 may provide functionality as a result of the processor(s) 1801 executing software embodied in one or more tangible processor-readable storage media, such as memory 1803, storage 1808, storage devices 1835, and/or storage medium 1836. The processor-readable media may store software that implements particular embodiments, and processor(s) 1801 may execute the software. Memory 1803 may read the software from one or more other processor-readable media (such as mass storage device(s) 1835, 1836) or from one or more other sources through a suitable interface, such as network interface 1820. The software may cause processor(s) 1801 to carry out one or more processes or one or more steps of one or more processes described or illustrated herein. Carrying out such processes or steps may include defining data structures stored in memory 1803 and modifying the data structures as directed by the software.

The memory 1803 may include various components (e.g., machine readable media) including, but not limited to, a random access memory component (e.g., RAM 1804) (e.g., a static RAM "SRAM", a dynamic RAM "DRAM, etc.), a read-only component (e.g., ROM 1805), and any combinations thereof. ROM 1805 may act to communicate data and instructions unidirectionally to processor(s) 1801, and RAM 1804 may act to communicate data and instructions bidirectionally with processor(s) 1801. ROM 1805 and RAM 1804 may include any suitable tangible processor-readable media described below. In one example, a basic input/output system 1806 (BIOS), including basic routines that help to transfer information between elements within processor-based system 1800, such as during start-up, may be stored in the memory 1803.

Fixed storage 1808 is connected bidirectionally to processor(s) 1801, optionally through storage control unit 1807. Fixed storage 1808 provides additional data storage capacity and may also include any suitable tangible processor-readable media described herein. Storage 1808 may be used to store operating system 1809, EXECs 1810 (executables), data 1811, APV applications 1812 (application programs), and the like. Often, although not always, storage 1808 is a secondary storage medium (such as a hard disk) that is slower than primary storage (e.g., memory 1803). Storage 1808 can also include an optical disk drive, a solid-state memory device (e.g., flash-based systems), or a combination of any of the above. Information in storage 1808 may, in appropriate cases, be incorporated as virtual memory in memory 1803.

In one example, storage device(s) 1835 may be removably interfaced with processor-based system 1800 (e.g., via an external port connector (not shown)) via a storage device interface 1825. Particularly, storage device(s) 1835 and an associated machine-readable medium may provide nonvolatile and/or volatile storage of machine-readable instructions, data structures, program modules, and/or other data for the processor-based system 1800. In one example, software may reside, completely or partially, within a machine-readable medium on storage device(s) 1835. In another example, software may reside, completely or partially, within processor(s) 1801.

Bus 1840 connects a wide variety of subsystems. Herein, reference to a bus may encompass one or more digital signal lines serving a common function, where appropriate. Bus 1840 may be any of several types of bus structures including, but not limited to, a memory bus, a memory controller, a peripheral bus, a local bus, and any combinations thereof, using any of a variety of bus architectures. As an example and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Processor-based system 1800 may also include an input device 1833. In one example, a user of processor-based system 1800 may enter commands and/or other information into processor-based system 1800 via input device(s) 1833. Examples of an input device(s) 1833 include, but are not limited to, an alpha-numeric input device (e.g., a keyboard), a pointing device (e.g., a mouse or touchpad), a touchpad, a joystick, a gamepad, an audio input device (e.g., a microphone, a voice response system, etc.), an optical scanner, a video or still image capture device (e.g., a camera), and any combinations thereof. Input device(s) 1833 may be interfaced to bus 1840 via any of a variety of input interfaces 1823 (e.g., input interface 1823) including, but not limited to, serial, parallel, game port, USB, FIREWIRE, THUNDERBOLT, or any combination of the above.

In particular embodiments, when processor-based system 1800 is connected to network 1830, processor-based system 1800 may communicate with other devices, specifically mobile devices and enterprise systems, connected to network 1830. Communications to and from processor-based system 1800 may be sent through network interface 1820. For example, network interface 1820 may receive incoming communications (such as requests or responses from other devices) in the form of one or more packets (such as Internet Protocol (IP) packets) from network 1830, and processor-based system 1800 may store the incoming communications in memory 1803 for processing. Processor-based system 1800 may similarly store outgoing communications (such as requests or responses to other devices) in the form of one or more packets in memory 1803 and communicated to network 1830 from network interface 1820. Processor(s) 1801 may access these communication packets stored in memory 1803 for processing.

Examples of the network interface 1820 include, but are not limited to, a network interface card, a modem, and any combination thereof. Examples of a network 1830 or network segment 1830 include, but are not limited to, a wide area network (WAN) (e.g., the Internet, an enterprise network), a local area network (LAN) (e.g., a network associated with an office, a building, a campus or other relatively small geographic space), a telephone network, a direct connection between two computing devices, and any combinations thereof. A network, such as network 1830, may employ a wired and/or a wireless mode of communication. In general, any network topology may be used.

Information and data can be displayed through a display 1832. Examples of a display 1832 include, but are not limited to, a liquid crystal display (LCD), an organic liquid crystal display (OLED), a cathode ray tube (CRT), a plasma display, and any combinations thereof. The display 1832 can interface to the processor(s) 1801, memory 1803, and fixed storage 1808, as well as other devices, such as input device(s) 1833, via the bus 1840. The display 1832 is linked to the bus 1840 via a video interface 1822, and transport of data between the display 1832 and the bus 1840 can be controlled via the graphics control 1821.

In addition to a display 1832, processor-based system 1800 may include one or more other peripheral output devices 1834 including, but not limited to, an audio speaker, a printer, and any combinations thereof. Such peripheral output devices may be connected to the bus 1840 via an output interface 1824. Examples of an output interface 1824 include, but are not limited to, a serial port, a parallel connection, a USB port, a FIREWIRE port, a THUNDERBOLT port, and any combinations thereof.

In addition or as an alternative, processor-based system 1800 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a processor-readable medium may encompass a circuit (such as an IC) storing software for execution, a circuit embodying logic for execution, or both, where appropriate. The present disclosure encompasses any suitable combination of hardware, software, or both.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, or hardware in connection with software. Various illustrative components, blocks, modules, circuits, and steps have been described above generally in terms of their functionality. Whether such functionality is implemented as hardware or hardware that utilizes software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

TABLE 1

Select Nucleic Acid Sequences of the Present Disclosure

| SEQ ID NO | Name | Sequence | Aggregation Assays in FIGS. | Quadruplex? (G4 Hunter Score or reference) |
|---|---|---|---|---|
| 1 | Seq359 | GGG GGG GTA ACG GGC TGG TT | FIGS. 2, 3 (SeqA), and 5 | Yes (1.95) |

TABLE 1-continued

Select Nucleic Acid Sequences of the Present Disclosure

| SEQ ID NO | Name | Sequence | Aggregation Assays in FIGS. | Quadruplex? (G4 Hunter Score or reference) |
|---|---|---|---|---|
| 2 | Seq536 | GAG GGG GGC TGC CGT TCA CA | FIGS. 2, 3 (SeqF), and 5 | Yes (1.00) |
| 3 | Seq576 | TGT CGG GCG GGG AGG GGG GG | FIGS. 2, 3 (SeqI), and 5 | Yes (2.60) |
| 4 | Seq42 | AAC GAA AGA ACA TAA TCT CG | FIGS. 2 and 5 | No (<0.1) |
| 5 | Seq398 | GGG GGG CGG TGC GGG AGC GA | FIG. 3 (SeqB) | Yes (1.60) |
| 6 | Seq567 | GGG GGG GCG GCG GGG GGG AG | FIG. 3 (SeqC) | Yes (2.95) |
| 7 | Seq361 | CGG ATG GGG TGG GTG CTG GA | FIG. 3 (SeqD) | Yes (1.60) |
| 8 | Seq573 | GGC GGG CGG TGG GGG GTG CG | FIG. 3 (SeqE) and 5 | Yes (2.00) |
| 9 | Seq563 | TAG GTG GGA GGT GCG GGA GG | FIG. 3 (SeqG) | Yes (1.50) |
| 10 | Seq357 | ATG AGT TGG TGC GTG GGG GA | FIG. 3 (SeqH) | Yes (1.35) |
| 11 | Seq345 | GGG GTT GGT GGG GGG GTA TA | FIG. 3 (SeqI) | Yes (2.40) |
| 12 | Seq582 | GGG GGG GAC GGT GGC GAG GG | FIG. 3 (SeqK) | Yes (2.20) |
| 13 | Seq592 | GGG GGG GGG GCC GGG GGG GT | FIG. 3 (SeqL) and 5 | Yes (3.20) |
| 14 | Seq579 | GGA GGG GGG GGG GTG AGG GG | FIG. 3 (SeqM) | Yes (3.05) |
| 15 | Seq353 | CGG CCG GGC GGG GTC CGG TT | FIG. 3 (SeqN) | Yes (1.15) |
| 16 | Seq364 | GGG CTT TGC ATT TCT ATG GT | FIG. 3 (SeqO) | No (0.55) |
| 17 | Seq63 | GTG GGA TGT CAG ACG TGG AC | FIG. 3 (SeqP) | No (0.7) |
| 18 | Seq60 | CAT CCG AGG TTT ACT CCC CC | FIG. 3 (SeqQ) | No (-1.05) |
| 19 | Seq185 | AAA CGT GCA GTG CAA CAT AA | FIG. 3 (SeqR) | No (<0.1) |
| 20 | Seq190 | GTA CTT TTG GCA TCC TCA CA | FIG. 3 (SeqS) | No (-0.15) |
| 21 | Seq259 | AGT CTT GTT GTG ACT CAA CT | FIG. 3 (SeqT) | No (<0.1) |
| 22 | Seq305 | GAT GAT GTC CGT AGC TTG CC | FIG. 3 (SeqU) | No (-0.15) |
| 23 | Seq347 | AAT GGG ATG CCA TTT GCT GG | FIG. 3 (SeqV) | No (0.5) |
| 24 | Seq209 | GAT ATA GCT GGA GTA CAA CC | FIG. 3 (SeqW) | No (<0.1) |
| 25 | Seq205 | CCA CGA CTG CAG AGG TAT GT | FIG. 3 (SeqX) | No (<0.1) |
| 26 | Seq340 | GGT AGT TCG GTT GGT GGG GA | FIG. 5 | Yes (1.40) |

TABLE 1-continued

Select Nucleic Acid Sequences of the Present Disclosure

| SEQ ID NO | Name | Sequence | Aggregation Assays in FIGS. | Quadruplex? (G4 Hunter Score or reference) |
|---|---|---|---|---|
| 27 | Seq589 | GCG GGG GGA GGG AGG AGG GG | FIG. 5 | Yes (2.65) |
| 28 | Seq580 | CGG GGG TGG AGG GGG GGG AG | FIG. 5 | Yes (2.80) |
| 39 | Seq583 | CGG GAA GGG GGG GCG GAG GG | FIG. 5 | Yes (2.40) |
| 30 | Badic Anti-Parallel | GGG GTT TTG GGG | FIG. 15 | Yes ref: (Haider et al, 2002) |
| 31 | Thrombin Binding Aptamer (TBA) | GGT TGG TGT GGT TGG | FIG. 15 | Yes ref: (Macaya et al, 1993) |
| 32 | Core Human Telomer Quadruplex | AGG TTA GGG TTA GGG TTA GGG | FIG. 15 | Yer ref: (Renčiuk et al, 2009) |
| 33 | Wild Type c-MYC | TGA GGG TGG GGA GGG TGG GGA AGG | FIG. 15 | Yes ref: (Simonsson et al, 1998; Phan et al, 2004; Ambrus et al, 2005) |
| 34 | MYC22 | TGA GGG TGG GGA GGG TGG GGA A | FIG. 15 | Yes ref: (Phan et al, 2004; Ambrus et al, 2005) |
| 35 | MYC12 | TGG GGA GGG TTT TTA GGG TGG GGA | FIG. 15 | Yes ref: (Phan et al, 2004) |
| 36 | PAPR1 Promoter | TGG GGG CCG AGG CGG GGC TTG GG | FIG. 15 | Yes ref: (Sengar et al, 2009) |
| 37 | LTRIII | GGG AGG CGT GGC CTG GGC GGG ACT GGG G | FIG. 15 | Yes ref: (Butovskaya et al, 2018), CD r-value: 0.49 |
| 38 | LTRIII 6 (A4G mutant) | GGG GGG CGT GGC CTG GGC GGG ACT GGGG | FIG. 16 | Yes, CD r-value: 0.61 |
| 39 | LTRIII 9 (T14G mutant) | GGG AGG CGT GGC CGG GGC GGG ACT GGGG | FIG. 16 | Yes, CD r-value: 0.51 |
| 40 | LTRIII 12 (C18G mutant) | GGG AGG CGT GGC CTG GGG GGG ACT GGGG | FIG. 16 | Yes, CD r-value: 0.51 |
| 41 | LTRIII 25 (A22V mutant) | GGG AGG CGT GGC CTG GGC GGG CCT GGGG | FIG. 16 | Yes |
| 42 | LTRIII 35 (C7G, G11C mutant) | GGG AGG GGT GCC CTG GGC GGG ACT GGGG | FIG. 16 | Yes |

TABLE 2

Bacterial Strains and Plasmids

| Strain number | Strains | Genotype | References |
|---|---|---|---|
| AS12 | MC4100(DE3) | Δ(argF-lac) U169 araD139 rpsLS50 reLAl deoCI ptsF25 rpsR flbB301 | (Casadaban, 1976) |

| Strain number | Plasmid1 | Relevant Characteristics | Plasmid2 | Relevant Characteristics | References |
|---|---|---|---|---|---|
| AS181 | pBAD/HisD-TagRFP675 | ApR | pBAD33mut-Empty | CmR | (Piatkevich et al., 2013) |
| AS197 | pBAD19-wtGFP | ApR | pBAD33-GroEL | CmR | (Piatkevich et al., 2013) |
| AS171 | pBAD/HisD-TagRFP675 | ApR | pBAD33-DnaK | CmR | This study |
| AS183 | pBAD/HisD-TagRFP675 | ApR | pBAD33-Hsp33 | CmR | This study |
| AS185 | pBAD/HisD-TagRFP675 | ApR | pBAD33-ClpA | CmR | This study |
| AS187 | pBAD/HisD-TagRFP675 | ApR | pBAD33-Spy | CmR | This study |

TABLE 2-continued

| | | Bacterial Strains and Plasmids | | |
|---|---|---|---|---|
| AS189 | pBAD/HisD-TagRFP675 | ApR | pBAD33-IbpA | CmR | This study |
| AS191 | pBAD/HisD-TagRFP675 | ApR | pBAD33-IbpB | CmR | This study |
| AS193 | pBAD/HisD-TagRFP675 | ApR | pBAD33mut-Seq42 | CmR | This study |
| AS195 | pBAD/HisD-TagRFP675 | ApR | pBAD33mut-Seq359 | CmR | This study |
| AS173 | pBAD/HisD-TagRFP675 | ApR | pBAD33mut-Seq536 | CmR | This study |
| AS175 | pBAD/HisD-TagRFP675 | ApR | pBAD33mut-Seq576 | CmR | This study |
| AS177 | pBAD/HisD-TagRFP675 | ApR | pBAD33mut-Empty | CmR | This study |
| AS179 | pBAD/HisD-TagRFP675 | ApR | pBAD33-GroEL | CmR | This study |
| AS199 | pBAD19-wtGFP | ApR | pBAD33-DnaK | CmR | This study |
| AS209 | pBAD19-wtGFP | ApR | pBAD33-Hsp33 | CmR | This study |
| AS211 | pBAD19-wtGFP | ApR | pBAD33-ClpA | CmR | This study |
| AS212 | pBAD19-wtGFP | ApR | pBAD33-Spy | CmR | This study |
| AS213 | pBAD19-wtGFP | ApR | pBAD33-IbpA | CmR | This study |
| AS214 | pBAD19-wtGFP | ApR | pBAD33-IbpB | CmR | This study |
| AS215 | pBAD19-wtGFP | ApR | pBAD33mut-Seq42 | CmR | This study |
| AS216 | pBAD19-wtGFP | ApR | pBAD33mut-Seq359 | CmR | This study |
| AS201 | pBAD19-wtGFP | ApR | pBAD33mut-Seq536 | CmR | This study |
| AS203 | pBAD19-wtGFP | ApR | pBAD33mut-Seq576 | CmR | This study |
| AS205 | pBAD19-wtGFP | ApR | | | This study |
| AS207 | pBAD19-wtGFP | ApR | | | This study |

What is claimed is:

1. A composition comprising a protein and an effective amount of a nucleic acid,
    wherein the nucleic acid provides chaperone activity to the protein;
    wherein the nucleic acid is selected from the group consisting of SEQ359 (SEQ ID NO 1) and SEQ536 (SEQ ID NO 2); and
    wherein said nucleic acid comprises a G-Quadruplex-containing sequence.

2. The composition of claim 1 wherein the nucleic acid is optimized to provide chaperone activity.

3. The composition of claim 1 where the protein is a synthetic protein.

* * * * *

SEQUENCE LISTING

<160> NUMBER OF SEQ ID NOS: 42

<210> SEQ ID NO 1
<211> LENGTH: 20
<212> TYPE: DNA
<213> ORGANISM: Artificial Sequence
<220> FEATURE:
<223> OTHER INFORMATION: Seq359 in Table 1, synthesized oligonucleotide

<400> SEQUENCE: 1
gggggggtaa cgggctggtt                                          20

<210> SEQ ID NO 2
<211> LENGTH: 20
<212> TYPE: DNA
<213> ORGANISM: Artificial Sequence
<220> FEATURE:
<223> OTHER INFORMATION: Seq536 in Table 1, synthesized oligonucleotide

<400> SEQUENCE: 2 gagggggggct gccgttcaca                                         20

<210> SEQ ID NO 3
<211> LENGTH: 20
<212> TYPE: DNA
<213> ORGANISM: Artificial Sequence
<220> FEATURE:
<223> OTHER INFORMATION: Seq576 in Table 1, synthesized oligonucleotide

<400> SEQUENCE: 3
tgtcgggcgg ggagggggggg                                         20

<210> SEQ ID NO 4
<211> LENGTH: 20
<212> TYPE: DNA
<213> ORGANISM: Artificial Sequence
<220> FEATURE:
<223> OTHER INFORMATION: Seq42 in Table 1, synthesized oligonucleotide

<400> SEQUENCE: 4
aacgaaagaa cataatctcg                                          20

```
<210> SEQ ID NO 5
<211> LENGTH: 20
<212> TYPE: DNA
<213> ORGANISM: Artificial Sequence
<220> FEATURE:
<223> OTHER INFORMATION: Seq398 in Table 1, synthesized oligonucleotide

<400> SEQUENCE: 5 gggggggcggtg cggtagcga                                                    20

<210> SEQ ID NO 6
<211> LENGTH: 20
<212> TYPE: DNA
<213> ORGANISM: Artificial Sequence
<220> FEATURE:
<223> OTHER INFORMATION: Seq567 in Table 1, synthesized oligonucleotide

<400> SEQUENCE: 6
gggggggcgg cggggggggag                                                    20

<210> SEQ ID NO 7
<211> LENGTH: 20
<212> TYPE: DNA
<213> ORGANISM: Artificial Sequence
<220> FEATURE:
<223> OTHER INFORMATION: Seq361 in Table 1, synthesized oligonucleotide

<400> SEQUENCE: 7
cggatggggt gggtgctgga                                                     20

<210> SEQ ID NO 8
<211> LENGTH: 20
<212> TYPE: DNA
<213> ORGANISM: Artificial Sequence
<220> FEATURE:
<223> OTHER INFORMATION: Seq573 in Table 1, synthesized oligonucleotide

<400> SEQUENCE: 8
ggcgggcggt gggggggtgcg                                                    20

<210> SEQ ID NO 9
<211> LENGTH: 20
<212> TYPE: DNA
<213> ORGANISM: Artificial Sequence
<220> FEATURE:
<223> OTHER INFORMATION: Seq563 in Table 1, synthesized oligonucleotide

<400> SEQUENCE: 9
taggtgggag gtgcgggagg                                                     20

<210> SEQ ID NO 10
<211> LENGTH: 20
<212> TYPE: DNA
<213> ORGANISM: Artificial Sequence
<220> FEATURE:
<223> OTHER INFORMATION: Seq357 in Table 1, synthesized oligonucleotide

<400> SEQUENCE: 10
atgagttggt gcgtggggga                                                     20

<210> SEQ ID NO 11
<211> LENGTH: 20
<212> TYPE: DNA
<213> ORGANISM: Artificial Sequence
<220> FEATURE:
<223> OTHER INFORMATION: Seq345 in Table 1, synthesized oligonucleotide

<400> SEQUENCE: 11
``` gggggttggtg gggggggtata                                             20

<210> SEQ ID NO 12
<211> LENGTH: 20
<212> TYPE: DNA
<213> ORGANISM: Artificial Sequence
<220> FEATURE:
<223> OTHER INFORMATION: Seq582 in Table 1, synthesized oligonucleotide

<400> SEQUENCE: 12
gggggggacg gtggcgaggg                                               20

<210> SEQ ID NO 13
<211> LENGTH: 20
<212> TYPE: DNA
<213> ORGANISM: Artificial Sequence
<220> FEATURE:
<223> OTHER INFORMATION: Seq592 in Table 1, synthesized oligonucleotide

<400> SEQUENCE: 13
gggggggggg ccgggggggt                                               20

<210> SEQ ID NO 14
<211> LENGTH: 20
<212> TYPE: DNA
<213> ORGANISM: Artificial Sequence
<220> FEATURE:
<223> OTHER INFORMATION: Seq579 in Table 1, synthesized oligonucleotide

<400> SEQUENCE: 14 ggagggggg gggtgagggg                                                20

<210> SEQ ID NO 15
<211> LENGTH: 20
<212> TYPE: DNA
<213> ORGANISM: Artificial Sequence
<220> FEATURE:
<223> OTHER INFORMATION: Seq353 in Table 1, synthesized oligonucleotide

<400> SEQUENCE: 15
cggccgggcg gggtccggtt                                               20

<210> SEQ ID NO 16
<211> LENGTH: 20
<212> TYPE: DNA
<213> ORGANISM: Artificial Sequence
<220> FEATURE:
<223> OTHER INFORMATION: Seq364 in Table 1, synthesized oligonucleotide

<400> SEQUENCE: 16
gggctttgca tttctatggt                                               20

<210> SEQ ID NO 17
<211> LENGTH: 20
<212> TYPE: DNA
<213> ORGANISM: Artificial Sequence
<220> FEATURE:
<223> OTHER INFORMATION: Seq63 in Table 1, synthesized oligonucleotide

<400> SEQUENCE: 17
gtgggatgtc agacgtggac                                               20

<210> SEQ ID NO 18
<211> LENGTH: 20
<212> TYPE: DNA

```
<213> ORGANISM: Artificial Sequence
<220> FEATURE:
<223> OTHER INFORMATION: Seq60 in Table 1, synthesized oligonucleotide

<400> SEQUENCE: 18
catccgaggt ttactccccc                                                 20

<210> SEQ ID NO 19
<211> LENGTH: 20
<212> TYPE: DNA
<213> ORGANISM: Artificial Sequence
<220> FEATURE:
<223> OTHER INFORMATION: Seq185 in Table 1, synthesized oligonucleotide

<400> SEQUENCE: 19
aaacgtgcag tgcaacataa                                                 20

<210> SEQ ID NO 20
<211> LENGTH: 20
<212> TYPE: DNA
<213> ORGANISM: Artificial Sequence
<220> FEATURE:
<223> OTHER INFORMATION: Seq190 in Table 1, synthesized oligonucleotide

<400> SEQUENCE: 20
gtacttttgg catcctcaca                                                 20

<210> SEQ ID NO 21
<211> LENGTH: 20
<212> TYPE: DNA
<213> ORGANISM: Artificial Sequence
<220> FEATURE:
<223> OTHER INFORMATION: Seq259 in Table 1, synthesized oligonucleotide

<400> SEQUENCE: 21
agtcttgttg tgactcaact                                                 20

<210> SEQ ID NO 22
<211> LENGTH: 20
<212> TYPE: DNA
<213> ORGANISM: Artificial Sequence
<220> FEATURE:
<223> OTHER INFORMATION: Seq305 in Table 1, synthesized oligonucleotide

<400> SEQUENCE: 22
gatgatgtcc gtagcttgcc                                                 20

<210> SEQ ID NO 23
<211> LENGTH: 20
<212> TYPE: DNA
<213> ORGANISM: Artificial Sequence
<220> FEATURE:
<223> OTHER INFORMATION: Seq347 in Table 1, synthesized oligonucleotide

<400> SEQUENCE: 23
aatgggatgc catttgctgg                                                 20

<210> SEQ ID NO 24
<211> LENGTH: 20
<212> TYPE: DNA
<213> ORGANISM: Artificial Sequence
<220> FEATURE:
<223> OTHER INFORMATION: Seq209 in Table 1, synthesized oligonucleotide

<400> SEQUENCE: 24
gatatagctg gagtacaacc                                                 20
```

<210> SEQ ID NO 25
<211> LENGTH: 20
<212> TYPE: DNA
<213> ORGANISM: Artificial Sequence
<220> FEATURE:
<223> OTHER INFORMATION: Seq205 in Table 1, synthesized oligonucleotide

<400> SEQUENCE: 25
ccacgactgc agaggtatgt                                            20

<210> SEQ ID NO 26
<211> LENGTH: 20
<212> TYPE: DNA
<213> ORGANISM: Artificial Sequence
<220> FEATURE:
<223> OTHER INFORMATION: Seq340 in Table 1, synthesized oligonucleotide

<400> SEQUENCE: 26
ggtagttcgg ttggtgggga                                            20

<210> SEQ ID NO 27
<211> LENGTH: 20
<212> TYPE: DNA
<213> ORGANISM: Artificial Sequence
<220> FEATURE:
<223> OTHER INFORMATION: Seq589 in Table 1, synthesized oligonucleotide

<400> SEQUENCE: 27 gcgggggag ggaggagggg                                             20

<210> SEQ ID NO 28
<211> LENGTH: 20
<212> TYPE: DNA
<213> ORGANISM: Artificial Sequence
<220> FEATURE:
<223> OTHER INFORMATION: Seq580 in Table 1, synthesized oligonucleotide

<400> SEQUENCE: 28
cgggggtgga ggggggggag                                            20

<210> SEQ ID NO 29
<211> LENGTH: 20
<212> TYPE: DNA
<213> ORGANISM: Artificial Sequence
<220> FEATURE:
<223> OTHER INFORMATION: Seq583 in Table 1, synthesized oligonucleotide

<400> SEQUENCE: 29
cgggaagggg gggcggaggg                                            20

<210> SEQ ID NO 30
<211> LENGTH: 12
<212> TYPE: DNA
<213> ORGANISM: Artificial Sequence
<220> FEATURE:
<223> OTHER INFORMATION: Basic Anti-Parallel in Table 1, synthesized
      oligonucleotide

<400> SEQUENCE: 30
ggggttttgg gg                                                    12

<210> SEQ ID NO 31
<211> LENGTH: 15
<212> TYPE: DNA
<213> ORGANISM: Artificial Sequence

```
<220> FEATURE:
<223> OTHER INFORMATION: Thrombin Binding Aptamer (TBA) in Table 1,
      synthesized oligonucleotide

<400> SEQUENCE: 31
ggttggtgtg gttgg                                                          15

<210> SEQ ID NO 32
<211> LENGTH: 21
<212> TYPE: DNA
<213> ORGANISM: Artificial Sequence
<220> FEATURE:
<223> OTHER INFORMATION: Core Human Telomer Quadruplex in Table 1,
      synthesized oligonucleotide

<400> SEQUENCE: 32
aggttagggt tagggttagg g                                                   21

<210> SEQ ID NO 33
<211> LENGTH: 24
<212> TYPE: DNA
<213> ORGANISM: Artificial Sequence
<220> FEATURE:
<223> OTHER INFORMATION: Wild Type c-MYC in Table 1, synthesized
      oligonucleotide

<400> SEQUENCE: 33
tgagggtggg gagggtgggg aagg                                                24

<210> SEQ ID NO 34
<211> LENGTH: 22
<212> TYPE: DNA
<213> ORGANISM: Artificial Sequence
<220> FEATURE:
<223> OTHER INFORMATION: MYC22 in Table 1, synthesized oligonucleotide

<400> SEQUENCE: 34
tgagggtggg gagggtgggg aa                                                  22

<210> SEQ ID NO 35
<211> LENGTH: 24
<212> TYPE: DNA
<213> ORGANISM: Artificial Sequence
<220> FEATURE:
<223> OTHER INFORMATION: MYC12 in Table 1, synthesized oligonucleotide

<400> SEQUENCE: 35
tggggagggt ttttagggtg ggga                                                24

<210> SEQ ID NO 36
<211> LENGTH: 23
<212> TYPE: DNA
<213> ORGANISM: Artificial Sequence
<220> FEATURE:
<223> OTHER INFORMATION: PARP1 Promoter in Table 1, synthesized
      oligonucleotide

<400> SEQUENCE: 36
tgggggccga ggcggggctt ggg                                                 23

<210> SEQ ID NO 37
<211> LENGTH: 28
<212> TYPE: DNA
<213> ORGANISM: Artificial Sequence
<220> FEATURE:
<223> OTHER INFORMATION: LTRIII in Table 1, synthesized oligonucleotide
```

```
<400> SEQUENCE: 37
gggaggcgtg gcctgggcgg gactgggg                                          28

<210> SEQ ID NO 38
<211> LENGTH: 28
<212> TYPE: DNA
<213> ORGANISM: Artificial Sequence
<220> FEATURE:
<223> OTHER INFORMATION: LTRIII 6 in Table 1, synthesized
      oligonucleotide

<400> SEQUENCE: 38
ggggggcgtg gcctgggcgg gactgggg                                          28

<210> SEQ ID NO 39
<211> LENGTH: 28
<212> TYPE: DNA
<213> ORGANISM: Artificial Sequence
<220> FEATURE:
<223> OTHER INFORMATION: LTRIII 9 in Table 1, synthesized
      oligonucleotide

<400> SEQUENCE: 39
gggaggcgtg gccggggcgg gactgggg                                          28

<210> SEQ ID NO 40
<211> LENGTH: 28
<212> TYPE: DNA
<213> ORGANISM: Artificial Sequence
<220> FEATURE:
<223> OTHER INFORMATION: LTRIII 12 in Table 1, synthesized
      oligonucleotide

<400> SEQUENCE: 40
gggaggcgtg gcctgggggg gactgggg                                          28

<210> SEQ ID NO 41
<211> LENGTH: 28
<212> TYPE: DNA
<213> ORGANISM: Artificial Sequence
<220> FEATURE:
<223> OTHER INFORMATION: LTRIII 25 in Table 1, synthesized
      oligonucleotide

<400> SEQUENCE: 41
gggaggcgtg gcctgggcgg gcctgggg                                          28

<210> SEQ ID NO 42
<211> LENGTH: 28
<212> TYPE: DNA
<213> ORGANISM: Artificial Sequence
<220> FEATURE:
<223> OTHER INFORMATION: LTRIII 35 in Table 1, synthesized
      oligonucleotide

<400> SEQUENCE: 42
gggaggggtg ccctgggcgg gactgggg                                          28
```